United States Patent
Park et al.

(10) Patent No.: US 9,201,067 B2
(45) Date of Patent: *Dec. 1, 2015

(54) SIZE-CONTROLLED MACROMOLECULE

(75) Inventors: Joon Won Park, Gyeongsangbuk-do (KR); Bong Jin Hong, Gyeongsangbuk-do (KR); Young Seo Choi, Gyeonggi-do (KR); Soon Jin Oh, Gyeonsangbuk-do (KR); Kwan Yong Choi, Daegu (KR)

(73) Assignees: POSCO, Pohang (KR); POSTECH FOUNDATION, Pohang (KR)

( * ) Notice: Subject to any disclaimer, the term of this patent is extended or adjusted under 35 U.S.C. 154(b) by 2244 days.

This patent is subject to a terminal disclaimer.

(21) Appl. No.: 10/917,601

(22) Filed: Aug. 12, 2004

(65) Prior Publication Data

US 2005/0037413 A1    Feb. 17, 2005

Related U.S. Application Data

(63) Continuation-in-part of application No. PCT/KR03/01913, filed on Sep. 18, 2003, and a continuation-in-part of application No. PCT/KR03/02261, filed on Oct. 24, 2003.

(60) Provisional application No. 60/567,844, filed on May 3, 2004, provisional application No. 60/571,052, filed on May 14, 2004.

(30) Foreign Application Priority Data

Sep. 18, 2003  (WO) .................. PCT/KR03/01913
Oct. 24, 2003  (WO) .................. PCT/KR03/02261

(51) Int. Cl.
*C12M 1/34*     (2006.01)
*C12M 3/00*     (2006.01)

(Continued)

(52) U.S. Cl.
CPC ........ *G01N 33/54353* (2013.01); *C12Q 1/6834* (2013.01)

(58) Field of Classification Search
CPC .......... C12M 1/34; C12Q 1/68; C12Q 1/6834; C07H 21/04; G01N 33/54353
USPC .......... 435/6.1, 6.11, 283.1, 287.2; 536/23.1, 536/24.3

See application file for complete search history.

(56) References Cited

U.S. PATENT DOCUMENTS 5,714,166 A * 2/1998 Tomalia et al. ............... 424/486
5,837,832 A * 11/1998 Chee et al. ...................... 506/16

(Continued)

FOREIGN PATENT DOCUMENTS

EP    1 026 259 A1    8/2000
EP    1 098 004 A2    5/2001

(Continued)

OTHER PUBLICATIONS

Tokuhisa, "A new method to construct single-molecular arrays", AIST Today, 3(1):20, 2003.

(Continued)

*Primary Examiner* — Narayan Bhat
(74) *Attorney, Agent, or Firm* — Don D. Cha; Hamilton DeSanctis & Cha, LLP

(57) ABSTRACT

The present application discloses a substrate that includes a molecular layer of regularly spaced size-controlled macromolecules comprising a polymer comprising branched and linear regions in which a plurality of termini on the branched region are bound to the substrate, and a terminus of the linear region is functionalized.

13 Claims, 13 Drawing Sheets

(51) Int. Cl.
*C12M 1/00* (2006.01)
*C12Q 1/68* (2006.01)
*C07H 21/02* (2006.01)
*C07H 21/04* (2006.01)
*G01N 33/543* (2006.01)

(56) References Cited

U.S. PATENT DOCUMENTS

| | | | | |
|---|---|---|---|---|
| 5,945,293 | A | 8/1999 | Siiman | |
| 6,074,884 | A | 6/2000 | Siiman | |
| 6,117,631 | A | 9/2000 | Nilsen | |
| 6,172,218 | B1 * | 1/2001 | Brenner | 506/16 |
| 6,312,809 | B1 * | 11/2001 | Crooks et al. | 428/411.1 |
| 7,247,384 | B2 | 7/2007 | Cai | |

FOREIGN PATENT DOCUMENTS

| | | | |
|---|---|---|---|
| JP | 2000210082 | | 8/2000 |
| JP | 2000295990 | | 10/2000 |
| JP | 2001108683 | | 4/2001 |
| JP | 2001128683 | A | 5/2001 |
| WO | WO 99/43287 | A2 | 9/1999 |
| WO | WO 02/33412 | A1 | 4/2002 |

OTHER PUBLICATIONS

Smith and Muller, "Dendritic biomimicry: microenvironmental effects on tryptophan fluorescence," Chem. Commun., (18):1915-1916, 1999.

Nierengarten, et al., "Macrocyclization on the Fullerene Core: Direct regio- and diastereoselective multi-functionalization~," Helvetica Chimica Acta, 80(7):2238-2276, 1997.

Beier and Hoheisel, "Versatile derivatisation of solid support media for covalent bonding on DNA-microchips," Nucleic Acids Research, 27(9):1970-1977, 1999.

Slomkowski, et al., "Inorganic-organic sys. with tailored prop. controlled on molecular, macromolecular~," Reactive and Functional Polymers, 41(1-3):45-57, 1999.

Tsubokawa, et al., "Grafting of 'dendrimer-like' highly branched polymer onto ultrafine silia surface," Reactive and Functional Polymers, 37(1-3):75-82, 1998.

Whitesell and Chang, "Directionally Aligned Helical Peptides on Surfaces," Science, 261:73-76, 1993.

Niikura, et al., "Direct Monitoring of DNA Polymerase Reactions on a Quartz-Crystal Microbalance," J. Am. Chem. Soc. 120:8537-8538, 1998.

Levicky, et al., "Using Self-Assembly to control the structure of DNA Monolayers on Gold:~," J. Am. Chem. Soc. 120:9787-9792, 1998.

Hong, et al., "Self-Assembly of a Dendron through Multiple Ionic Interaction to Give Mesospacing between Reactive Amine Groups on the Surface," Langmuir 19:2357-2365, 2003.

Choi et al., "Efficient protein-ligand interaction by guaranteeing mesospacing between immobilized biotins," Chem. Commun., (11):1316-1317, 2004.

Tokuhisa et al., "A New Method to Fabricate Single-Molecule Nanoarrays Using Dendrimer-Based Templates," AIST Today International Edition 3(1)2003.

Tokuhisa et al., "A New Method to Fabricate Single-Molecule Nanoarrays Using Dendrimer-Based Templates," Advanced Materials 15(18) 2003.

Whitesell, James et al., "Directionally Aligned Helical Peptides on Surfaces." Science, 1993, vol. 261, p. 73-76.

Siiman, Olayi. Et al., "Tris (3-mercaptopropyl)-N-glycylaminomethane as a New Linker to Bridge Antibody with Metal Particles for Biological Cell Separations." Bioconjugate Chem., 2000, vol. 11, p. 549-556.

Yam, C. et al., "Preparation, Characterization, and Heck Reaction of Multidentate Thiolate Films on Gold Surfaces." Langmuir, 2003, vol. 19, p. 6862-6868.

Xiao. et al., "The First Organosiloxane Thin Films Derived from SiCl3-Terminated Dendrons. Thickness-Dependent Nano-and Mesoscopic Structures at the Films Deposited on Mica by Spin-Coating." Langmuir, 2002, vol. 18, p. 7728-7739.

Yam, C. et al., "Preparation and Heck Reaction of Multidentate Carbosilane Films Derived from Focally Functionalized and Ally-Terminated Dendrons on Hydrogen-Terminated Silicon(III) Surfaces." Langmuir, 2004, vol. 20, p. 1228-1233.

* cited by examiner

SIZE-CONTROLLED MACROMOLECULE

CROSS-REFERENCE TO RELATED APPLICATIONS

The present application is a continuation-in-part application of U.S. patent application Ser. No. 10/363,946, filed Mar. 5, 2003, which is a §371 U.S. National Stage Application of PCT Patent Application No. PCT/KR01/01501, filed Sep. 5, 2001. This application is also a continuation-in-part application of PCT Patent Application No. PCT/KR03/01913, filed Sep. 18, 2003, and continuation-in-part application of PCT Patent Application No. PCT/KR03/02261, filed Oct. 24, 2003. This application also claims the benefit of priority to U.S. Provisional Patent Application Nos. 60/567,844, filed May 3, 2004, and 60/571,052, filed May 14, 2004.

BACKGROUND OF THE INVENTION

1. Field of the Invention

The present invention relates to the field of hyperbranched macromolecules. The present invention relates to the field of functionalized substrates on which is bound the macromolecules. The present invention also relates to the field of functionalized size-controlled dendrimers and dendrons that are used to bind to a functionalized substrate at one end of the dendron and to a target-specific ligand on the other end. The present invention also relates to the field of combinatorial chemistry, specific protein detection methods, specific nucleic acid or nucleic acid/peptide hybrid detection methods using a functionalized substrate to which is bound a hyperbranched polymer linked to a probe biomolecule.

2. General Background and State of the Art

Since the first report (Fodor et al., Nature 364, 555-556 (1993); Saiki et al., Proc. Natl. Acad. Sci. USA 86, 6230-6234 (1986)), DNA microarrays have attracted a great deal of attention because they allow high-throughput analysis of the DNA sequence, genetic variations, and gene expression. It is known that this methodology requires improvement in terms of fidelity, reproducibility, and spot homogeneity that are essential for the standardization and application to human gene diagnosis (Hackett et al., Nature Biotechnology 21, 742-743 (2003)). These shortcomings are caused mainly by the variations in the nature of the surface and molecular interlayer structures that are far from ideal. Likewise, the field of high-throughput target detection systems encompasses bioassays utilizing immobilized bioactive molecules and biomolecules.

Here we show that DNA microarrays fabricated on a nanoscale-controlled surface discriminates single mismatched pairs as effectively as DNA does in solution. This approach provides an ideal DNA-microarray in which each probe DNA strand is given ample space enough to interact with an incoming target DNA with minimal steric hindrance. The dramatically increased discrimination efficiency promises the very reliable diagnosis of human genes. Moreover, the approach is general enough to be applied to various bioassays utilizing immobilized bioactive molecules and biomolecules.

Affinity purification is a well-known technique for the separation and identification of ligand-binding proteins (Cuatrecasas et al., Proc. Natl. Acad. Sci. U.S.A. 1968, 61, 636-643). A unique interaction between a ligand covalently attached to an insoluble matrix and the complementary target protein provides the specificity required for the isolation of biomolecules from complex mixtures. However, its widespread use has been hampered by the limited choice and instability of conventional matrices. Significant nonspecific binding of proteins to many solid supports has been a persistent problem in establishing new matrices (Cuatrecasas, P. J. Biol. Chem. 1970, 245, 3059-3065). It is therefore desirable to find new matrices that are comparable to the traditional matrices in terms of the specificity while exhibiting environmental stability and capability of well-defined and facile attachment of ligands.

Aminopropyl-controlled pore glass (or AMPCPG) that is originally used for the solid-phase peptide synthesis appears to have many desirable features. However, the controlled pore glass (or CPG) surface is polar and retains partial negative charge even when coated (Hudson, D. J. Comb. Chem. 1999, 1, 403-457). The feature plays a key role in significant nonspecific binding of proteins. Therefore, application on both affinity chromatography and solid-phase peptide synthesis has been limited. Once the obstacles are eliminated, widespread use of the materials can be expected.

Accessibility of ligands is a key factor in determining binding capacity. The traditional approaches are introducing a spacer molecule and increasing the ligand concentration for better exposition of the ligand on the surface (Rusin, et al., Biosensors & Bioelectronics 1992, 7, 367-373; Suen et al., Ind. Eng. Chem. Res. 2000, 39, 478-487; Penzol et al., Biotechnol and Bioeng. 1998, 60, 518-523; Spinke et al., J. Chem. Phys. 1993, 99, 7012-7019). The approach works to a certain degree, but insufficient space between the ligands and random distribution of capture molecules over the surfaces are the issues yet to be solved (Hearn et al., J. Chromatogr. A. 1990, 512, 23-39; Murza et al., J. Chromatogr. B. 2000, 740, 211-218; Xiao et al., Langmuir 2002, 18, 7728-7739). By far two methods have been employed to improve these shortcomings. One way is to utilize a big molecule such as protein as a placeholder. The protein is conjugated onto the matrix, and the placeholder molecule was cleaved off and washed out. In this way, certain distance between the linkers left on the matrix is secured. Nevertheless, choice of the placeholder molecule and design of the deprotection route have to be elaborately optimized for every different situation (Hahn et al., Anal. Chem. 2003, 75, 543-548). Another way is to employ a cone-shape dendron that gives a highly ordered self-assembled monolayer and utilize an active functional group at the apex of the dendron (Xiao et al., Langmuir 2002, 18, 7728-7739; Whitesell et al., Langmuir 2003, 19, 2357-2365).

Here we present modification of AMPCPG with dendrons, further attachment of GSH at the apex of the dendrons, and characteristics of the surface materials in terms of GST proteins binding. A dendron featuring three or nine carboxylic acid groups at the termini and one amine group at the apex has been introduced into the matrices. Their carboxylic groups were covalently linked with the solid surface. Due to wide use and understating of glutathione S-transferase (or GST) gene fusion system, glutathione was chosen as a ligand to be tethered on the dendron-treated matrix. Ligand binding property of the matrix has been investigated with GST and two fusion proteins (GST-PX$^{P47}$, GST-Munc-18) (Smith et al., Gene 1988, 67, 31-40; Sebastian et al., Chromatogr. B. 2003, 786, 343-355; Wu et al., Chromatogr. B. 2003, 786, 177-185; De Carlos et al., J. Chromatogr. B. 2003, 786, 7-15).

SUMMARY OF THE INVENTION

The present invention provides a substrate bound thereon size-controlled, preferably cone shaped molecules linked to a ligand.

The present invention is directed to a substrate comprising a molecular layer of regularly spaced size-controlled macromolecules comprising a polymer comprising branched and linear regions in which a plurality of termini on the branched region are bound to the substrate, and a terminus of the linear region is functionalized. On the substrate, the macromolecules may be spaced at regular intervals. In particular, the macromolecules may be spaced at regular intervals between about 0.1 nm and about 100 nm between the linear functionalized groups. In particular, the macromolecules may be spaced at regular intervals of about 10 nm.

In the above-described substrate, the terminus of the branched region may be functionalized with —COZ, —NHR, —OR', or —PR"$_3$, wherein Z may be a leaving group, wherein R may be an alkyl, wherein R' may be alkyl, aryl, or ether, and R" may be H, alkyl, alkoxy, or O. In particular, COZ may be ester, activated ester, acid halide, activated amide, or CO-imiazoyl; R may be $C_1$-$C_4$ alkyl, and R' may be $C_1$-$C_4$ alkyl. Further, in the above described substrate, the polymer may be a dendron. Still further, the linear region of the polymer may be comprised of a spacer region. And the spacer region may be connected to the branched region via a first functional group. Such first functional group may be without limitation —NH$_2$, —OH, —PH$_3$, —COOH, —CHO, or —SH. Still further, the spacer region may comprise a linker region covalently bound to the first functional group.

In the substrate described above, the linker region may comprise a substituted or unsubstituted alkyl, alkenyl, alkynyl, cycloalkyl, aryl, ether, polyether, ester, or aminoalkyl group. Still further, spacer region may comprise a second functional group. The second functional group may include without limitation —NH$_2$, —OH, —PH$_3$, —COOH, —CHO, or —SH. The second functional group may be located at the terminus of the linear region. And a protecting group may be bound to the terminus of the linear region. Such protecting group may be acid labile or base labile.

In another embodiment of the invention, in the substrate as described above, a target-specific ligand may be bound to the terminus of the linear region. In particular, the target-specific ligand may be a chemical compound, DNA, RNA, PNA, aptamer, peptide, polypeptide, carbohydrate, antibody, antigen, biomimetics, nucleotide analog, or a combination thereof. Further, the distance between the target-specific ligands bound to the linear region of the macromolecules may be from about 0.1 to about 100 nm.

In yet another embodiment of the invention, the substrate described above may be made of semiconductor, synthetic organic metal, synthetic semiconductor, metal, alloy, plastic, silicon, silicate, glass, or ceramic. In particular, the substrate may be without limitation a slide, particle, bead, micro-well, or porous material. The porous material may be a membrane, gelatin or hydrogel. And further in particular, the bead may be a controlled pore bead.

The invention is also directed to a method for manufacturing a molecular layer of regularly spaced size-controlled macromolecules comprising a polymer comprising branched and linear regions in which a plurality of termini on the branched region are bound to the substrate, and a terminus of the linear region is functionalized, comprising:

(i) functionalizing the substrate so that it will react with the termini of the macromolecules; and (ii) contacting the macromolecules to the substrate so that the termini and the substrate form a bond.

In this method, the substrate may be made of without limitation semiconductor, synthetic organic metal, synthetic semiconductor, metal, alloy, plastic, membrane, silicon, silicate, glass, or ceramic. The substrate may be a slide, bead, microwell, or porous material. The porous material may be a hydrogel, gelatin, or membrane. The bead may be a controlled pore bead.

Further, in the method described above, a target-specific ligand is fixed to the terminus of the linear region, comprising the steps of i) removing protecting group from the terminus of the linear region of the macromolecules on the substrate; and ii) contacting the target-specific ligand or a linker molecule linked to the target-specific ligand to the terminus of the linear region of the macromolecules on the substrate so that the ligand or the linker molecule and the terminus form a bond, wherein the linker molecule is a homobifunctional or heterobifunctional linker.

In this method, the presence of the macromolecules on the substrate results in minimal interference in the binding of the target-specific ligand to the linear termini. Further in this method, the presence of the macromolecules on the substrate results in minimal interference in the detection of a target specific to the target-specific ligand. Still further, the target-specific ligand may be spaced at regular intervals. In particular, the target-specific ligands may be placed on the substrate at a low density. In the above-described method, the target-specific ligand may be a chemical compound, DNA, RNA, PNA, aptamer, peptide, polypeptide, enzyme, carbohydrate, polysaccharide, antibody, antigen, biomimetics, nucleotide analog, or a combination thereof.

In another embodiment, the invention is also directed to a diagnostic system for detecting a mutation in a gene, comprising the above-described substrate, wherein the terminus of the linear region is fixed with target specific oligonucleotides. Such oligonucleotides may be specific for cancer related genes. In particular, the cancer related gene may be p53.

In still another embodiment, the invention is directed to a method for detecting presence of a mutation in a gene, comprising contacting the above-described substrate with a sample containing the gene to be assayed, wherein the terminus of the linear region is fixed with a target specific oligonucleotide. In this method, the gene may be a cancer related gene. Further, the gene may be p53.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given wherein below, and the accompanying drawings which are given by way of illustration only, and thus are not limitative of the present invention, and wherein;

FIG. 3a shows a scheme for surface modification and hybridization. FIG. 3b shows the molecular structure of the employed dendron. FIG. 3c shows the DNA sequence of the probe and target DNA strands. Probe oligonucleotides include Probe 1: 5'-NH$_2$—C$_6$-CAT TCC GNG TGT CCA-3' (SEQ ID NO:1) and Probe 2: 5'-NH$_2$—C$_6$-(T)$_{30}$-CAT TCC GNG TGT CCA-3' (SEQ ID NO:2). Target nucleotides include Target 1: 5'-Cy3-TGG ACA CTC GGA ATG-3' (SEQ ID NO:3) and Target 2: 5'-Cy3-CCT ACG AAA TCT ACT GGA ACG AAA TCT ACT TGG ACA CTC GGA ATG-3' (SEQ ID NO:4).

DETAILED DESCRIPTION OF THE PREFERRED EMBODIMENTS

Figure 1:
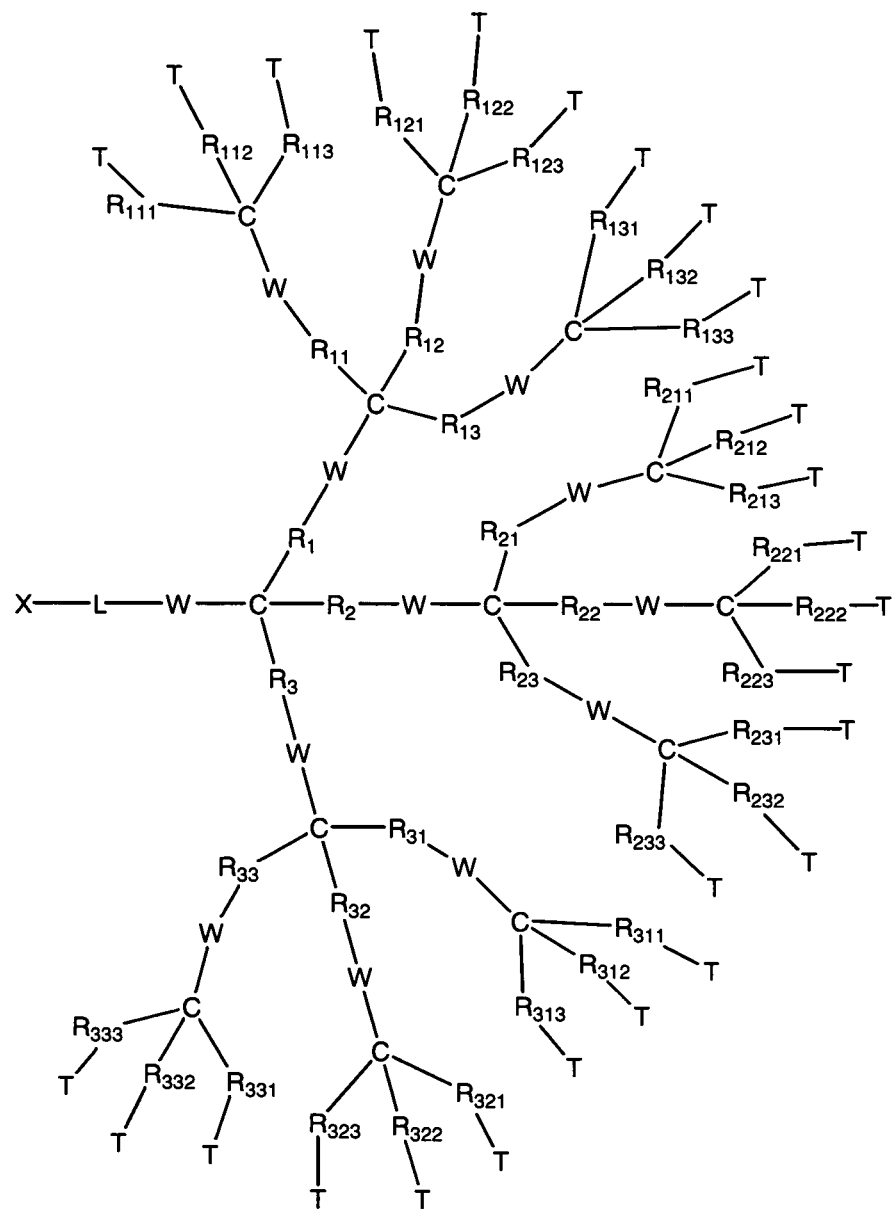
FIG. 1 shows Formula I, which is a branched/linear polymer or a size-controlled macromolecule.

In the present application, "a" and "an" are used to refer to both single and a plurality of objects.

As used herein, "aptamer" means a single-stranded, partially single-stranded, partially double-stranded or double-stranded nucleotide sequence, advantageously replicatable nucleotide sequence, capable of specifically recognizing a selected nonoligonucleotide molecule or group of molecules by a mechanism other than Watson-Crick base pairing or triplex formation.

As used herein, "bifunctional," "trifunctional" and "multifunctional," when used in reference to a synthetic polymer or multivalent homo- or heteropolymeric hybrid structure, mean bivalent, trivalent or multivalent, as the case may be, or comprising two, three or multiple specific recognition elements, defined sequence segments or attachment sites.

As used herein, "biomimetic" means a molecule, group, multimolecular structure or method that mimics a biological molecule, group of molecules, structure.

As used herein, "dendritic molecule" is a molecule exhibiting regular dendritic branching, formed by the sequential or generational addition of branched layers to or from a core.

As used herein, "dendritic polymer" is a polymer exhibiting regular dendritic branching, formed by the sequential or generational addition of branched layers to or from a core. The term dendritic polymer encompasses "dendrimers", which are characterized by a core, at least one interior branched layer, and a surface branched layer (see, e.g., Petar et al. Pages 641-645 In Chem. in Britain, (August 1994). A "dendron" is a species of dendrimer having branches emanating from a focal point, which is or can be joined to a core, either directly or through a linking moiety to form a dendrimer. Many dendrimers comprise two or more dendrons joined to a common core. However, the term dendrimer may be used broadly to encompass a single dendron.

Dendritic polymers include, but are not limited to, symmetrical and asymmetrical branching dendrimers, cascade molecules, arborols, and the like. In a preferred embodiment, the branch arms may be of equal length. The branching may typically occur without limitation at the hydrogen atoms of a terminal —$NH_2$ group on a preceding generation branch, for example. However, it is also contemplated that asymmetric dendimers may also be used. For instance, lysine-based dendrimers are asymmetric, in that the branch arms are of a different length. One branch occurs at the epsilon nitrogen of the lysine molecule, while another branch occurs at the alpha nitrogen, adjacent to the reactive carboxy group which attaches the branch to a previous generation branch.

Further, it is understood that even though not formed by regular sequential addition of branched layers, hyper-branched polymers, e.g., hyperbranched polyols, may be equivalent to a dendritic polymer where the branching pattern exhibits a degree of regularity approaching that of a dendrimer.

As used herein, "hyperbranched" or "branched" as it is used to describe a macromolecule or a dendron structure is meant to refer to a plurality of polymers having a plurality of termini which are able to bind covalently or ionically to a substrate. In one embodiment, the macromolecule comprising the branched or hyperbranched structure is "pre-made" and is then attached to a substrate. Accordingly, the inventive macromolecule excludes polymer cross-linking methods as disclosed in U.S. Pat. No. 5,624,711 (Sundberg et al.).

As used herein, "immobilized" means insolubilized or comprising, attached to or operatively associated with an insoluble, partially insoluble, colloidal, particulate, dispersed, suspended and/or dehydrated substance or a molecule or solid phase comprising or attached to a solid support.

As used herein, "library" refers to a random or nonrandom mixture, collection or assortment of molecules, materials, surfaces, structural shapes, surface features or, optionally and without limitation, various chemical entities, monomers, polymers, structures, precursors, products, modifications, derivatives, substances, conformations, shapes, or features.

As used herein, "ligand" means a selected molecule capable of specifically binding to another molecule by affinity-based attraction, which includes complementary base pairing. Ligands include, but are not limited to, nucleic acids, various synthetic chemicals, receptor agonists, partial agonists, mixed agonists, antagonists, response-inducing or stimulus molecules, drugs, hormones, pheromones, transmitters, autacoids, growth factors, cytokines, prosthetic groups, coenzymes, cofactors, substrates, precursors, vitamins, toxins, regulatory factors, antigens, haptens, carbohydrates, molecular mimics, structural molecules, effector molecules, selectable molecules, biotin, digoxigenin, crossreactants, analogs, competitors or derivatives of these molecules as well as library-selected nonoligonucleotide molecules capable of specifically binding to selected targets and conjugates formed by attaching any of these molecules to a second molecule.

As used herein, "linker molecule," and "linker" when used in reference to a molecule that joins the branched portion of a size-controlled macromolecule such as a branched/linear polymer to a protecting group or a ligand. Linkers may include, for instance and without limitation, spacer molecules, for instance selected molecules capable of attaching a ligand to a dendron.

As used herein, "low density" refers to about 0.01 to about 0.5 probe/nm$^2$, preferably about 0.05 to about 0.2, more preferably about 0.075 to about 0.15, and most preferably about 0.1 probe/nm$^2$.

As used herein, "molecular mimics" and "mimetics" are natural or synthetic nucleotide or nonnucleotide molecules or groups of molecules designed, selected, manufactured, modified or engineered to have a structure or function equivalent or similar to the structure or function of another molecule or group of molecules, e.g., a naturally occurring, biological or selectable molecule. Molecular mimics include molecules and multimolecular structures capable of functioning as replacements, alternatives, upgrades, improvements, structural analogs or functional analogs to natural, synthetic, selectable or biological molecules.

As used herein, "nucleotide analog" refers to molecules that can be used in place of naturally occurring bases in nucleic acid synthesis and processing, preferably enzymatic as well as chemical synthesis and processing, particularly modified nucleotides capable of base pairing and optionally synthetic bases that do not comprise adenine, guanine, cytosine, thymidine, uracil or minor bases. This term includes, but is not limited to, modified purines and pyrimidines, minor bases, convertible nucleosides, structural analogs of purines and pyrimidines, labeled, derivatized and modified nucleosides and nucleotides, conjugated nucleosides and nucleotides, sequence modifiers, terminus modifiers, spacer modifiers, and nucleotides with backbone modifications, including, but not limited to, ribose-modified nucleotides, phosphoramidates, phosphorothioates, phosphonamidates, methyl phosphonates, methyl phosphoramidites, methyl phosphonamidites, 5'-β-cyanoethyl phosphoramidites, methylenephosphonates, phosphorodithioates, peptide nucleic acids, achiral and neutral internucleotidic linkages and normucleotide bridges such as polyethylene glycol, aromatic polyamides and lipids.

As used herein, "polymer" or "branched/linear polymer" refers to a molecule having a branched structure at one end of the molecule and a linear portion at the other end so that the branched portion binds to a substrate and the linear portion binds to a ligand, probe or a protecting group.

As used herein, "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The term may also include variants on the traditional peptide linkage joining the amino acids making up the polypeptide.

As used herein, "protecting group" refers to a group that is joined to a reactive group (e.g., a hydroxyl or an amine) on a molecule. The protecting group is chosen to prevent reaction of the particular radical during one or more steps of a chemical reaction. Generally the particular protecting group is chosen so as to permit removal at a later time to restore the reactive group without altering other reactive groups present in the molecule. The choice of a protecting group is a function of the particular radical to be protected and the compounds to which it will be exposed. The selection of protecting groups is well known to those of skill in the art. See, for example Greene et al., Protective Groups in Organic Synthesis, 2nd ed., John Wiley & Sons, Inc. Somerset, N.J. (1991), which is incorporated by reference herein in its entirety.

As used herein, "protected amine" refers to an amine that has been reacted with an amino protecting group. An amino protecting group prevents reaction of the amide function during attachment of the branched termini to a solid support in the situation where the linear tip functional group is an amino group. The amino protecting group can be removed at a later time to restore the amino group without altering other reactive groups present in the molecule. For example, the exocyclic amine may be reacted with dimethylformamide diethylacetal to form the dimethylaminomethylenamino function. Amino protecting groups generally include carbamates, benzyl radicals, imidates, and others known to those of skill in the art. Preferred amino protecting groups include, but are not limited to, p-nitrophenylethoxycarbonyl or dimethyaminomethylenamino.

As used herein, "regular intervals" refers to the spacing between the tips of the size-controlled macromolecules, which is a distance from about 1 nm to about 100 nm so as to allow room for interaction between the target-specific ligand and the target substantially without steric hindrance. Thus, the layer of macromolecules on a substrate is not too dense so that specific molecular interactions may occur.

As used herein, "solid support" refers to a composition comprising an immobilization matrix such as but not limited to, insolubilized substance, solid phase, surface, substrate, layer, coating, woven or nonwoven fiber, matrix, crystal, membrane, insoluble polymer, plastic, glass, biological or biocompatible or bioerodible or biodegradable polymer or matrix, microparticle or nanoparticle. Solid supports include, for example and without limitation, monolayers, bilayers, commercial membranes, resins, matrices, fibers, separation media, chromatography supports, polymers, plastics, glass, mica, gold, beads, microspheres, nanospheres, silicon, gallium arsenide, organic and inorganic metals, semiconductors, insulators, microstructures and nanostructures. Microstructures and nanostructures may include, without limitation, microminiaturized, nanometer-scale and supramolecular probes, tips, bars, pegs, plugs, rods, sleeves, wires, filaments, and tubes.

As used herein, "spacer molecule" refers to one or more nucleotide and/or normucleotide molecules, groups or spacer arms selected or designed to join two nucleotide or normucleotide molecules and preferably to alter or adjust the distance between the two nucleotide or normucleotide molecules.

As used herein, "specific binding" refers to a measurable and reproducible degree of attraction between a ligand and its specific binding partner or between a defined sequence segment and a selected molecule or selected nucleic acid sequence. The degree of attraction need not be maximized to be optimal. Weak, moderate or strong attractions may be appropriate for different applications. The specific binding which occurs in these interactions is well known to those skilled in the art. When used in reference to synthetic defined sequence segments, synthetic aptamers, synthetic heteropolymers, nucleotide ligands, nucleotide receptors, shape recognition elements, and specifically attractive surfaces. The term "specific binding" may include specific recognition of structural shapes and surface features. Otherwise, specific binding refers explicitly to the specific, saturable, noncovalent interaction between two molecules (i.e., specific binding partners) that can be competitively inhibited by a third molecule (i.e., competitor) sharing a chemical identity (i.e., one or more identical chemical groups) or molecular recognition property (i.e., molecular binding specificity) with either specific binding partner. The competitor may be, e.g., a crossreactant, or analog of an antibody or its antigen, a ligand or its receptor, or an aptamer or its target. Specific binding between an antibody and its antigen, for example, can be competitively inhibited either by a crossreacting antibody or by a crossreacting antigen. The term "specific binding" may be used for convenience to approximate or abbreviate a subset of specific recognition that includes both specific binding and structural shape recognition.

As used herein, "substrate," when used in reference to a substance, structure, surface or material, means a composition comprising a nonbiological, synthetic, nonliving, planar, spherical or flat surface that is not heretofore known to comprise a specific binding, hybridization or catalytic recognition site or a plurality of different recognition sites or a number of different recognition sites which exceeds the number of different molecular species comprising the surface, structure or material. The substrate may include, for example and without limitation, semiconductors, synthetic (organic) metals, synthetic semiconductors, insulators and dopants; metals, alloys, elements, compounds and minerals; synthetic, cleaved, etched, lithographed, printed, machined and microfabricated slides, devices, structures and surfaces; industrial polymers, plastics, membranes; silicon, silicates, glass, metals and ceramics; wood, paper, cardboard, cotton, wool, cloth, woven and nonwoven fibers, materials and fabrics; nanostructures and microstructures unmodified by immobilization probe molecules through a branched/linear polymer.

As used herein, "target-probe binding" means two or more molecules, at least one being a selected molecule, attached to one another in a specific manner. Typically, a first selected molecule may bind to a second molecule that either indirectly, e.g., through an intervening spacer arm, group, molecule, bridge, carrier, or specific recognition partner, or directly, i.e., without an intervening spacer arm, group, molecule, bridge, carrier or specific recognition partner, advantageously by direct binding. A selected molecule may specifically bind to a nucleotide via hybridization. Other noncovalent means for conjugation of nucleotide and normucleotide molecules include, e.g., ionic bonding, hydrophobic interactions, ligand-nucleotide binding, chelating agent/metal ion pairs or specific binding pairs such as avidin/biotin, streptavidin/biotin, anti-fluorescein/fluorescein, anti-2,4-dinitrophenol (DNP)/DNP, anti-peroxidase/peroxidase, anti-digoxigenin/digoxigenin or, more generally, receptor/ligand. For example, a reporter molecule such as alkaline phosphatase, horseradish peroxidase, β-galactosidase, urease, luciferase, rhodamine, fluorescein, phycoerythrin, luminol, isoluminol, an acridinium ester or a fluorescent microsphere which is attached, e.g., for labeling purposes, to a selected molecule or selected nucleic acid sequence using avidin/biotin, streptavidin/biotin, anti-fluorescein/fluorescein, anti-peroxidase/peroxidase, anti-DNP/DNP, anti-digoxigenin/digoxigenin or receptor/ligand (i.e., rather than being directly and covalently attached) may be conjugated to the selected molecule or selected nucleic acid sequence by means of a specific binding pair.

Macromolecule Polymer Formulation

FIG. 1 diagram may be referred to in describing the inventive polymer. Various R, T, W, L, and X group variables are noted in FIG. 1. The inventive macromolecule polymer may comprise any branched or hyperbranched, symmetrical or asymmetrical polymer. The branched termini of the polymer may bind to the substrate preferably by a plurality of the termini. The linear end of the polymer may end with a functional group to which may be attached a protecting group or a target-specific ligand. The distance between the probes among the plurality of polymers on a substrate may be from about 0.1 nm to about 100 nm, preferably about 1 nm to about 100 nm, preferably, about 2 nm to about 70 nm, more preferably about 2 nm to about 60 nm, most preferably about 2 nm to about 50 nm.

R-Group

Referring to Formula I set forth in FIG. 1, the polymer generally comprises a branched section, wherein a plurality of the ends are functionalized to bind to a substrate. Within this branched section, the first generation group of branches $R_x$ ($R_1$, $R_2$, $R_3$) is connected to a second generation group of branches $R_{xx}$ ($R_{11}$, $R_{12}$, $R_{13}$, $R_{21}$, $R_{22}$, $R_{23}$, $R_{31}$, $R_{32}$, $R_{33}$) by a functional group, W. The second generation group of branches is connected to a third generation group of branches $R_{xxx}$ ($R_{111}$, $R_{112}$, $R_{113}$, $R_{121}$, $R_{122}$, $R_{123}$, $R_{131}$, $R_{132}$, $R_{133}$, $R_{211}$, $R_{212}$, $R_{213}$, $R_{221}$, $R_{222}$, $R_{223}$, $R_{231}$, $R_{232}$, $R_{233}$, $R_{311}$, $R_{312}$, $R_{313}$, $R_{321}$, $R_{322}$, $R_{323}$, $R_{331}$, $R_{332}$, $R_{333}$) by a functional group W. And further fourth generation may be connected to the third generation branches in like fashion. The terminal R group is functionalized so that it is capable of binding to the substrate.

The R groups of all generations may be the same or different. Typically, the R group may be a repeating unit, a linear or branched organic moiety, such as but not limited to alkyl, alkenyl, alkynyl, cycloalkyl, aryl, ether, polyether, ester, aminoalkyl, and so on. However, it is also understood that not all of the R groups need to be the same repeating unit. Nor do all valence positions for the R group need be filled with a repeating unit. For instance, in the first generation branch, $R_x$, $R_1$, $R_2$, $R_3$ all of the R groups at this branch level may be the same repeating units. Or, $R_1$ may be a repeating unit, and $R_2$ and $R_3$ may be H or any other chemical entity. Or, $R_2$ may be a repeating unit, and $R_1$ and $R_3$ may be H or any other chemical entity. Likewise, for the second and third generation branches, any R group may be a repeating unit, H or any other chemical entity.

Thus, a variety of shapes of polymers may be made in this way, for instance, if $R_1$, $R_1$, $R_{111}$, $R_{112}$ and $R_{113}$ are the same repeating units, and all other R groups are H's or any number of small neutral molecule or atom, then a fairly long and thin polymer having a branch with three functional group termini for $R_{111}$, $R_{112}$ and $R_{113}$ is made. A variety of other optional chemical configurations are possible. Thus, it is possible to obtain from about 3 to about 81 termini having a functional group capable of binding to a substrate. A preferable number of termini may be from about 3 to about 75, from about 3 to about 70, from about 3 to about 65, from about 3 to about 60, from about 3 to about 55, from about 3 to about 50, from about 3 to about 45, from about 3 to about 40, from about 3 to about 35, from about 3 to about 30, from about 3 to about 27, from about 3 to about 25, from about 3 to about 21, from about 3 to about 18, from about 3 to about 15, from about 3 to about 12, from about 3 to about 9, or from about 3 to about 6.

T-Terminal Group

Terminal groups, T, are functional groups that are sufficiently reactive to undergo addition or substitution reactions. Examples of such functional groups include without limitation amino, hydroxyl, mercapto, carboxyl, alkenyl, allyl, vinyl, amido, halo, urea, oxiranyl, aziridinyl, oxazolinyl, imidazolinyl, sulfonato, phosphonato, isocyanato, isothiocyanato, silanyl, and halogenyl.

W-Functional Group

In Formula I in FIG. 1, W may be any functional group that may link a polymer to another (or any other divalent organic moiety), such as but not limited to ether, ester, amide, ketone, urea, urethane, imide, carbonate, carboxylic acid anhydride, carbodiimide, imine, azo group, amidine, thiocarbonyl, organic sulphide, disulfide, polysulfide, organic sulphoxide, sulphite, organic sulphone, sulphonamide, sulphonate, organic sulphate, amine, organic phosphorous group, alkylene, alkyleneoxide, alkyleneamine and so on.

L—Spacer or Linker Group

In FIG. 1, the linear portion of the polymer may include a spacer domain comprised of a linker region optionally interspersed with functional groups. The linker region may be comprised of a variety of polymers. The length of the linker may be determined by a variety of factors, including the number of branched functional groups binding to the substrate, strength of the binding to the substrate, the type of R group that is used, in particular, the type of repeating unit that is used, the type of the protecting group or target specific ligand that is to be attached at the apex of the linear portion of the polymer. Therefore, it is understood that the linker is not to be limited to any particular type of polymer or of any particular length. However, as a general guideline, the length of the linker may be from about 0.5 nm to about 20 nm, preferably, about 0.5 nm to about 10 nm, and most preferably about 0.5 nm to about 5 nm.

The chemical construct of the linker may include without limitation, a linear or branched organic moiety, such as but not limited to substituted or unsubstituted alkyl, alkenyl, alkynyl, cycloalkyl, cycloalkenyl, aryl, ether, polyether, ester, aminoalkyl, polyalkenylglcol and so on. The linker may further include functional groups such as those described above, and as such is not limited to any particular structure.

The linker group functionalized at the tip may comprise a protective group. Thus, in one aspect, the present invention is directed to a substrate to which is attached a plurality of branched/linear polymers comprising linear tip attached to a protective group. Such a substrate may be chemically reacted to strip off the protective group to be replaced with a target specific ligand. Therefore, in a functional use of the present inventive system, a substrate bound with a population of branched/linear polymers linked to a library of target specific ligands is provided.

X—Protecting Group

The choice of protecting group depends on numerous factors such as the desirability of acid-labile or base-lability. Therefore, the invention is not limited to any particular protecting group so long as it serves the function of preventing the reaction of the functional group to another chemical entity, and that it is capable of being stripped under desired specified conditions. Preferably, the protecting group is easily stripped away. Examples of such protecting groups that may be used in the present invention include without limitation the following:

Amino acid protecting groups: Methyl, Formyl, Ethyl, Acetyl, t-Butyl, Anisyl, Benzyl, Trifluroacetyl, N-hydroxysuccinimide, t-Butyloxycarbonyl, Benzoyl, 4-Methylbenzyl, Thioanizyl, Thiocresyl, Benzyloxymethyl, 4-Nitrophenyl, Benzyloxycarbonyl, 2-Nitrobenzoyl, 2-Nitrophenylsulphenyl, 4-Toluenesulphonyl, Pentafluorophenyl, Diphenylmethyl (Dpm), 2-Chlorobenzyloxycarbonyl, 2,4,5-trichlorophenyl, 2-bromobenzyloxycarbonyl, 9-Fluorenylmethyloxycarbonyl, Triphenylmethyl, 2,2,5,7,8-pentamethyl-chroman-6-sulphonyl, Phthaloyl, 3-Nitrophthaloyl, 4,5-dichlorophthaloyl, tetrabromophthaloyl, tetrachlorophthaloyl.

Protecting groups for alcohols: p-Anisyloxymethyl (p-AOM), Benzyloxymethyl (BOM), t-Butoxymethyl, 2-Chlorotetrahydrofuran (THF), Guaiacolmethyl (GUM), (1R)-Menthoxymethyl (MM), p-Methoxybenzyloxymethyl (PMBM), metoxyethoxymethyl (MEM), Methoxymethyl (MOM), o-Nitrobenzyloxymethyl, (Phenyldimethylsilyl) methoxymethyl (SMOM), 2-(Trimethylsilyl)ethoxymethyl (SEM).

DNA, RNA protecting reagent: 2'-OMe-Ac-C-CE Phosphoramidite, 2'-OMe-Ac-RNA CPG, 2'-OMe-1-CE Phosphoramidite, 2'-OMe-5-Me-C-CE Phosphoramidite, Ac-C-CE Phosphoramidite, Ac-C-RNA 500, dmf-dG-CE Phosphoramidite, dmf-dG-CPG 500, 2-Amino-dA-CE Phosphoramidite, (M. P. Reddy, N. B. Hanna, and F. Farooqui, Tetrahedron Lett., 1994, 35, 4311-4314; B. P. Monia, et al., J. Biol. Chem., 1993, 268, 14514-14522).

Common Protecting Reagents in Organic Syntheses: (Dimethyl-t-butylsilyloxy)methyl chloride (SOMCI), Ethoxyethyl chloride (EECI), α-chloro ethers, o-Nitrobenzyloxymethyl chloride, b,b,b-Trichloroethoxymethyl chloride (TCEMCI), (−)-Menthyl ester, (P)-Benzyl ester, 1,1,1,3,3,3-Hexafluoro-2-phenyl-2-propyl ether, 1,1,3,3-Tetramethyl-1,3,2-disilazane, 1,2,4-Dithiazolidine-3,5-dione, 1,2-Dibromide, 1,2-Dichloride, 1,2-Diol mono-4-methoxybenzyl ether, 1,2-Diol mono-t-butyl ether, 1,2-Diol monoacetate ester, 1,2-Diol monoallyl ether, 1,2-Diol monobenzoate ester, 1,2-Diol monobenzyl ether, 1,2-Diol monotosylate, 1,3-Benzodithiolan, 1,3-Benzodithiolan-2-yl ether, 1,3-Diol mono-4-methoxybenzyl ether, 1,3-Diol monobenzoate ester, 1,3-Diol monobenzyl ether, 1,3-Dioxan, 1-(2-(Trimethoxysilyl) ethoxy)ethyl ether, 1-Adamantyl ester, 1-Benzoyl-1-propen-2-yl amine, 1-Ethoxyethyl ether, 1-Methoxyethylidene acetal, 1-Methyl-1-methoxyethyl ether, 1-Phenyl-3,5-di-t-butylcyclohexadien-4-onyl amine, 1-Phenylethyl ester, 2,2,2-Trichloroethoxymethyl ether, 2,2,2-Trichloroethyl carbonate, 2,2,2-Trichloroethyl ester, 2,2,2-Trichloroethyl phosphate, 2,2,5,7,8-Pentamethylchroman-6-sulphonamide, 2,2-Dimethyl-4-pentenoate ester, 2,3,6-Trimethyl-4-methoxybenzenesulphonamide, 2,4,6-Trimethylbenzenesulphonamide, 2,4-DNP hydrazone, 2,5-Dichlorophenyl phosphate, 2,5-Dimethylpyrrole, 2-(2-Methoxyethoxy)ethyl ester, 2-(4-Nitrophenyl)ethyl ether, 2-(4-Nitrophenyl)ethyl phosphate, 2-(4-Toluenesulphonyl)ethyl ester, 2-(Dibromomethyl)benzoate ester, 2-(Trimethylsilyl)ethyl carbonate, 2-(Trimethylsilyl)ethyl ester, 2-(Trimethylsilyl)ethyl ether, 2-Benzenesulphonylethyl thioether, 2-Bromoethyl ester, 2-Chloroethyl ester, 2-Chlorophenyl phosphate, 2-Cyanoethyl phosphate, 2-Methoxyethyl ester, 2-Nitrobenzenesulphenamide, 2-Nitrobenzenesulphonamide, 2-Oxazoline, 2-Phenylethyl ester, 2-Pyridyl disulphide, 2-Tetrahydropyranyl amine, 4-Chlorobenzoate ester, 4-Chlorobutyl ester, 4-Methoxybenzamide, 4-Methoxybenzoate ester, 4-Methoxybenzyl amine, 4-Methoxybenzyl ester, 4-Methoxybenzyloxymethyl ether, 4-Nitrobenzamide, 4-Nitrobenzoate ester, 4-Nitrobenzyl ester, 4-Nitrobenzyl ether, 4-Nitrobenzyl phosphate, 4-Nitrophenyl ester, 4-Nitrophenyl hydrazone, 4-Toluenesulphonamide, 4-Toluenesulphonate, 9-Fluorenylmethyl carbonate, 9-Fluorenylmethyl ester, Allyl carbonate, Allyl ester, Benzenesulphonamide, Benzenesulphonate, Benzyl carbonate, Benzyl ester, BOM ether, DMTr ether, MEM ether, Methanesulphonamide, Methanesulphonate, ethyl carbonate, MMTr ether, MOM carbonate, MOM ester, MOM ether, MTHP ether, MTM ester, MTM ether, N-4-Methoxybenzyl amide, N-4-Tolyl amide, N-Benzenesulphonyl amide, N-Benzyl imine, n-Butyl ester, n-Butyl ether, O-4-Methoxybenzyl carbamate, O-9-Fluorenylmethyl carbamate, Phenyl thioether, Phenyl thiolesterPiperidinamide, PMB ether, SEM ester, SEM ether, Succinate ester, t-Butyl carbonate, t-Butyl ester, t-Butyl ether, t-Butyl phosphate, t-Butyl thioether, t-Butyl thiolester, TBDMS ester, TBDMS ether, TBDPS ether, TES ether, THF ether, THP ether, TIPDS diether, TIPS ether, TMS ester, TMS ether, TMS thioether, Tosyl hydrazone, TPS ether, Trifluoroacetamide.

A list of commercially available protecting groups may be found in Sigma-Aldrich (2003) Catalog, the contents of which as it relates to the disclosure of protective groups is incorporated by reference herein in its entirety.

In general, in one aspect of the invention, the protecting groups used in the present invention may be those that are used in the sequential addition of one or more amino acids or suitably protected amino acids to a growing peptide chain. Normally, either the amino or carboxyl group of the first amino acid is protected by a suitable protecting group.

In a particularly preferred method the amino function is protected by an acid or base sensitive group. Such protecting groups should have the properties of being stable to the conditions of linkage formation, while being readily removable without destruction of the growing branched/linear polymer. Such suitable protecting groups may be without limitation 9-fluorenylmethyloxycarbonyl (Fmoc), t-butyloxycarbonyl (Boc), benzyloxycarbonyl (Cbz), biphenylisopropyl-oxycarbonyl, t-amyloxycarbonyl, isobornyloxycarbonyl, ($\alpha,\alpha$)-dimethyl-3,5-dimethoxybenzyloxycarbonyl, o-nitrophenylsulfenyl, 2-cyano-t-butyloxycarbonyl, and the like.

Particularly preferred protecting groups also include 2,2, 5,7,8-pentamethylchroman-6-sulfonyl (pmc), p-toluenesulfonyl, 4-methoxybenzenesulfonyl, adamantyloxycarbonyl, benzyl, o-bromobenzyloxycarbonyl, 2,6-dichlorobenzyl, isopropyl, t-butyl (t-Bu), cyclohexyl, cyclophenyl and acetyl (Ac), 1-butyl, benzyl and tetrahydropyranyl, benzyl, p-toluenesulfonyl and 2,4-dinitrophenyl.

In the addition method, the branched termini of the linear/branched polymer is attached to a suitable solid support. Suitable solid supports useful for the above synthesis are those materials which are inert to the reagents and reaction conditions of the stepwise condensation-deprotection reactions, as well as being insoluble in the media used.

The removal of a protecting group such as Fmoc from the linear tip of the branched/linear polymer may be accomplished by treatment with a secondary amine, preferably piperidine. The protected portion may be introduced in about 3-fold molar excess and the coupling may be preferably carried out in DMF. The coupling agent may be without limitation O-benzotriazol-1-yl-N,N,N',N'-tetramethyluronium-hexafluorophosphate (HBTU, 1 equiv.) and 1-hydroxybenzotriazole (HOBT, 1 equiv.).

The polymer may be deprotected, either in succession or in a single operation. Removal of the polypeptide and deprotection can be accomplished in a single operation by treating the substrate-bound polypeptide with a cleavage reagent, for example thianisole, water, ethanedithiol and trifluoroacetic acid.

Table 1 below lists various types of exemplified compounds. However, it is to be understood that variations in X, L, W, R and T are encompassed by the present invention.

TABLE 1

Representative and Exemplified Macromolecule Compounds

| Compound No. | X | L | W | R | T |
|---|---|---|---|---|---|
| 3-1 | A | NH—$(CH_2)_3C(O)$ | NH | $CH_2O(CH_2)_2C(O)$ | OH |
| 3-2 | A | NH—$(CH_2)_3C(O)$ | NH | $CH_2O(CH_2)_2C(O)$ | OMe |
| 3-3 | Boc | NH—$(CH_2)_3C(O)$ | NH | $CH_2O(CH_2)_2C(O)$ | OH |
| 3-4 | Boc | NH—$(CH_2)_3C(O)$ | NH | $CH_2O(CH_2)_2C(O)$ | OMe |
| 3-5 | A | NH—$(CH_2CH_2O)_2CH_2C(O)$ | NH | $CH_2O(CH_2)_2C(O)$ | OH |
| 3-6 | A | NH—$(CH_2CH_2O)_2CH_2C(O)$ | NH | $CH_2O(CH_2)_2C(O)$ | OMe |
| 6-1 | A | NH—$(CH_2)_3C(O)$ | NH | $CH_2O(CH_2)_2C(O)$ | OH |
| 6-2 | Boc | NH-(cyclohexyl)(CO) | $CH_2$ | $(CH2)_2$-(cyclohexyl)-C(O) | $NH_2$ |
| 6-3 | Boc | NH—$(CH_2CH_2O)_2CH_2C(O)$ | NH | $CH_2O(CH_2)_2C(O)$ | OH |
| 6-4 | Fmoc | NH—$(CH_2)_6NHC(O)$ | NH | $CH_2$—C≡C—$CH_2C(O)$ | OH |
| 6-5 | Fmoc | NH—$(CH_2)_7C(O)$ | O | $CH_2$—C≡C—$CH_2C(O)$ | OMe |
| 6-6 | NS | NH-(cyclohexyl)(CO) | O | $CH_2O(CH_2)_2C(O)$ | $NH_2$ |
| 6-7 | NS | NH—$(CH_2)_6NHC(O)$ | NH | $(CH2)_7$ | $NH_2$ |
| 8-1 | A | NH—$(CH_2)_3C(O)$ | NH | $CH_2O(CH_2)_2C(O)$ | OH |
| 8-2 | Boc | NH—$(CH_2)_7C(O)$ | NH | $(CH2)_2C(O)$ | OH |
| 8-3 | NS | NH—$(CH_2)_6(CO)$ | NH | $(CH2)_2$-(cyclohexyl)-C(O) | OH |
| 8-4 | Fmoc | NH—$(CH_2)_6(CO)$ | O | $CH_2$—C≡C—$CH_2C(O)$ | $NH_2$ |
| 8-5 | Fmoc | NH—$(CH_2)_6NH(CO)$ | O | $(CH2)_2$-(cyclohexyl)-C(O) | OH |
| 8-6 | NS | NH-(cyclohexyl)(CO) | O | $CH_2OCH(CH_3)CH_2C(O)$ | $NH_2$ |
| 8-7 | Boc | NH-(cyclopropyll)(CO) | O | $CH_2$—C≡C—$CH_2C(O)$ | $NH_2$ |
| 9-1 | A | NH—$(CH_2)_3C(O)$ | NH | $CH_2O(CH_2)_2C(O)$ | OH |
| 9-2 | A | NH—$(CH_2)_3C(O)$ | NH | $CH_2O(CH_2)_2C(O)$ | OMe |
| 9-3 | A | NH—$(CH_2CH_2O)_2CH_2C(O)$ | NH | $CH_2O(CH_2)_2C(O)$ | OH |
| 9-4 | A | NH—$(CH_2CH_2O)_2CH_2C(O)$ | NH | $CH_2O(CH_2)_2C(O)$ | OMe |

TABLE 1-continued

Representative and Exemplified Macromolecule Compounds

| Compound No. | X | L | W | R | T |
|---|---|---|---|---|---|
| 9-5 | Fmoc | NH—$(CH_2)_6C(O)$ | NH | $CH_2O(CH_2)_2C(O)$ | OH |
| 9-6 | Fmoc | NH—$(CH_2)_6C(O)$ | NH | $CH_2O(CH_2)_2C(O)$ | OMe |
| 9-7 | Boc | NH—$(CH_2)_3C(O)$ | NH | $CH_2O(CH_2)_2C(O)$ | OH |
| 9-8 | Boc | NH—$(CH_2)_3C(O)$ | NH | $CH_2O(CH_2)_2C(O)$ | OMe |
| 9-9 | Ns | NH—$(CH_2)_3C(O)$ | NH | $CH_2O(CH_2)_2C(O)$ | OH |
| 9-10 | Ns | NH—$(CH_2)_3C(O)$ | NH | $CH_2O(CH_2)_2C(O)$ | OMe |
| 9-11 | A | NH—$(CH_2)_6NHC(O)CH_2$ | $CH_2$ | $(CH2)_7$ | OBzl |
| 12-1 | A | NH—$(CH_2)_3C(O)$ | NH | $CH_2O(CH_2)_2C(O)$ | OH |
| 12-2 | Fmoc | NH—$(CH_2)_6NHC(O)$ | NH | $(CH_2)_2$-(cyclohexyl)-C(O) | $NH_2$ |
| 12-3 | Boc | NH-(cyclohexyl)(CO) | O | $CH_2$—C≡C—$CH_2C(O)$ | OMe |
| 12-4 | Boc | NH—$(CH_2)_5$ | NH | $CH_2OCH(CH_3)CH_2C(O)$ | $NH_2$ |
| 12-5 | NS | NH-(cyclopropyl)(CO) | $CH_2$ | $(CH2)_2$ | $NH_2$ |
| 12-6 | NS | NH—$(CH_2)_6C(O)$ | O | $CH_2OCH_2CH(CH_3)C(O)$ | $NH_2$ |
| 12-7 | Fmoc | NH—$(CH_2)_6NHC(O)$ | O | $CH_2OCH(CH_3)CH_2C(O)$ | $NH_2$ |
| 16-1 | Boc | NH—$(CH_2)_3C(O)$ | NH | $CH_2O(CH_2)_2C(O)$ | $NH_2$ |
| 16-2 | Boc | NH-(cyclohexyl)(CO) | $CH_2$ | $(CH2)_2$-(cyclohexyl)-C(O) | OH |
| 16-3 | Fmoc | NH—$(CH_2CH_2O)_2CH_2C(O)$ | O | $CH_2O(CH_2)_2C(O)$ | OH |
| 16-4 | Fmoc | NH—$(CH_2)_6NHC(O)$ | NH | $(CH_2)_2$-(cyclohexyl)-C(O) | $NH_2$ |
| 16-5 | NS | NH-(cyclohexyl)(CO) | NH | $CH_2$—C≡C—$CH_2C(O)$ | OH |
| 16-6 | NS | NH-(cyclopropyl)(CO) | $CH_2$ | $CH_2O(CH_2)_2C(O)$ | OMe |
| 16-7 | A | NH-(cyclopropyl)(CO) | $CH_2$ | $CH_2OCH(CH_3)CH_2C(O)$ | OH |
| 16-8 | A | NH-(cyclopropyl)(CO) | $CH_2$ | $CH_2OCH_2CH(CH_3)C(O)$ | $NH_2$ |
| 16-9 | A | NH—$(CH_2)_5$ | O | $CH_2OCH_2CH(CH_3)C(O)$ | OH |
| 18-1 | A | NH—$(CH_2)_3C(O)$ | NH | $CH_2O(CH_2)_2C(O)$ | OH |
| 18-2 | Fmoc | NH-(cyclohexyl)(CO) | O | $CH_2OCH(CH_3)CH_2C(O)$ | $NH_2$ |
| 18-3 | Boc | NH-(cyclopropyl)(CO) | O | $CH_2OCH_2CH(CH_3)C(O)$ | $NH_2$ |
| 18-4 | Fmoc | NH—$(CH_2)_6NHC(O)CH_2$ | NH | $(CH2)_2$-(cyclohexyl)-C(O) | OH |
| 18-5 | NS | NH—$(CH_2)_6NHC(O)$ | $CH_2$ | $CH_2$—C≡C—$CH_2C(O)$ | OMe |
| 18-6 | Boc | NH—$(CH_2)_5$ | O | $CH_2OCH_2CH(CH_3)C(O)$ | $NH_2$ |
| 27-1 | A | NH—$(CH_2)_3C(O)$ | NH | $CH_2O(CH_2)_2C(O)$ | OH |
| 27-2 | A | NH—$(CH_2)_6NHC(O)CH_2$ | $CH_2$ | $(CH2)_7$ | OH |
| 27-3 | Fmoc | NH—$(CH_2CH_2O)_2CH_2C(O)$ | O | $(CH2)_2$-(cyclohexyl)-C(O) | $NH_2$ |
| 27-4 | NS | NH-(cyclopropyl)(CO) | NH | $(CH2)_2$-(cyclohexyl)-C(O) | $NH_2$ |
| 27-5 | Boc | NH-(cyclohexyl)(CO) | $CH_2$ | $CH_2OCH(CH_3)CH_2C(O)$ | OMe |
| 27-6 | Fmoc | NH—$(CH_2)_5$ | O | $CH_2OCH_2CH(CH_3)C(O)$ | $NH_2$ |

Target-Specific Ligand or Probe

The target-specific ligand, also known as probe, which is to be attached to the linear end of the branched/linear polymer may include a variety of compounds, including chemicals, biochemicals, bioactive compounds and so on. In this regard, the ligand may be nucleic acid, oligonucleotide, RNA, DNA, PNA, or aptamer. The oligonucleotide may be a naturally occurring nucleic acid or an analog thereof. Thus, the ligand may be a polypeptide composed of naturally occurring amino acids or synthetic amino acids. The ligand may be a combination of nucleic acid, amino acid, carbohydrate or any other chemical so long as it is capable of being attached to the linear portion of the branched/linear polymer. In particular, the ligand may also be a chemical, such as based on a triazine backbone, which may be used as a component in a combinatorial chemistry library, in particular, a triazine tagged library.

Substrate

The substrate may be any solid surface to which the branched/linear polymer may bind through either covalent or ionic bond. The substrate may be functionalized so that binding may occur between the branched termini of the branched/linear polymer. The surface of the substrate may be a variety of surfaces according to the needs of the practitioner in the art. If a microarry or biochip format is desired then typically oxidized silicon wafer, fused silica or glass may be the substrate. Preferably, the substrate may be a glass slide. Other substrates may include membrane filters such as but not limited to nitrocellulose or nylon. The substrate may be hydrophilic or polar, and may possess negative or positive charge before or after coating.

Microarray

In order to improve the performance of DNA microarrays, issues such as probe design, reaction conditions during spotting, hybridization and washing conditions, suppression of non-specific binding, distance between the biomolecules and the surface, and the space between the immobilized biomolecules should be considered. Because most of these factors are associated with the nature of the microarray surface, surface optimization has become one of the major goals in microarray research. Whitesell and Chang showed that an alpha-helix formation of immobilized oligopeptides was encouraged on a space-controlled gold surface (Whitesell et al., Science 261, 73-76 (1993)). We now report that a surface modified with the cone-shaped dendron can provide DNA microarrays with single nucleotide polymorphism (or SNP) discrimination efficiency close to the solution value (1:0.01) while concurrently reducing DNA non-specific binding.

Figure 2:
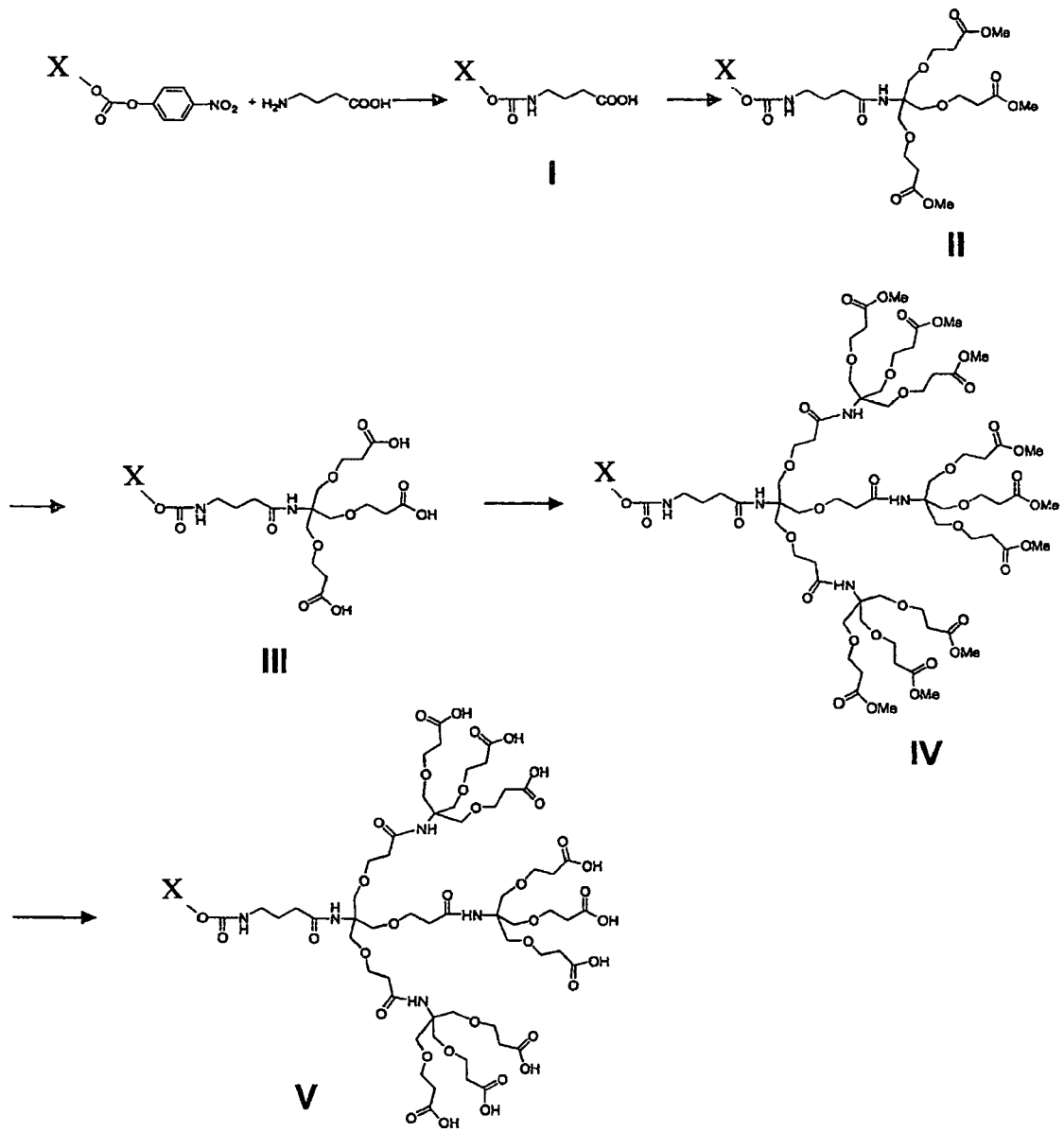
FIG. 2 shows a reaction scheme for producing a dendron. X represents a protecting group.
Figure 3:
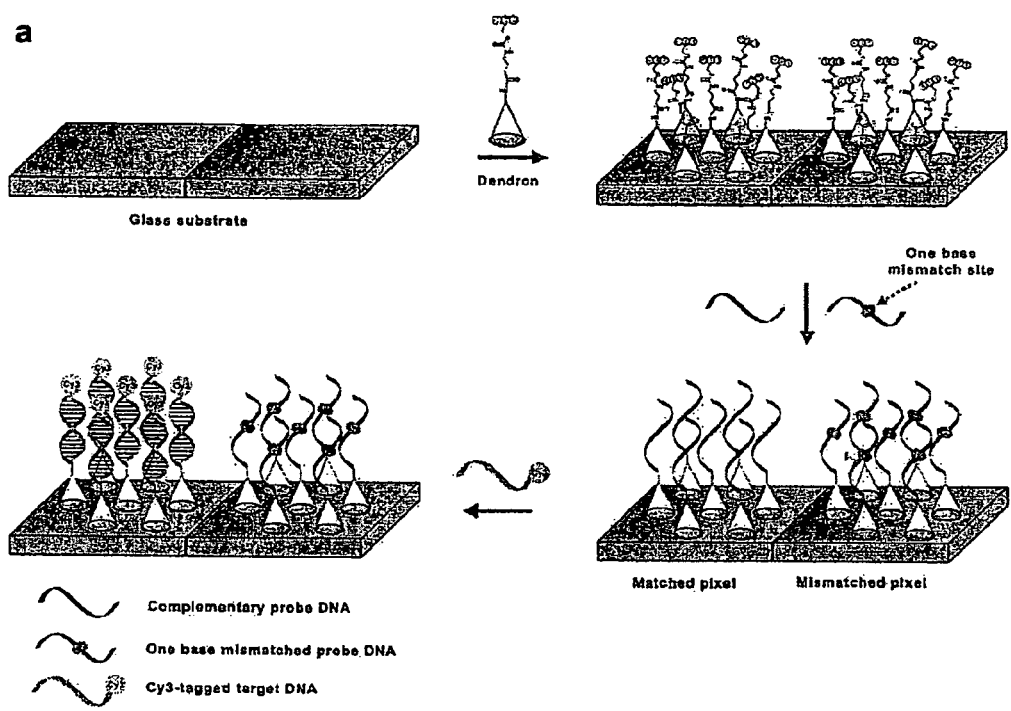
FIGS. 3a-3c show detection of a dendron-modified surface.

FIG. 2 is a scheme showing the synthesis of a dendron. Various starting material, intermediate compounds, and dendron compounds, wherein "X" may be any protecting group, including anthracenemethyl (A), Boc, Fmoc, Ns and so forth. FIG. 3(a) shows modification of glass surface with a dendron (FIG. 3b) and selective hybridization of a fluorophore-tagged target oligonucleotide with a matched oligonucleotide probe while discriminating effectively a single base mismatched pair out on the dendron-modified surface.

A second generation branch dendron having surface reactive functional groups at the branch termini may be used, which self assembles and provides appropriate space between them. Previous studies showed that multiple ionic attractions between cations on a glass substrate and anionic carboxylates at the dendron's termini successfully generated a well-behaved monolayer, and guaranteed an inter-ligand space over 24 Å (Hong et al., Langmuir 19, 2357-2365 (2003)). To facilitate deprotection and increase the deprotected apex amine's reactivity, we modified the structure as in FIG. 3b. We also observed that covalent bond formation between the dendron's carboxylic acid groups and the surface hydroxyl groups is as effective as the ionic attraction, while also providing enhanced thermal stability. Moreover, an oligoetheral interlayer was effective for suppressing non-specific oligonucleotide binding.

Figure 4:
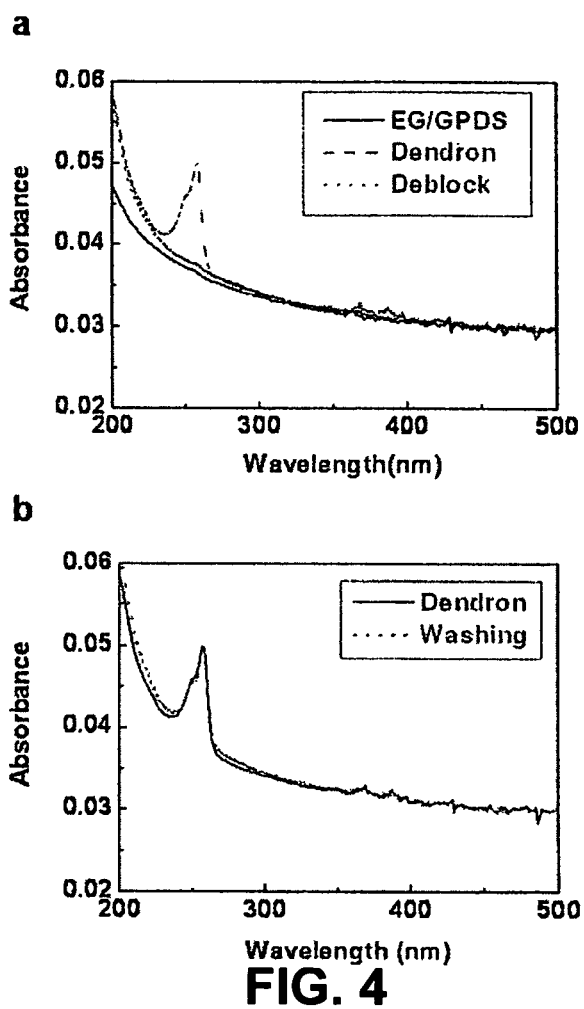
FIGS. 4a-4b show UV spectroscopic analysis. (a) shows UV spectrum after each reaction step. EG/GPDS and Dendron signify spectra acquired before and after the introduction of the dendron on the ethylene glycol-modified substrate, and Deblock corresponds to the spectrum after the deprotection step. (b) shows stability test. A spectrum obtained after stirring in DMF at room temperature for 1 d is signified by "Washing".
Figure 5:
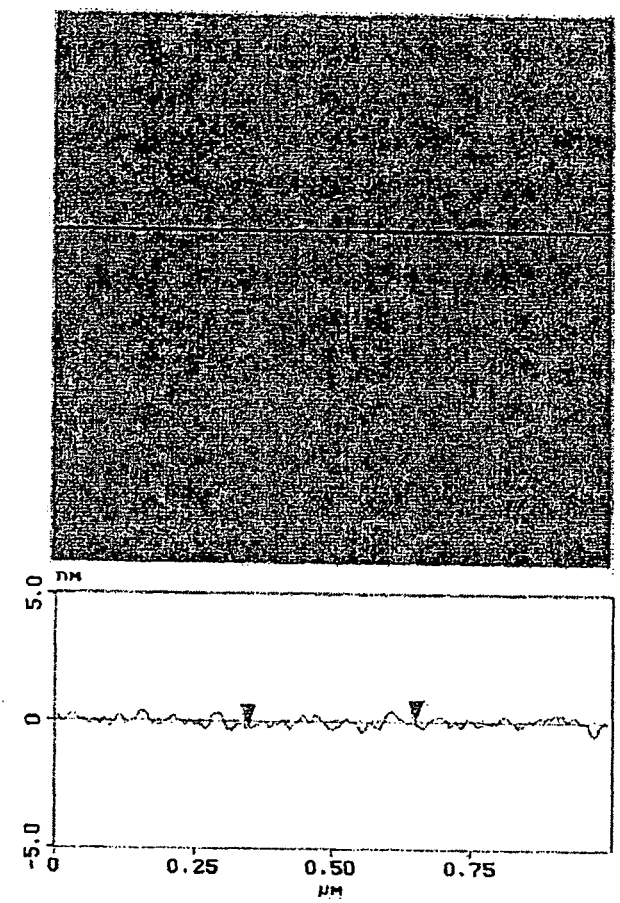
FIG. 5 shows tapping mode atomic force microscopy (AFM) image of the dendron-modified surface. A Nanoscope IIIa AFM (Digital Instruments) equipped with an "E" type scanner was employed. The scanned area is $1.0 \times 1.0 \ \mu m^2$.

The hydroxylated substrate was prepared by using a previously reported method (Maskis et al., Nucleic Acids Res. 20, 1679-1684 (1992)). Substrates including oxidized silicon wafer, fused silica, and glass slide, were modified with (3-glycidoxypropyl)methyldiethoxysilane (GPDES) and ethylene glycol (EG). The dendron was introduced to the above substrates through a coupling reaction between the dendron's carboxylic acid group and the substrate's hydroxyl group using 1-[3-(dimethylamino)propyl]-3-ethylcarbodiimide hydrochloride (EDC) or 1,3-dicyclohexylcarbodiimide (DCC) in the presence of 4-dimethylaminopyridine (DMAP) (Boden et al., J. Org. Chem. 50, 2394-2395 (1985); Dhaon et al., J. Org. Chem. 47, 1962-1965 (1982)). The increase in thickness after the dendron introduction was 11±2 Å, which was comparable to the previous value observed for the ionic bonding (Hong et al., Langmuir 19, 2357-2365 (2003)). After the immobilization, an absorption peak arising from the anthracene moiety of the dendron was observed at 257 nm. The molecular layer is stable enough to show no change in terms of thickness and absorption characteristics upon stirring in dimethylformamide for 1 d (FIG. 4). The topographical images obtained by tapping mode atomic force microscope (AFM) also showed that the resulting layer was very smooth and homogeneous without any aggregates or holes (FIG. 5).

To be ready for DNA microarrays, the immobilized dendron was activated to generate a primary amine group through deprotection process. After the deprotection in 1.0 M trifluoroacetic acid (TFA) (Kornblum et al., J. Org. Chem. 42, 399-400 (1977), the absorption peak at 257 nm disappeared without any other detrimental change of the surface properties (FIG. 4a). This observation demonstrated that the protecting group was removed successfully without chemically damaging the layer while thickness was slightly decreased due to the elimination of the protecting group.

After modification with di(N-succinimidyl)carbonate (DSC) according to a previously established method (Beier et al., Nucleic Acids Res. 27, 1970-1977 (1999)), probe oligonucleotides were immobilized onto the activated surface of glass slide by spotting 50 mM sodium bicarbonate buffer (10% dimethylsulfoxide (DMSO), pH, 8.5) solution of the appropriate amine-tethered oligonucleotide (20 µM) using a Microsys 5100 Microarrayer (Cartesian Technologies, Inc.) in a class 10,000 clean room. Typically, for substrates with a reactive amine surface group, a thiol-tethered oligonucleotide and a heterobifunctional linker such as succinimidyl 4-maleimido butyrate (SMB) or sulphosuccinimidyl-4-(N-maleimidomethyl)cyclohexane-1-carboxylate (SSMCC) are employed (Oh et al., Langmuir 18, 1764-1769 (2002); Frutos et al., Langmuir 16, 2192-2197 (2000)). In contrast, because the dendron-modified surface guarantees a certain distance among the amine functional groups, use of homobifunctional linkers such as DSC is not problematic. As a result, an amine-tethered oligonucleotide can be utilized for spotting. Apart from the cost effectiveness, use of easily oxidized thiol-tethered oligonucleotide can be avoided, although it is possible that such thiol-tethered oligonucleotides may be useful under certain conditions.

The DNA microarrays were fabricated to evaluate the discrimination efficiency between a complementary pair (A:T) and three internal single-base mismatched pairs (T:T, G:T, C:T). After spotting the probe oligonucleotides side by side in a 4 by 4 format, the microarray was incubated in a humidity chamber (80% humidity) for 12 h to give the amine-tethered DNA sufficient reaction time. Slides were then stirred in a buffer solution (2×SSPE buffer (pH, 7.4) containing 7.0 mM sodium dodecylsulfate) at 37° C. for 3 h and in boiling water for 5 min to remove the non-specifically bound oligonucleotides. Finally, the DNA-functionalized microarray was dried under a stream of nitrogen for the next step. For a fair comparison, different kinds of probes were spotted in a single plate.

For hybridization, a 15-base oligonucleotide (Target 1) or 45-base oligonucleotide (Target 2) was used (FIG. 3c). Hybridization was performed in the above washing buffer solution containing a target oligonucleotide (1.0 nM) tagged with a Cy3 fluorescent dye at 50° C. for 1 h using a GeneTAC™ HybStation (Genomic Solution, Inc.). The microarray was rinsed with buffer solution at 37° C. four times for 1 min in order to remove excess target oligonucleotide and dried with nitrogen. The fluoresecence signal on each spot was measured with a ScanArray Lite (GSI Lumonics) and analyzed by Imagene 4.0 (Biodiscovery).

Figure 6:
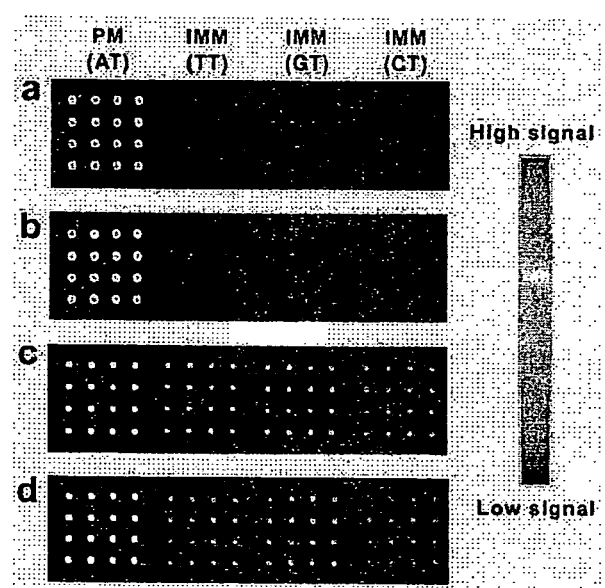
FIGS. 6a-6d show fluorescence images after hybridization. 6a-6b show images obtained after the hybridization between (a) probe 1 and target 1 or (b) probe 1 and target 2 on the dendron-modified surface. 6c-6d show images recorded after the hybridization between (c) target 1 and probe 1 or (d) target 1 and probe 2 on an APDES-modified surface.

In the case of the 15-base target oligonucleotide, the image shows that there is a dramatic difference in the intensity between the matched and the internal mismatched pairs (FIG. 6a). The normalized fluorescence signal ratios (or intensity ratios for one base internal-mismatched pair versus the perfectly matched pair, i.e., MM/PM) were 0.005, 0.008, and 0.006 (T:T, G:T, and C:T internal mismatches) (FIG. 6a and Table 2). The observed selectivity is significantly improved over conventional methods, and a large increase of the selectivity (20~82 times) is recorded in comparison with DNA microarrays on the generic surface (Table 2). Previously, we also observed a selectivity factor of 1:0.19-0.57 for microarrays fabricated on various amine surfaces including a mixed self-assembled monolayer (i.e., mixed SAM)(Oh et al., Langmuir 18, 1764-1769 (2002)). In addition, other investigators improved the performance of DNA microarrays by modifying their surface and inventing better detection process, but none has reached this significantly improved ratio as far as a fluorescence detection method is concerned (Zhao et al., J. Am. Chem. Soc. 125, 12531-12540 (2003); Chakrabarti et al., J. Am. Chem. Soc. 125, 12531-12540 (2003); Benters et al., Nucleic Acids Res. 30, e10 (2002); Guschin et al., Analytical Biochemistry 250, 203-211 (1997); Taton et al., Science 289, 1757-1760 (2000); Wang et al., Nucleic Acids Res. 30, e61 (2002)). For example, successful discrimination ratio of 1:0.07 was reported for a three component hybridization/detection system (capture/target/probe)(Zhao et al., J. Am. Chem. Soc. 125, 12531-12540 (2003)). Even when peptide nucleic acids (PNAs) capable of increasing the selectivity were used, the selectivity on gold thin film and gold nanoparticle were 1:0.14 and 1:0.07, respectively (Chakrabarti et al., J. Am. Chem. Soc. 125, 12531-12540 (2003)).

TABLE 2

| | Normalized fluorescence signal ratio | | | |
|---|---|---|---|---|
| | Matched (A:T) | Mismatched (T:T) | Mismatched (G:T) | Mismatched (C:T) |
| Dendron-modified surface, 15-mer (Target 1 & Probe 1) | 1 | 0.005 | 0.008 | 0.006 |
| Dendron-modified surface, 45-mer (Target 2 & Probe 1) | 1 | 0.006 | 0.009 | 0.009 |
| APDES-modified surface, $C_6$ spacer (Target 1 & Probe 1) | 1 | 0.41 | 0.38 | 0.26 |
| APDES-modified surface, $(T)_{30}$ spacer (Target 1 & Probe 2) | 1 | 0.17 | 0.18 | 0.12 |

To simulate a more realistic system, a 45-base target oligonucleotide was employed. The MM/PM ratios for T:T, G:T, and C:T internal mismatches were 0.006, 0.009, and 0.009 (FIG. 6b and Table 2). This result shows that outstanding selectivity holds for the longer target oligonucleotides. It is believed that the efficacy of this DNA microarray should be attributed to the peculiarity of the dendron-modified surface, mesospacing between immobilized DNA strands.

Figure 7:
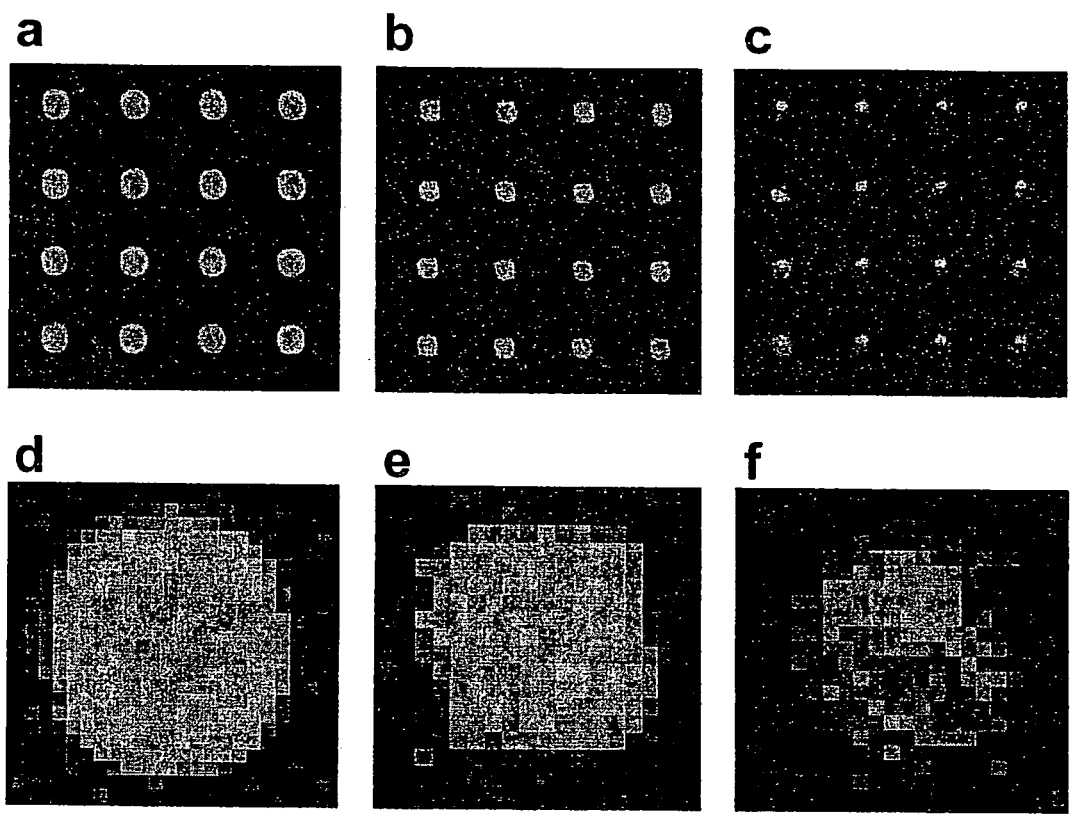
FIGS. 7a-7f show differences in intensity between matched and the internally mismatched pairs of oligonucleotides. Upper images (a-c) are 4×4 array fluorescence images and lower images (d-f) show one spot sampled from the 16 spots. (a) and (d) are for a dendron-modified microarray with DSC linker, (b) and (e) for an APDES-modified microarray with PDITC linker, and (c) and (f) for an APDES-modified microarray with DSC linker. Fluorescence images for a dendron-modified microarray with DSC linker and a APDES-modified microarray with PDITC linker show less than 10% coefficient variance (CV) value and homogeneous fluorescence signal in a single spot. On the other side, fluorescence images for an APDES-modified microarray with DSC linker show much smaller spot size, over 20% CV value, and non-uniform fluorescence signal in a single spot. Each pixel size is $10 \times 10 \ \mu m^2$.

For comparison, a DNA microarray was fabricated on the substrate modified with (3-aminopropyl)diethoxymethylsilane (APDES)(Oh et al., Langmuir 18, 1764-1769 (2002)), which is a typical substrate for DNA or protein microarrays. Its selectivity was tested using the same procedure and oligonucleotides as those for the dendron-modified DNA microarray, except for the use of 1,4-phenylenediisothiocyanate (PDITC) linker. Amine-tethered oligonucleotides were employed as described by Guo (Guo et al., Nucleic Acids Res. 22, 2121-2125 (1994)). The observed MM/PM ratios for T:T, G:T, and C:T cases were 0.41, 0.38, and 0.26 (FIG. 6c and Table 2). Use of DSC linker on the APDES-modified substrate resulted in high coefficient variance (CV) value (>20%), which represents the degree of variation among the spots, and non-uniform fluorescence intensity within each spot. On the other hand, PDITC linker assured better coefficient variance (CV) value (<15%) and homogeneous fluorescence intensity within a single spot like those of the dendron-modified substrate with DSC linker (FIG. 7).

For additional comparison, probe 2 oligonucleotides having an extra $(T)_{30}$ spacer at the 5' end of oligomer were utilized for SNP discrimination test. For this case, the probe with the extra spacer was immobilized on an APDES-modified surface. The observed MM/PM ratios for T:T, G:T, and C:T cases were 0.17, 0.18, and 0.12 (FIG. 6d and Table 2). The selectivity was significantly enhanced in comparison with the case of probe DNA with a $C_6$ spacer, but still was largely inferior to the dendron-modified DNA microarray.

Hybridization on the surface poses various complications, hurdles to control and predict the microarray's screening performance precisely. Non-specific binding, steric and electrostatic effects, and environmental changes during the washing process should be considered in addition to the melting temperature (Tm) of the duplex and the Gibbs free energy for the duplex formation. Difference between the Gibbs free energy of the internal-mismatched pairs (T:T, G:T, and C:T internal mismatches of the 15-mer) and that of the perfectly matched pair in solution is 2.67, 1.75, and 3.05 kcal/mol at 50° C. Gibbs free energy was calculated with $H_yT_{HER}$™ Software (http://ozone2.chem.wayne.edu). Therefore, the theoretical fluorescence ratios (MM/PM) are 0.016, 0.065, and 0.009 respectively. Also, study in solution phase with a molecular beacon showed that SNP discrimination ratio was as low as 1:0.01 (Taton et al., Science 289, 1757-1760 (2000)). These data strongly demonstrate that our dendron-modified DNA microarray represents an ideal case that reaches or even surpasses the thermodynamic limit. In particular, for the G:T case, the discrimination efficiency in the microarray format is better than the value calculated for the solution phase. The answer to which factors are main reasons for the selectivity increase is yet to be investigated, but washing stringency may play a role.

p53 SNP Detection

In biological systems, the p53 tumor-suppressor gene plays key roles in cell regulation, gene transcription, genomic stability, DNA repair, and apoptosis (see Velculescu et al, 1996, Clin. Chem., 42: 858-868, Harris et al, 1996, 88: 1442-1455, Sidransky et al, Annu, Rev. Med., 1996, 47: 285-301). It has been reported that loss of wild-type function of p53 can lead to cancer and p53 mutations are the most frequent genetic changes in human cancer such as colon, and lung cancer (Greenblatt, 1994, 54: 4855-4878).

Figure 8A:
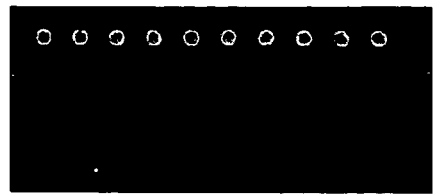
FIGS. 8a-8b show fluorescence images after hybridization of p53 specific oligonucleotide probe to target DNA sample for detection of single mutation in p53 using (a) [9]-acid dendron; and (b) [27]-acid dendron.

DNA microarrays on [9]-acid dendron modified substrates were applied to the detection of single mutation of p53 tumor suppressor gene in cancer cell line. Target DNA samples (~200-400 bases) which contain 175 codon were prepared by random priming the genomic DNA templates and allowed to hybridize with dendron-modified substrates on which 18 mer probe oligonucleotides had been immobilized in a 10 by 1 format. The MM/PM ratio for A:C, T:C, and C:C internal mismatches were 0.028, 0.031, and 0.007 (FIG. 8a). This result shows that the outstanding selectivity holds for real target DNAs.

Figure 8B:

The DNA microarrays on [27]-acid dendron modified substrates were prepared using the same method as in the case of [9]-acid dendron which is described above and applied to the detection of single mutation of 175 codon of p53 tumor suppressor gene. The MM/PM ratio for A:C, T:C, and C:C internal mismatches were 0.066, 0.01, and 0.005 (FIG. 8b). This result indicates that the DNA microarrays on [27]-acid dendron modified substrates also show outstanding selectivity for the detection of single mutation of real target DNAs.

Detection of 7 hot spot mutations of p53 gene using single dendron-modified surface.

Figure 9:
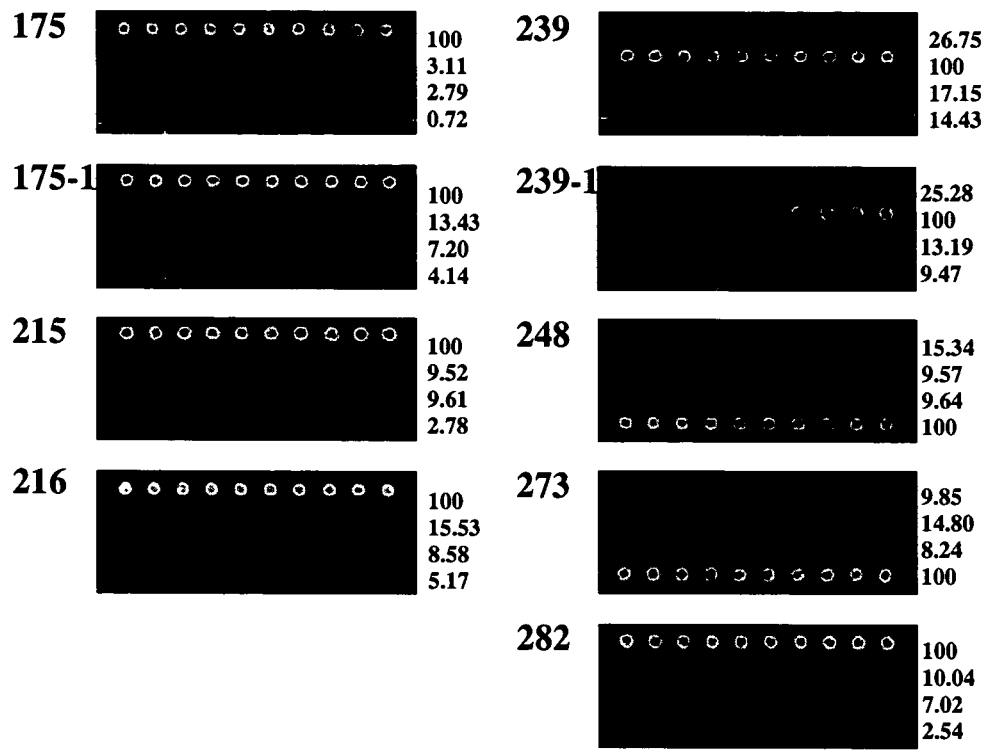
FIGS. 9a-9b show simultaneous detection of 7 hotspots of p53 Gene.
Figure 9:
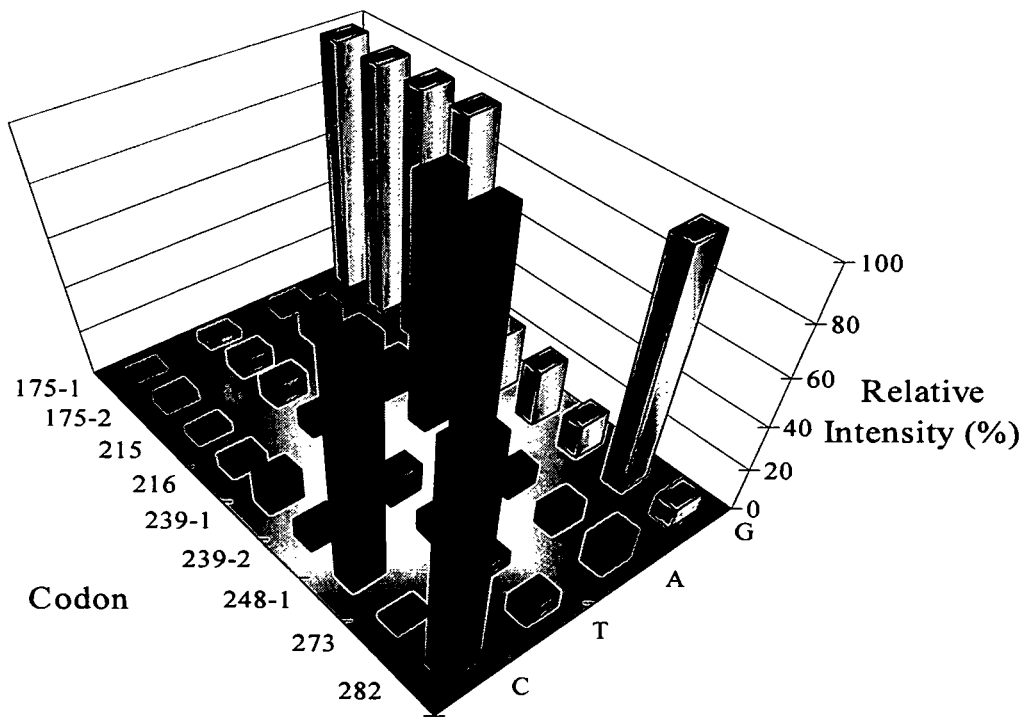

The dendron-modified substrates were applied to the detection of single mutation of p53 tumor suppressor gene in cancer cell line. Target DNA samples (200-400 mer) which span 7 hot spot codons (175, 215, 216, 239, 248, 273, and 282) were amplified from the DNA extracted from cancer cells by random priming and allowed to hybridize with capture probes (oligonucleotides of 15~25 mer) corresponding to 7 hot spot codons that had been immobilized (FIGS. 9a and 9b). Excellent SNP discrimination efficiency was obtained.

We fabricated successfully DNA microarray of the highest fidelity by providing mesospacing among the probe DNA, and found that SNP discrimination efficiency could be enhanced to reach or even surpass the solution value. The observed discrimination efficiency will make this methodology widely acceptable for very reliable high throughput gene diagnosis. It is expected that this strategy can be applied to various bioassays utilizing immobilized biomolecules.

Controlled Pore Glass Bead

Natural polymers such as dextran and agarose are the most frequently used chromatography supports for affinity chromatography. Sepharose 6B, 4B, and 2B are chromatographic materials composed of cross-linked agarose, which exhibit extremely low nonspecific adsorption. In spite of their wide use, agarose gel, typically in a bead shape, suffers some drawbacks. For instance, the flow (or elution) rates are moderate due to their soft nature, they cannot be dried or frozen since they shrink severely and essentially irreversibly, and they do not tolerate some organic solvents (Cuatrecasas, P. *J. Biol. Chem.* 1970, 245, 3059-3065; Kim et al., *Biochemistry* 2002, 41, 3414-3421). In comparison, controlled pore glass (CPG) exhibits many exceptional properties for the support: 1) it is mechanically stable, 2) it has a fixed three dimensional structure; it does not swell or shrink upon change of environment, 3) it is chemically stable from pH 1 to pH, 14, 4) it is inert to a broad range of nucleophilic and electrophilic reagents, 4) it is stable against heating, 5) it exhibits excellent flow (or elution) properties, 6) it shows less tendency to adhere to surface of containers. In addition, after a modification step, removal of reagents and byproducts through washing is rapid and efficient. All of these characteristics support potential usefulness in many fields such as permeation chromatography, solid phase synthesis, affinity purification, and so on.

Pore size: Effective porosity of CPG toward an adsorbed molecule is determined by the accessibility of the guest to the host surface. To a first approximation, the accessibility of CPG to a guest depends on geometric factors, which are related to the relative size of the pores of the host compared to the size of the guest. If a guest has a molecular size that is larger than the pore openings leading to the internal surface, adsorption and interactions can only occur with the external surface, which is much smaller than the internal surface area of the investigated porous materials (Poschalko et al., *J. Am. Chem. Soc.* 2003, 125, 13415-13426; Ottaviani et al., *J. Phys. Chem. B.* 2003, 107, 2046-2053). From these considerations, the extent and strength of adsorption of a guest onto CPG is expected to depend on the following parameters: pore size of CPG, the total surface area of the host, and the chemical composition of accessible surface of the host. In our investigation, three kinds of GST fused protein (GST (28 kDa), GST-PX$^{P47}$ (41 kDa), and GST-Munc18 fragment (98 kDa)) were employed. Molecular dimension of GST-Munc 18 should be similar to that of a fused GST of 100 kDa, GST-DREF (140×140×93 Å$^3$) (Hirose et al., *J. Biol. Chem.* 1996, 271, 3930-3937; Zhan et al., *Gene* 2001, 218, 1-9). To achieve the balance between pore size and surface area, porosity of the support has to be optimized for each specific protein. Because it is known that CPG with a pore size of approximately 50 nm allows the inclusion of complexes of the complete range of molecular subunits normally found in proteins our investigation had been carried out with 50 nm CPG. Simultaneously, use of CPG with a larger pore (300 nm) confirmed the effectiveness of the former CPG as far as the above proteins are concerned (Collins et al., *Anal. Biochem.* 1973, 54, 47-53; Haller, W. *J. Chromatogr.* 1973, 85, 129-131).

Figure 10:
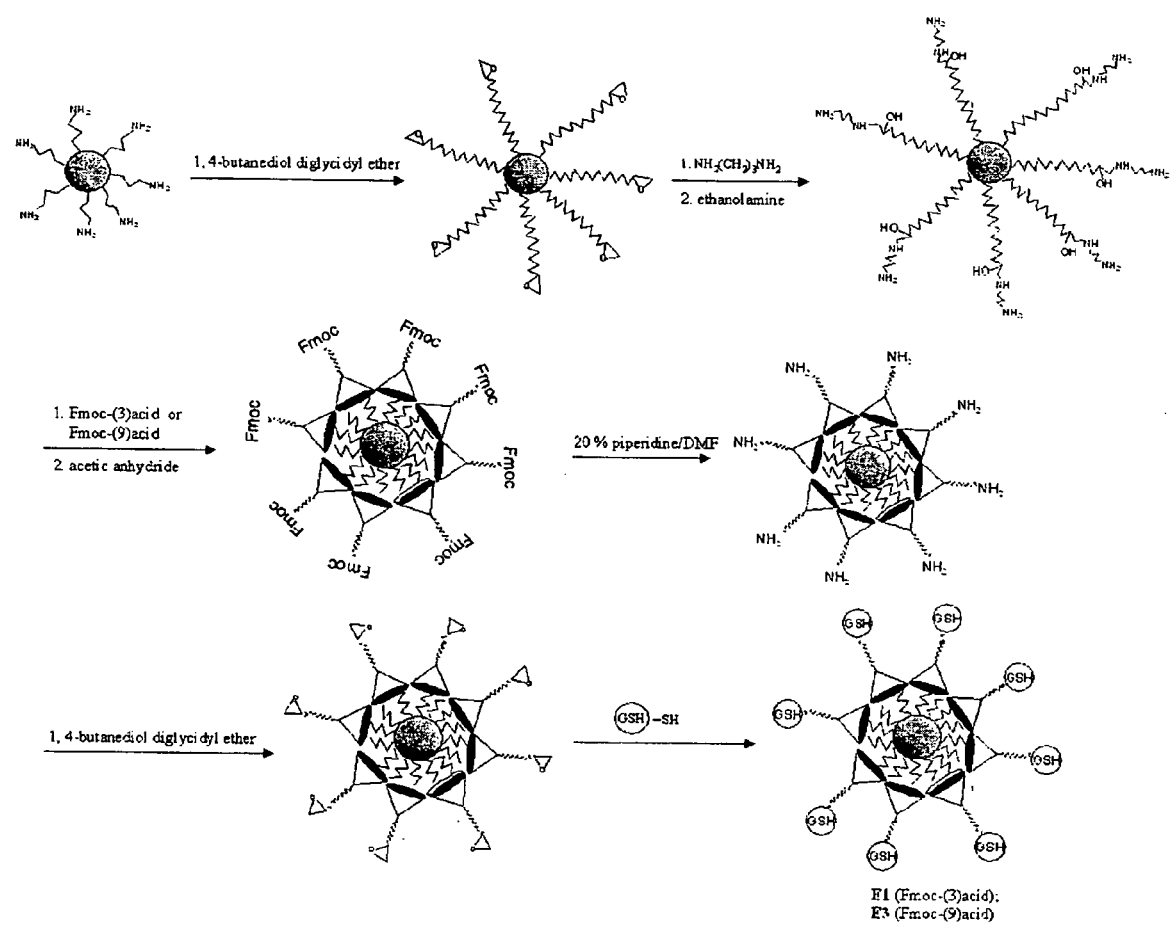
FIG. 10 shows a schematic presentation of sample E1 (Fmoc-(3)acid) and E3 (Fmoc-(9)acid) preparation with the dendrons on AMPCPG matrices, deprotection of Fmoc group by 20% piperidine in DMF and the incorporation of glutathione.

Modification of Glutathione CPG (Sample E1, E3, A, CS, and CL): A key concern of affinity matrices is degree of nonspecific binding (or NSB). It is a ubiquitous problem in affinity purification and solid-phase synthesis. In general, key factors to suppress nonspecific binding are to avoid the hydrogen bond donor groups and increase the hydrophilicity of matrices (Sigal et al, *J. Am. Chem. Soc.* 1998, 120, 3464-3473; Chapman et al., *Langmuir* 2000, 16, 6927-6936; Chapman et al., *J. Am. Chem. Soc.* 2000, 122, 8303-8304; Holmlin et al., *Langmuir* 2001, 17, 2841-2850; Ostuni et al., *Langmuir* 2001, 17, 6336-6343; Chapman et al., *Langmuir* 2001, 17, 1225-1233; Ostuni et al., *Langmuir* 2001, 17, 5605-5620). CPG surface, even when modified with an aminoalkyl group, is polar and retains partial negative charge (Hudson, D. *J. Comb. Chem.* 1999, 1, 403-457). Use of a diepoxide as a spacer had been reported to be responsible for the hydrophilic character of the matrix and the minimal nonspecific binding (Suen et al., *Ind. Eng. Chem. Res.* 2000, 39, 478-487; Sundberg et al., *J. Chromatogr. B.* 1974, 90, 87-98; Shimizu et al., *Nature Biotechnology* 2000, 18, 877-881). Therefore, 1,4-butanediol diglycidyl ether (or BUDGE) was employed for the modification leading to sample E1 and E3. The key features of the incorporation of BUDGE include generation of very stable ethereal bond against hydrolysis, the enhanced flexibility through a long spacer arm, full distance from the surface, and suppression of nonspecific binding to a certain extent. The last advantage can be explained by resembled structural motif with that of polyethylene glycol. Diepoxides can be utilized to link a molecule and a surface having a nucleophile, such as amine and thiol. During the ring opening process, stable carbon-heteroatom bond is generated as well as a β-hydroxy group. Use of the linker before and after dendron modification guarantees flexibility of the tethered GSH. The summarized modification steps are outlined in FIG. 10. For incorporation of the dendrons on the matrices, common reagents called EDC and NHS were used. After modification with the dendrons, acetic anhydride was introduced into system to cap the remained amine functionality. Finally, matrices were treated by 20% piperidine for 30 min to deblock the Fmoc group of the dendrons for the further modification. After elongation with BUDGE one more time, GSH was immobilized by utilizing reaction between the thiol and the epoxide.

As a control, sample A was prepared. Sequential modification with BUDGE, 1,3-diaminopropane, and BUDGE gave surface materials that is exactly same as E1 and E3 except absence of the dendrons. As before, GSH was immobilized by ring opening reaction between the epoxide and the thiol. Other control beads (Sample CL and CS) were prepared by using a heterobifunctional linker called GMBS to link GSH and AMCPG or LCAA-CPG. While, AMPCPG has a short arm consisting C3 hydrocarbon at the surface, LCAA-CPG has a long arm of C15 aliphatic chain. After amide formation with GMBS was allowed, the beads were treated with GSH. Addition of thiol group into maleimido group generated a covalent bond between carbon and sulfur atoms. The two-step treatment produced GSH immobilized controlled pore glass beads, i.e. CS and CL, with covalent bonds.

Ligand Density Measurement: Due to the difficulties in measuring the amount of immobilized glutathione directly, an indirect method that the ligand density was determined by measuring amount of dibenzofulvene released during the deprotection step was employed. 9-Fluorenylmethoxycarbonyl (Fmoc) protecting group at the apex of the dendrons is stable against acids but is readily cleaved by a variety of bases. In this study 20% piperidine in DMF is employed to deprotect the Fmoc functional group. Piperidine forms an adduct with the dibenzofulvene, and the adduct absorbs at 301 nm (Øye et al., *J. Phys. Chem. B.* 2003, 107, 3496-3499). On the other hand, when the absorbance of the collected solution appeared at 301 nm during the deprotection step with 20% piperidine, it indicated that the deprotection proceeded as intended.

Ligand density obtained with this method is 8.3 µmol/g for E1, 5.6 µmol/g for E3. The density is reduced by a factor of 11.1 upon modification with F-moc(3)acid and the value is further reduced by a factor of 1.5 upon use of a larger dendron. Thus, in a specific embodiment of the invention, smaller dendrons were more effective at obtaining higher density than using larger dendrons.

Figure 11:
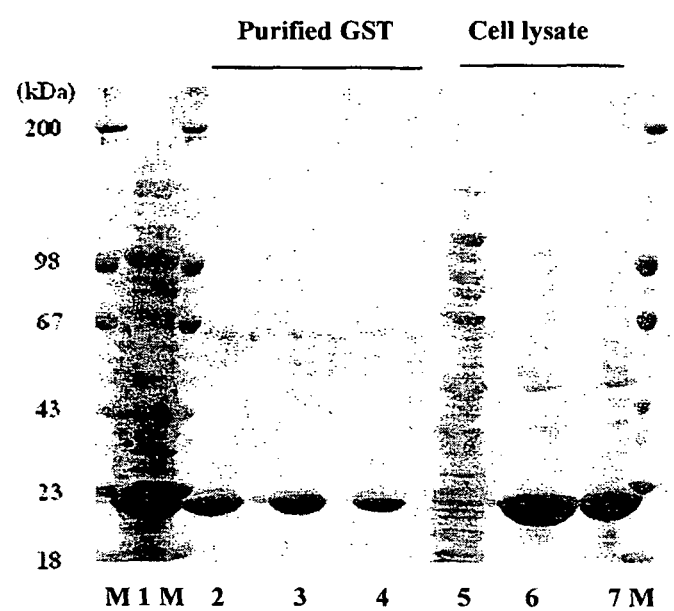
FIG. 11 shows binding of purified GST and GST lysate using three types of beads. M: markers. For comparison, GST lysate is run directly (lane 1). As controls, binding of the purified GST was tested for the matrices (A, E1, and E3) (lane 2, 3, 4). Finally, binding of cell lysate was examined to investigate efficiency of the matrices (A, E1, and E3) (lane 5, 6, 7).

GST Binding Assay: Binding characteristics of sample A, E1, and E3 were examined using purified GST and cell lysate (lane 2, 3, and 4 in FIG. 11). Lane 1 shows successful preparation of lysate. It is evident that the three matrices bind purified GST effectively. When cell lysate was introduced into the beads (lane 5, 6, and 7), a significant difference was observed between A and E1 or E3. For sample A, in spite of incorporation of BUDGE linkers, serious nonspecific binding was observed. Interestingly, when the dendrons were introduced on the matrix, nonspecific protein binding was effectively suppressed. It is noteworthy that self-assembly of either the dendron of the first generation or the one of the second generation effectively suppresses nonspecific binding of the solid support, while an extended spacer between the dendron and GSH retains the activity of the tethered tripeptide.

Figure 12:
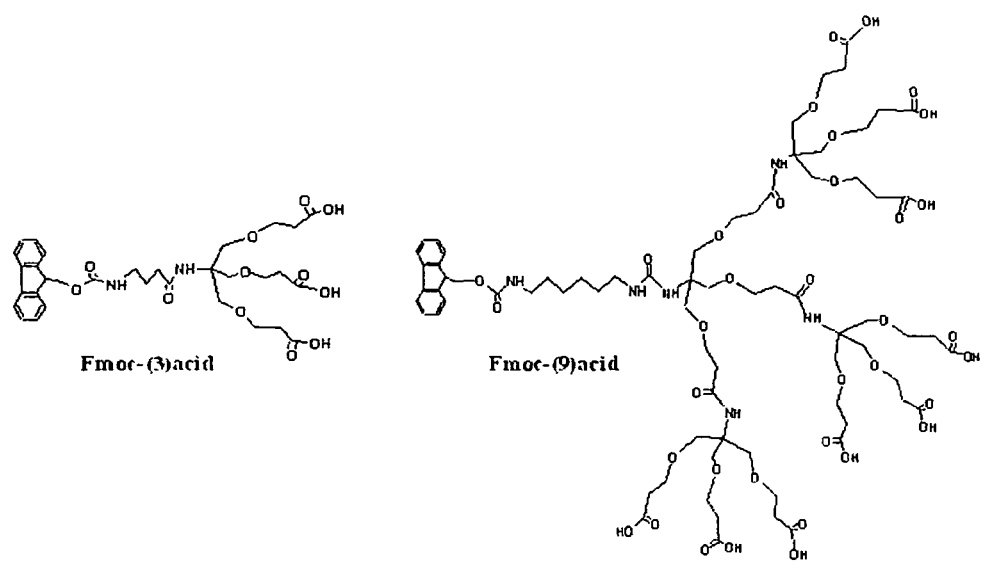
FIG. 12 shows a protected first generation functionalized dendron (E1, Fmoc-(3)acid), and a protected second generation functionalized dendron (E3, Fmoc-(9)acid).

In FIG. 12, in one aspect of the invention, etheral and amide groups constitute the main backbone of the structure, and immobilization of the dendrons generates again amide bonds. Also, high coverage of the dendrons is also an important factor for the success.

The ligand density for E1 is 1.48 times higher than that for E3. In other words, 148% of the ligand concentration was recorded for E1 (Table 3). In order to examine the binding efficiency of both beads, the weight of the samples was adjusted to have the same number of GSH in each sample. Densitometer showed that the ligand utilization for both cases was quite close (29%, 31%). The larger spacing of E3 does not enhance the binding efficiency of GST, probably because the examined protein is larger than the spacing of both E1 and E3 anyway.

TABLE 3

Ligand concentration and ligand utilization of sample E1 and E3.

| Samples | Ligand density (µmol/g) | Ratio of the ligand concentration (%) | Percentage of ligand utilization (%) |
|---|---|---|---|
| E1 | 8.3 | 148 | 29 |
| E3 | 5.6 | 100 | 31 |

Control experiment: We found that density of GSH was 14.5 µmol/g for CS, 11.9 µmol/g for CL. To compare efficacy of the beads in terms of specific binding of GST, captured proteins with CS (5.7 mg) and CL (7.0 mg) beads were analyzed along with samples from E1 (10.0 mg) and E3 (14.8 mg) beads. The utilized quantity was adjusted to have the same number of the GSH roughly. It is evident in the chromatogram (FIG. 13) CS and CL beads display poor selectivity as well as low binding capacity. The result stresses again importance of the dendron to guarantee not only improved accessibility of GST towards immobilized GSH but effective suppression of nonspecific binding.

Figure 14:
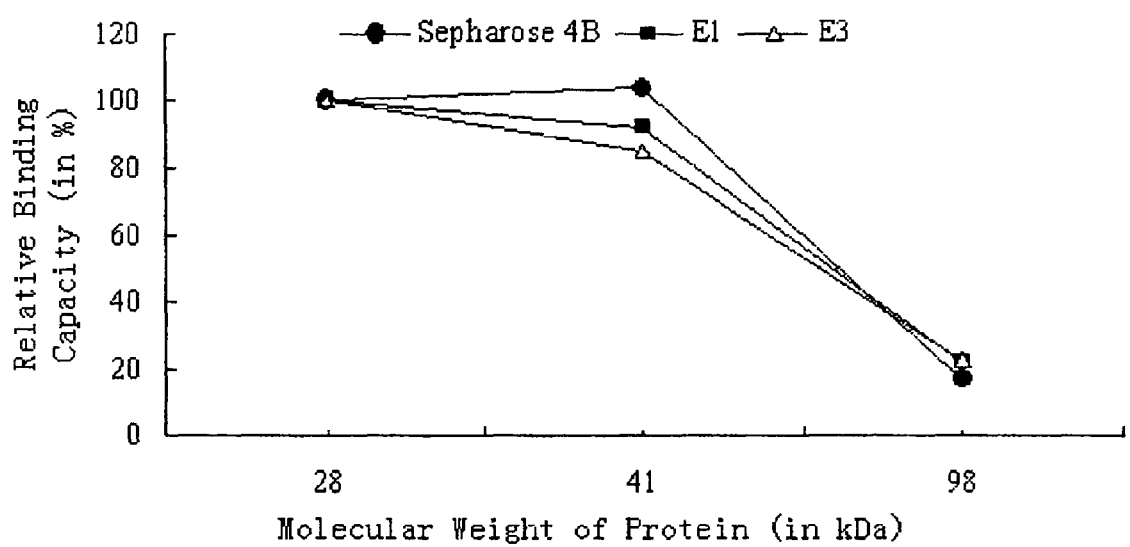
FIG. 14 shows three fused GST proteins (GST (28 kDa), GST-PX$^{p47}$ (41 kDa), and GST-Mucnc 18 (98 kDa)) were employed to examine change of the binding capacity. Relative binding capacity of three matrices was measured with a densitometer. Binding capacity of all matrices is set to be 100% for GST. Sepharose-4B (filled circle); E1 (filled square); E3 (open triangle).

Molecular Weight Dependence. Because the dendron modification generates a surface of controlled spacing between the immobilized ligands, binding capacity towards proteins of various molecular weights is intriguing. In particular, it is known that use of the second generation dendron guarantees a spacing over 24 angstrom (Cardona et al., J. Am. Chem. Soc. 1998, 120, 4023-4024). For this particular test, GST protein (28 kDa), GST-PX$^{p47}$ (41 kDa), and GST-munc-18 fragment (98 kDa) from the wild-type lysate were prepared. As shown in FIG. 14, binding capacity of the beads (E1, E3, and Sepharose 4B) decreases sharply as molecular weight of proteins increases. It is interesting to note that the degree of decrease holds same for the three different cases. When binding capacity of E1 is set at 100% for GST, GST-PX$^{p47}$ has a relative biding capacity of 92% and 22% for GST-munc18. For E3 bead, 85% for former protein and 23% for the latter protein are recorded. This strong dependence on protein molecular weight was also observed with glutathione Sepharose-4B. For glutathione Sepharose-4B, the binding efficiencies are 104% and 17% for GST-PX$^{p47}$ and GST-munc18, respectively. The only notable difference is a rather constant capacity for GST and GST-PX$^{p47}$ for this commercially available matrix. The difference might reflect heterogeneous spacing in Sepharose 4B. In this material, diverse spacings between GSH exist so that the matrix binds the fused GST as efficiently as the pristine GST. For the much bigger protein, GST-munc18, the spacings should be too small. In this regard, constant decrease of binding capacity of the dendron-treated beads supports again the regular spacing of GSH on the surface.

In summary, the dendron-modified matrix demonstrates selectivity as high as that of the commercial matrix (for example, Sepharose 4B), and almost same molecular weight dependence as the commercial one. The incorporation of the dendrons on AMPCPG matrix not only reduces the nonspecific binding effectively, but retains binding activity of GSH. Constant decrease of the binding capacity as increase of protein molecular weight was observed, and the phenomenon seems in harmony with the regular spacing between the immobilized GSH. In addition to the well-controlled spacing, favorable aspects such as mechanical stability, wide compatibility with various chemical environment, and easiness to handle promise interesting applications.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Numbering scheme is used for compounds throughout the Examples such as compound 1, compound 2, I, II, III, IV, V and so on. It is to be understood however, that the compound numbering scheme is consistent with and is confined to the particular Example section to which it is recited. For instance, compound 1 as recited in Example 2 may not necessarily be the same compound 1 as found in Example 3.

Example 1

Methods for Making Microarray Using Size-Controlled Macromolecule

In Example 1, designations I, II, III, IV, and V refer to various compounds and intermediate compounds as shown in FIG. 2.

Example 1.1

Materials. The silane coupling reagents, (3-glycidoxypropyl)methyldiethoxysilane (GPDES) and (3-aminopropyl)diethoxymethylsilane (APDES), were purchased from Gelest, Inc. and all other chemicals were of reagent grade from Sigma-Aldrich. Reaction solvents for the silylation are anhydrous ones in Sure/Seal bottles from Aldrich. All washing solvents for the substrates are of HPLC grade from Mallinckrodt Laboratory Chemicals. The UV grade fused silica plates (30 mm×10 mm×1.5 mm) were purchased from CVI Laser Corporation. The polished prime Si(100) wafers (dopant, phosphorus; resistivity, 1.5-2.1 Ω·cm) were purchased from MEMC Electronic Materials, Inc. Glass slides (2.5×7.5 cm) were purchased from Corning Co. All of the oligonucleotides were purchased from Metabion. Ultrapure water (18 MΩ/cm) was obtained from a Milli-Q purification system (Millipore).

Example 1.2

Instruments. The film thickness was measured with a spectroscopic ellipsometer (J. A. Woollam Co. Model M-44). UV-vis spectra were recorded on a Hewlett-Packard diodearray 8453 spectrophotometer. Tapping mode AFM experiments were performed with a Nanoscope IIIa AFM (Digital Instruments) equipped with an "E" type scanner.

Example 1.3

Cleaning the substrates. Substrates such as oxidized silicon wafer, fused silica, and glass slide, were immersed into Piranha solution (conc. $H_2SO_4$: 30% $H_2O_2$=7:3 (v/v)) and the reaction bottle containing the solution and the substrates was sonicated for an hour. (Caution: Piranha solution can oxidize organic materials explosively. Avoid contact with oxidizable materials.) The plates were washed and rinsed thoroughly with a copious amount of deionized water after the sonication. The clean substrates were dried in a vacuum chamber (30-40 mTorr) for the next steps.

Example 1.4

Preparing the hydroxylated substrates. The above clean substrates were soaked in 160 ml toluene solution with 1.0 ml (3-glycidoxypropyl)methyldiethoxysilane (GPDES) for 10 h. After the self-assembly, the substrates were washed with toluene briefly, placed in an oven, and heated at 110° C. for 30 min. The plates were sonicated in toluene, toluene-methanol (1:1 (v/v)), and methanol in a sequential manner for 3 min at each washing step. The washed plates were dried in a vacuum chamber (30-40 mTorr). GPDES-modified substrates were soaked in a neat ethylene glycol (EG) solution with two or three drops of 95% sulfuric acid at 80-100° C. for 8 h. After cooling, the substrates were sonicated in ethanol and methanol in a sequential manner each for 3 min. The washed plates were dried in a vacuum chamber (30-40 mTorr).

Example 1.5

Preparing the dendron-modified substrates. The above hydroxylated substrates were immersed into a methylene chloride solution dissolving the dendron (1.2 mM) and a coupling agent, 1-[3-(dimethylamino)propyl]-3-ethylcarbodiimide hydrochloride (EDC) or 1,3-dicyclohexylcarbodiimide (DCC) (11 mM) in the presence of 4-dimethylaminopyridine (DMAP) (0.82 mM). After 3 days at room temperature, the plates were sonicated in methanol, water, and methanol in a sequential manner each for 3 min. The washed plates were dried in a vacuum chamber (30-40 mTorr) for the next step.

Example 1.6

Preparing the NHS-modified substrates. The dendron-modified substrates were immersed into a methylene chloride solution with 1.0 M trifluoroacetic acid (TFA). After 3 h, they were again soaked in a methylene chloride solution with 20% (v/v) diisopropylethylamine (DIPEA) for 10 min. The plates were sonicated in methylene chloride and methanol each for 3 min. After being dried in a vacuum chamber, the deprotected substrates were incubated in the acetonitrile solution with di(N-succinimidyl)carbonate (DSC) (25 mM) and DIPEA (1.0 mM). After 4 h reaction under nitrogen atmosphere, the plates were placed in a stirred dimethylformamide solution for 30 min and washed briefly with methanol. The washed plates were dried in a vacuum chamber (30-40 mTorr) for the next step.

Example 1.7

Arraying oligonucleotides on the NHS-modified substrates. Probe oligonucleotides in 50 mM NaHCO3 buffer (pH, 8.5) were spotted side by side in a 4 by 4 format on the NHS-modified substrate. The microarray was incubated in a humidity chamber (80% humidity) for 12 h to give the amine-tethered DNA sufficient reaction time. Slides were then stirred in a hybridization buffer solution (2×SSPE buffer (pH, 7.4) containing 7.0 mM sodium dodecylsulfate) at 37° C. for 1 h and in boiling water for 5 min to remove non-specifically bound oligonucleotides. Finally, the DNA-functionalized microarray was dried under a stream of nitrogen for the next step. For a fair comparison, different kinds of probes were spotted in a single plate.

Example 1.8

Hybridization. Hybridization was performed in the hybridization buffer solution containing a target oligonucleotide (1.0 nM) tagged with a Cy3 fluorescent dye at 50° C. for 1 h using a GeneTAC™ HybStation (Genomic Solutions, Inc.). The microarray was rinsed with the hybridization buffer solution in order to remove excess target oligonucleotide and dried with nitrogen. The fluorescence signal on each spot was measured with a ScanArray Lite (GSI Lumonics) and analyzed by Imagene 4.0 (Biodiscovery).

Example 1.9

Synthesis of the Dendron

Example 1.9.1

Preparation of 9-anthrylmethyl N-(3-carboxylpropyl)carbamate (1)—Compound I

4-Aminobutyric acid (0.50 g, 4.8 mmol, 1.0 equiv) and triethylamine (TEA) (1.0 ml, 7.3 mmol, 1.5 equiv) were dissolved in N,N-dimethylformamide (DMF) and stirred at 50° C. 9-Anthrylmethyl p-nitrophenyl carbonate (1.81 g, 4.8 mmol, 1.0 equiv) was slowly added while stirring. After stirring at 50° C. for 2 h, the solution was evaporated to dryness, and the solution was basified with 0.50 N sodium hydroxide (NaOH) solution. The aqueous solution was washed with ethyl acetate (EA), stirred in an ice bath and acidified with dilute hydrochloric acid (HCl). After the product was extracted with EA, the organic solution was dried with anhydrous MgSO$_4$, filtered and evaporated. The total weight of the resulting yellow powder was 1.06 g and the yield was 65%.

$^1$H NMR(CDCl$_3$)

δ 11.00-9.00 (br, CH$_2$COOH, 1H), 8.41 (s, C$_{14}$H$_9$CH$_2$, 1H), 8.31 (d, C$_{14}$H$_9$CH$_2$, 2H), 7.97 (d, C$_{14}$H$_9$CH$_2$, 2H), 7.51 (t, C$_{14}$H$_9$CH$_2$, 2H), 7.46 (t, C$_{14}$H$_9$CH$_2$, 2H), 6.08 (s, C$_{14}$H$_9$CH$_2$O, 2H), 5.01 (t, OCONHCH$_2$, 1H), 3.23 (q, NHCH$_2$CH$_2$, 2H), 2.34 (t, CH$_2$CH$_2$COOH, 2H), 1.77 (m, CH$_2$CH$_2$CH$_2$, 2H).

$^{13}$C NMR(CDCl$_3$)

δ 178.5 (CH$_2$COOH), 157.9 (OCONH), 132.1 (C$_{14}$H$_9$CH$_2$), 131.7 (C$_{14}$H$_9$CH$_2$), 129.7 (C$_{14}$H$_9$CH$_2$), 129.7 (C$_{14}$H$_9$CH$_2$), 127.3 (C$_{14}$H$_9$CH$_2$), 126.8 (C$_{14}$H$_9$CH$_2$), 125.8 (C$_{14}$H$_9$CH$_2$), 124.6 (C$_{14}$H$_9$CH$_2$), 60.2 (C$_{14}$H$_9$CH$_2$), 41.0 (NHCH$_2$CH$_2$), 31.7 (CH$_2$CH$_2$COOH), 25.6 (CH$_2$CH$_2$CH$_2$).

Example 1.9.2

Preparation of 9-anthrylmethyl N-{[(tris{[2-(methoxycarbonyl)ethoxy]methyl}methyl)amino]carbonyl}propylcarbonate (II)—Compound II 9-Anthrylmethyl N-(3-carboxylpropyl)carbamate (0.65 g, 1.93 mmol, 1.5 equiv), 1-[3-(dimethylamino)propyl]-3-ethylcarbodiimide hydrochloride (EDC) (0.37 g, 1.93 mmol, 1.5 equiv), and 1-hydroxybenzotriazole hydrate (HOBT) (0.261 g, 1.93 mmol, 1.5 equiv) were dissolved in acetonitrile and stirred at room temperature. Tris{[(methoxycarbonyl)ethoxy]methyl} aminomethane (0.49 g, 1.29 mmol, 1.0 equiv) dissolved in acetonitrile was added with stirring, After stirring at room temperature for 12 h, the acetonitrile was evaporated. The crude product was dissolved in EA and washed with 1.0 N HCl and saturated sodium bicarbonate solution. After being dried with anhydrous MgSO$_4$, filtered, and evaporated, the crude product was loaded in a column packed with silica gel. Purification by column chromatography (eluent: ethyl acetate:hexane=5:1 (v/v)) resulted in a viscous yellow liquid. The total weight of the yellow liquid was 0.67 g, and the yield was 74%.

$^1$H NMR(CDCl$_3$)

δ 8.43 (s, C$_{14}$H$_9$CH$_2$, 1H), 8.36 (d, C$_{14}$H$_9$CH$_2$, 2H), 7.99 (d, C$_{14}$H$_9$CH$_2$, 2H), 7.53 (t, C$_{14}$H$_9$CH$_2$, 2H), 7.47 (t, C$_{14}$H$_9$CH$_2$, 2H), 6.15 (s, CONHC, 1H), 6.08 (s, C$_{14}$H$_9$CH$_2$O, 2H), 5.44 (t, OCONHCH$_2$, 1H), 3.63-3.55 (m, CH$_2$OCH$_2$CH$_2$COOCH$_3$, 21H), 3.27 (q, NHCH$_2$CH$_2$, 2H), 2.46 (t, CH$_2$CH$_2$COOCH$_3$, 6H), 2.46 (t, CH$_2$CH$_2$CONH, 2H), 1.81 (m, CH$_2$CH$_2$CH$_2$, 2H).

$^{13}$C NMR(CDCl$_3$)

δ173.2 (CH$_2$CONH), 172.7 (CH$_2$COOCH$_3$), 157.4 (OCONH), 132.9 (C$_{14}$H$_9$CH$_2$), 131.5 (C$_{14}$H$_9$CH$_2$), 129.5 (C$_{14}$H$_9$CH$_2$), 129.4 (C$_{14}$H$_9$CH$_2$), 127.5 (C$_{14}$H$_9$CH$_2$), 127.0 (C$_{14}$H$_9$CH$_2$), 125.6 (C$_{14}$H$_9$CH$_2$), 124.7 (C$_{14}$H$_9$CH$_2$), 69.6 (NHCCH$_2$O), 67.2 (C$_{14}$H$_9$CH$_2$), 60.1 (OCH$_2$CH$_2$), 59.4 (NHCCH$_2$), 52.1 (OCH$_3$), 40.8 (NHCH$_2$CH$_2$), 35.1 (OCH$_2$CH$_2$), 34.7 (CH$_2$CH$_2$CONH), 26.3 (CH$_2$CH$_2$CH$_2$).

Anal. Calcd for C$_{36}$H$_{46}$N$_2$O$_{12}$ 0.5H$_2$O: C, 61.18; H, 6.65; N, 4.03. Found: C, 61.09; H, 6.69; N, 3.96.

Example 1.9.3

Preparation of 9-anthrylmethyl N-[({tris[(2-carboxyethoxy)methyl]methyl}amino)carbonyl]propylcarbamate (III)—Compound III 9-Anthrylmethyl N-{[(tris{[2-(methoxycarbonyl)ethoxy]methyl}methyl)amino]carbonyl}propyl-carbonate (0.67 g, 0.93 mmol) was dissolved in acetone (30 ml) and 0.20 N NaOH (30 ml, 6 mmol). After being stirred at room temperature for 1 d, the acetone was evaporated. The aqueous solution was washed with EA, stirred in an ice bath and acidified with dilute HCl. After the product was extracted with EA, the organic solution was dried with anhydrous MgSO$_4$, filtered and evaporated. Solidification in acetone and ether solution at −20° C. resulted in a yellow powder. The total weight of the final pale yellow powder was 0.54 g with a yield of 88%.

$^1$H NMR(CDCl$_3$)

δ 11.00-9.00 (br, CH$_2$COOH, 3H}, 8.61 (s, C$_{14}$H$_9$CH$_2$, 1H}, 8.47 (d, C$_{14}$H$_9$CH$_2$, 2H), 8.11 (d, C$_{14}$H$_9$CH$_2$, 2H), 7.60 (t, C$_{14}$H$_9$CH$_2$, 2H}, 7.52 (t, C$_{14}$H$_9$CH$_2$, 2H), 6.63 (s, CONHC, 1H), 6.36 (t, OCONHCH$_2$, 1H), 6.12 (s, C$_{14}$H$_9$CH$_2$O, 2H). 3.40-363 (m, CH$_2$OCH$_2$CH$_2$COOH, 12H), 3.20 (q, NHCH$_2$CH$_2$, 2H), 2.52 (t, CH$_2$CH$_2$COOH, 6H), 2.17 (t, CH$_2$CH$_2$CONH, 2H), 1.75 (m, CH$_2$CH$_2$CH$_2$, 2H).

$^{13}$C NMR(CDCl$_3$)

δ 172.2 (CH$_2$COOH), 172.0 (CH$_2$CONH), 156.7 (OCONH), 131.2 (C$_{14}$H$_9$CH$_2$), 130.7 (C$_{14}$H$_9$CH$_2$), 128.6 (C$_{14}$H$_9$CH$_2$), 128.4 (C$_{14}$H$_9$CH$_2$), 127.3 (C$_{14}$H$_9$CH$_2$), 126.2 (C$_{14}$H$_9$CH$_2$), 124.8 (C$_{14}$H$_9$CH$_2$), 124.0 (C$_{14}$H$_9$CH$_2$), 68.6 (NHCCH$_2$O), 66.5 (C$_{14}$H$_9$CH2), 59.5 (OCH$_2$CH$_2$), 58.0 (NHCCH$_2$), 40.0 (NHCH$_2$CH$_2$), 34.0 (OCH$_2$CH$_2$), 33.5 (CH$_2$CH$_2$CONH), 25.8 (CH$_2$CH$_2$CH$_2$).

Anal. Calcd for C$_{33}$H$_{40}$N$_2$O$_{12}$ 1.5H$_2$O: C, 57.97; H, 6.34; N, 4.10. Found: C, 57.89; H, 6.21; N, 4.09.

Example 1.9.4

Preparation of 9-anthrylmethyl N-[({tris[(2-{[(tris{[2-(methoxycarbonyl)ethoxy]methyl}(methyl)amino]carbonyl}ethoxy)methyl]methyl}amino)carbonyl]propylcarbamate (IV)—Compound IV 9-Anthrylmethyl N-[({tris[(2-carboxyethoxy)methyl]methyl} amino)carbonyl]propylcarbamate (0.54 g, 0.82 mmol, 1.0 equiv), EDC (0.55 g, 2.87 mmol, 3.5 equiv), and HOBT (0.39 g, 2.89 mmol, 3.5 equiv) were dissolved in acetonitrile and stirred at room temperature. Tris{[(methoxycarbonyl)ethoxy]methyl} aminomethane (0.96 g, 2.53 mmol, 3.1 equiv) dissolved in acetonitrile was added with stirring. After stirring at room temperature for 36 h, the acetonitrile was evaporated. The crude product was dissolved in EA and washed with 1.0 N HCl and saturated sodium bicarbonate solution. After drying with anhydrous MgSO$_4$, filtered, and evaporated, the crude product was loaded in a column packed with silica gel. Column purification (eluent: ethyl acetate: methanol=20:1 (v/v)) resulted in a viscous yellow liquid. The total weight of the yellow liquid was 1.26 g with an 88% yield.

$^1$H NMR(CDCl$_3$)

δ 8.47 (s, C$_{14}$H$_9$CH$_2$, 1H), 8.39 (d, C$_{14}$H$_9$CH$_2$, 2H), 8.02 (d, C$_{14}$H$_9$CH$_2$, 2H), 7.53 (t, C$_{14}$H$_9$CH$_2$, 2H), 7.47 (t, C$_{14}$H$_9$CH$_2$, 2H), 6.60 (s, CH$_2$CH$_2$CH$_2$CONHC, 1H), 6.13 (s, OCH$_2$CH$_2$CONHC, 3H), 6.11 (s, C$_{14}$H$_9$CH$_2$O, 2H), 5.79 (t, OCONHCH$_2$, 1H), 3.65-3.60 (m, CH$_2$OCH$_2$CH$_2$CONH, CH$_2$OCH$_2$CH$_2$COOCH$_3$, 75H), 3.29 (q, NHCH$_2$CH$_2$, 2H), 2.50 (t, CH$_2$CH$_2$COOCH$_3$, 18H), 2.36 (t, OCH$_2$CH$_2$CONH, 6H), 2.27 (t, CH$_2$CH$_2$CONH, 2H), 1.85 (m, CH$_2$CH$_2$CH$_2$, 2H).

$^{13}$C NMR(CDCl$_3$)

δ 173.3 (OCH$_2$CH$_2$CONH), 172.5 (CH$_2$CH$_2$CH$_2$CONH), 171.6 (CH$_2$COOCH$_3$), 157.2 (OCONH), 131.8 (C$_{14}$H$_9$CH$_2$), 131.5 ($C_{14}H_9CH_2$), 129.4 ($C_{14}H_9CH_2$), 129.3 ($C_{14}H_9CH_2$), 127.6 ($C_{14}H_9CH_2$), 127.0 ($C_{14}H_9CH_2$), 125.6 ($C_{14}H_9CH_2$), 124.7 ($C_{14}H_9CH_2$), 69.5 ($NHCCH_2OCH_2CH_2COOCH_3$), 67.9 ($NHCCH_2OCH_2CH_2CONH$), 67.2 ($C_{14}H_9CH_2$), 60.3 ($OCH_2CH_2CONH$), 60.2 ($OCH_2CH_2COOCH_3$), 59.2 ($NHCCH_2OCH_2CH_2COOCH_3$, $NHCCH_2OCH_2CH_2CONH$), 52.1 ($OCH_3$), 41.0 ($NHCH_2CH_2$), 37.6 ($OCH_2CH_2CONH$), 35.1 ($OCH_2CH_2COOCH_3$), 34.7 ($CH_2CH_2CH_2CONH$), 26.3 ($CH_2CH_2CH_2$).

Anal. Calcd for $C_{81}H_{121}N_5O_{36}\cdot H_2O$: C, 55.31; H, 7.05; N, 3.98. Found: C, 55.05; H, 7.08; N, 4.04.

MALDI-TOF-MS: 1763.2 (MNa+), 1779.2 (MK+).

Example 1.9.5

Preparation of 9-anthrylmethyl N-({[tris({2-[({tris[(2-carboxyethoxy)methyl]methyl} amino)carbonyl]ethoxy}methyl)methyl]amino}carbonyl)propylcarbamate (V)—Compound V 9-Anthrylmethyl N-[({tris[(2-{[(tris{[2-(methoxycarbonyl)ethoxy]methyl}methyl)amino]carbonyl} ethoxy)methyl]methyl}amino)carbonyl]propylcarbamate (0.60 g, 0.34 mmol) was dissolved in acetone (30 ml) and 0.20 N NaOH (30 ml). After stirring at room temperature for 1 d, the acetone was evaporated. The aqueous solution was washed with EA, stirred in an ice bath and acidified with dilute HCl. After the product was extracted with EA, the organic solution was dried with anhydrous MgSO$_4$, filtered and evaporated. The total weight of the final yellow powder was 0.37 g and the yield was 68%.

$^1$H NMR(DMSO)

δ 13.00-11.00 (br, $CH_2COOH$, 9H), 8.66 (s, $C_{14}H_9CH_2$, 1H), 8.42 (d, $C_{14}H_9CH_2$, 2H), 8.13 (d, $C_{14}H_9CH2$, 2H), 7.62 (t, $C_{14}H_9CH_2$, 2H), 7.54 (t, $C_{14}H_9CH_2$, 2H), 7.12 (t. OCONHCH$_2$, 1H), 7.10 (s, $OCH_2CH_2CONHC$, 3H), 7.06 (s, $CH_2CH_2CH_2CONHC$, 1H), 6.06 (s, $C_{14}H_9CH_2O$, 2H), 3.57-3.55 (m, $CH_2OCH_2CH_2CONH$, $CH_2OCH_2CH_2COOH$, 48H), 3.02 (q, $NHCH_2CH_2$, 2H), 2.42 (t, $CH_2CH_2COOH$, 18H), 2.32 (t, $OCH_2CH_2CONH$, 6H), 2.11 (t, $CH_2CH_2CH_2CONH$, 2H), 1.60 (m, $CH_2CH_2CH_2$, 2H).

$^{13}$C NMR(DMSO)

δ 172.8 ($CH_2COOH$), 172.2 ($CH_2CH_2CH_2CONH$), 170.5 ($OCH_2CH_2CONH$), 156.5 (OCONH), 131.0 ($C_{14}H_9CH_2$), 130.6 ($C_{14}H_9CH_2$), 129.0 ($C_{14}H_9CH_2$), 128.7 ($C_{14}H_9CH_2$), 127.6 ($C_{14}H_9CH_2$), 126.7 ($C_{14}H_9CH_2$), 125.4 ($C_{14}H_9CH_2$), 124.3 ($C_{14}H_9CH_2$), 68.3 ($NHCCH_2OCH_2CH_2COOH$), 67.4 ($NHCCH_2OCH_2CH_2CONH$), 66.8 ($C_{14}H_9CH_2$), 59.8 ($OCH_2CH_2COOH$), 59.6 ($OCH_2CH_2CONH$), 57.9 ($NHCCH_2OCH_2CH_2CONH$), 55.9 ($NHCCH_2OCH_2CH_2COOH$), 36.4 ($NHCH_2CH_2$), 34.6 ($OCH_2CH_2COOH$), 30.8 ($OCH_2CH_2CONH$), 29.7 ($CH_2CH_2CH_2CONH$), 25.9 ($CH_2CH_2CH_2$).

Example 2

Methods of Producing Alternative Starting Material Dendron Macromolecule—Fmoc-Spacer-[9]-Acid In Example 2, various indicated compounds are referred to as compound 1, 2 and so forth.

First, we synthesized a spacer, 6-azidohexylamine (1) from 1,6-dibromohexane according to Lee, J. W.; Jun, S. I.; Kim, K. Tetrahedron Lett., 2001, 42, 2709.

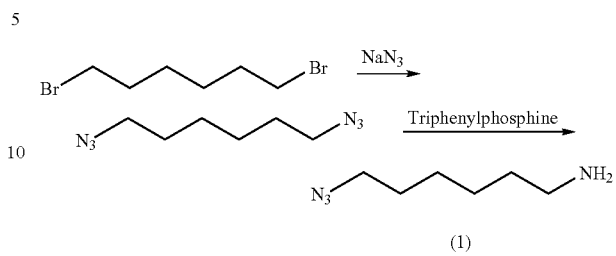

This spacer was attached to repeating unit (2) through unsymmetric urea formation and made N$_3$-spacer-[3]ester (3). The repeating unit was synthesized by condensation of TRIS with tert-butyl acrylate, which had been reported in Cardona, C. M.; Gawley, R. E. J. Org. Chem. 2002, 67, 141.

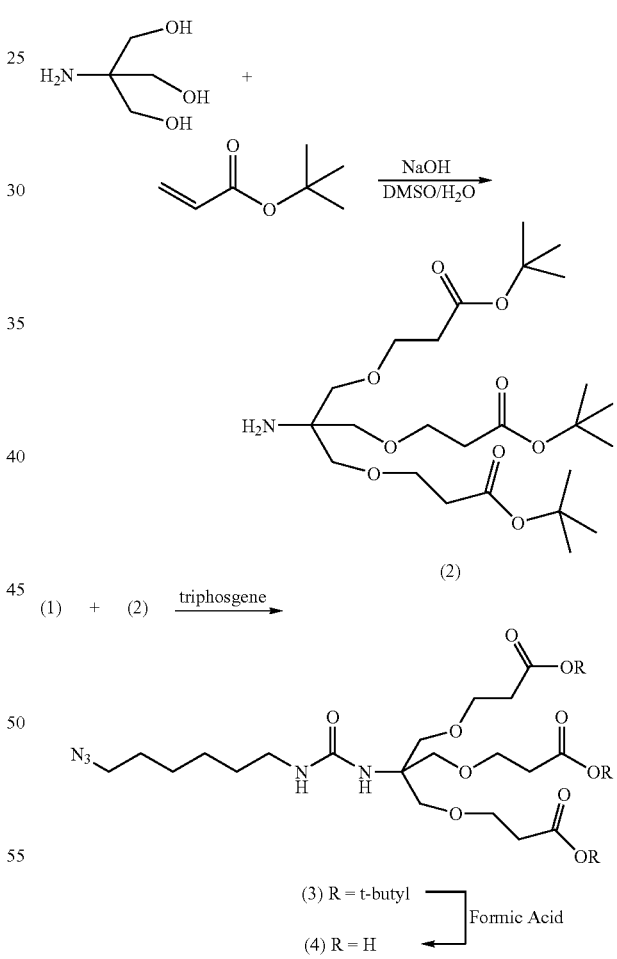

This triester was transformed to N$_3$-spacer-[3]acid (4) through hydrolysis and coupled with triester (2) under peptide coupling conditions, which led to N$_3$-spacer-[9]ester. After reduction of azide to amine and protection of amine with Fmoc group, hydrolysis of nonaester afforded Fmoc-spacer-[9]acid (5).

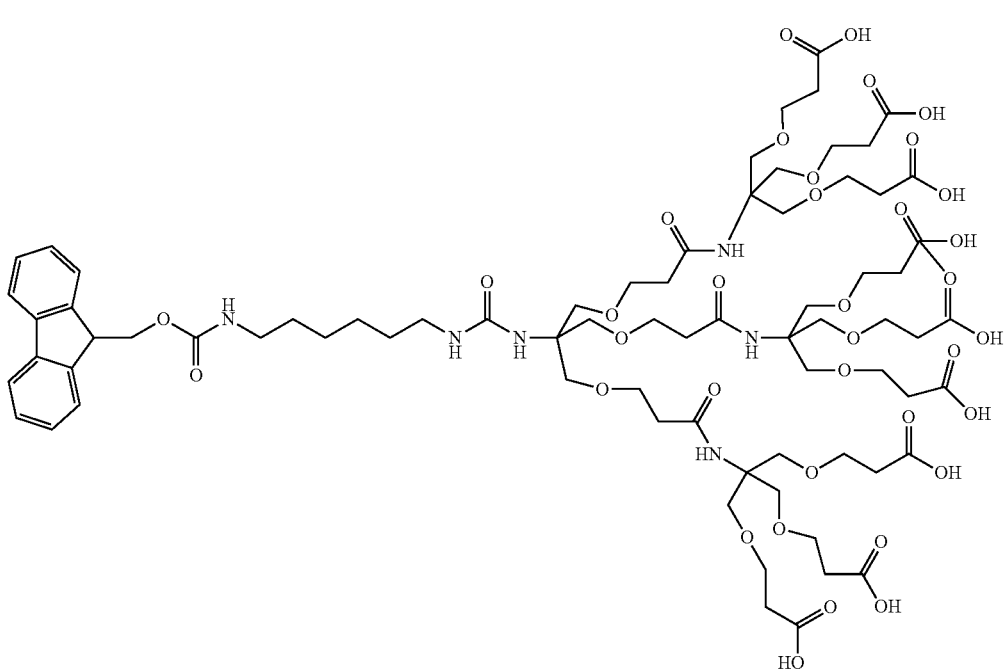

(5)

N-(6-Azidohexyl)-N'-tris {[2-(tert-butoxyearbonyl) ethoxy]methyl}-methylurea (3). Triphosgene (1.3 g, 4.3 mmol) was dissolved in anhydrous $CH_2Cl_2$ (20 mL). A mixture of 6-azidohexylamine (1) (1.6 g, 12 mmol) and N,N-diisopropylethylamine (DIEA, 2.4 mL, 13.8 mmol) in anhydrous $CH_2Cl_2$ (35 mL) was added dropwise to the stirred solution of triphosgene over a period of 7 h using a syringe pump. After further stirring for 2 h, a solution of (2) (6.4 g, 13 mmol) and DIEA (2.7 mL, 15.2 mmol) in anhydrous $CH_2Cl_2$ (20 mL) was added. The reaction mixture was stirred for 4 h at room temperature under nitrogen, and washed with 0.5 M HCl and brine. The organic layer was then dried over anhydrous $MgSO_4$, and the solvent was removed by evacuation. Purification with column chromatography (silica, 1:1 EtOAc/hexane) yielded colorless oil (3.0 g, 40%).

$^1$H NMR ($CDCl_3$, 300 MHz): δ 1.45 (s, $(CH_3)_3C$, 27H); 1.36-1.58 (m, $CH_2CH_2CH_2CH_2$, 8H); 2.46 (t, $CH_2CH_2O$, J=6.4 Hz, 6H), 3.13 (m, $CONHCH_2$, 2H), 3.26 (t, $N_3CH_2$, J=6.9 Hz, 2H), 3.64-3.76 (m, $CCH_2O$ and $CH_2CH_2O$, 12H); 5.00 (t, $CH_2NHCO$, J=6.7 Hz, 1H), 5.29 (s, CONHC, 1H).

$^{13}$C NMR ($CDCl_3$, 75 MHz): δ 26.52, 26.54, 28.81, 30.26 ($CH_2CH_2CH_2CH_2$); 28.14 ($(CH_3)_3C$); 36.20 ($CH_2CH_2O$); 39.86 ($CONHCH_2$); 51.40 ($N_3CH_2$); 58.81 ($CCH_2O$); 67.16 ($CH_2CH_2O$); 69.23 ($CCH_2O$); 80.58 ($(CH_3)_3C$); 157.96 (NHCONH); 171.26 (COOt-Bu).

FAB-MS: 674.26 ($M^+$).

N-(6-Azidohexyl)-N'-tris{[2-carboxyethoxy] methyl}methylurea (4). $N_3$-spacer-[3]ester (3) (0.36 g, 0.56 mmol) was stirred in 6.6 mL of 96% formic acid for 24 h. The formic acid was then removed at reduced pressure at 50° C. to produce colorless oil in a quantitative yield.

$^1$H NMR ($CD_3COCD_3$, 300 MHz): δ 1.34-1.60 (m, $CH_2CH_2CH_2CH_2$, 8H); 2.53 (t, $CH_2CH_2O$, J=6.4 Hz, 6H), 3.07 (t, $CONHCH_2$, J=6.9 Hz, 2H), 3.32 (t, $N_3CH_2$, J=6.9 Hz, 2H), 3.67-3.73 (m, $CCH_2O$ and $CH_2CH_2O$, 12H).

$^{13}$C NMR ($CD_3COCD_3$, 75 MHz): δ 27.21, 29.54, 31.02 ($CH_2CH_2CH_2CH_2$); 35.42 ($CH_2CH_2O$); 40.27 ($CONHCH_2$); 52.00 ($N_3CH_2$); 59.74 ($CCH_2O$); 67.85 ($CH_2CH_2O$); 70.96 ($CCH_2O$); 158.96 (NHCONH); 173.42 (COOH).

FAB-MS: 506.19 ($MH^+$).

N-(6-Azidohexyl)-N'-tris[(2-{[(tris{[2-(tert-butoxycarbonyl)ethoxy]-methyl}methyl)amino]carbonyl}ethoxy)methyl]methylurea (4.1).

The HOBt (0.20 g, 1.5 mmol), DIEA (0.30 mL, 1.8 mmol), and EDC (0.33 g, 1.8 mmol) were added to (4) (0.25 g, 0.50 mmol) in 5.0 mL of dry acetonitrile. Then, the amine (2) (1.14 g, 2.3 mmol) dissolved in 2.5 mL of dry acetonitrile was added, and the reaction mixture was stirred under $N_2$ for 48 h. After removal of the solvent at reduced pressure, the residue was dissolved in MC and washed with 0.5 M HCl and brine. The organic layer was then dried over $MgSO_4$, the solvent was removed in vacuo, and column chromatography ($SiO_2$, 2:1 EtOAc/hexane) yielded a colorless oil (0.67 g, 70%).

$^1$H NMR ($CDCl_3$, 300 MHz): δ 1.45 (s, $(CH_3)_3C$, 81H); 1.36-1.58 (m, $CH_2CH_2CH_2CH_2$, 8H); 2.40-2.47 (m, $CH_2CH_2O$ gen. 1 & 2, 24H), 3.13 (m, $CONHCH_2$, 2H), 3.26 (t, $N_3CH_2$, 6.9 Hz, 2H), 3.62-3.69 (m, $CCH_2O$ gen. 1 & 2, $CH_2CH_2O$ gen. 1 & 2, 48H); 5.36 (t, $CH_2NHCO$, J=6.7 Hz, 1H), 5.68 (br, CONHC, 1H), 6.28 (br, amide NH, 3H).

$^{13}$C NMR (CDCl$_3$, 75 MHz): δ 26.59, 26.69, 28.91, 30.54 (CH$_2$CH$_2$CH$_2$CH$_2$); 28.22 ((CH$_3$)$_3$C); 36.20 (CH$_2$CH$_2$O gen. 2); 37.43 (CH$_2$CH$_2$O gen. 1); 39.81 (CONHCH$_2$); 51.47 (N$_3$CH$_2$); 58.93 (CCH$_2$O gen. 1); 59.89 (CCH$_2$O gen. 2); 67.15 (CH$_2$CH$_2$O gen. 2); 67.68 (CH$_2$CH$_2$O gen. 1); 69.23 (CCH$_2$O gen. 2); 70.12 (CCH$_2$O gen. 1); 80.57 ((CH$_3$)$_3$C); 158.25 (NHCONH); 171.01 (COOt-Bu) 171.41 (CONH amides).

MALDI-MS: 1989.8 (MNa$^+$), 2005.8 (MK$^+$).

N-(6-Aminohexyl)-N'-tris[(2-{[(tris{[2-(tert-butoxycarbonyl)ethoxy]-methyl}methyl)amino]carbonyl}ethoxy)methyl]methylurea (4.2).

Nona-tert-butyl ester (4.1) (0.37 g, 0.20 mmol) was stirred with 10% Pd/C (37.0 mg) in ethanol (20.0 mL) under H$_2$ at room temperature for 12 h. After checking completion of the reaction with TLC, the mixture was filtered with a 0.2 µm Millipore filter. After the filter paper was rinsed with CH$_2$Cl$_2$, the combined solvent was removed in vacuo, and colorless oil was recovered.

N-{6-(9-fluorenylmethoxycarbonyl)aminohexyl}-N'-tris[(2-{1[(tris{[2-(tert-butoxycarbonyl)ethoxy]methyl}methyl)amino]carbonyl}ethoxy)methyl]methylurea (4.3).

The amine (4.2) (0.33 g, 0.17 mmol) and DIEA (33 µL, 0.19 mmol) were dissolved in 5.0 mL of CH$_2$Cl$_2$, and stirred for 30 min under nitrogen atmosphere. 9-Fluorenylmethyl chloroformate (48 mg, 0.19 mmol) in 2.0 mL of CH$_2$Cl$_2$ was added, and the reaction mixture was stirred for 3 h at room temperature. The solvent was removed under reduced pressure and washed with 0.5 M HCl and brine. The residue was purified with column chromatography (silica, EtOAc) to yield colorless oil (0.18 g, 64%).

$^1$H NMR (CDCl$_3$, 300 MHz): δ 1.45 (s, (CH$_3$)$_3$C, 81H); 1.23-1.58 (m, CH$_2$CH$_2$CH$_2$CH$_2$, 8H); 2.37-2.47 (m, CH$_2$CH$_2$O gen. 1 & 2, 24H); 3.10-3.22 (m, CONHCH$_2$, 4H); 3.62-3.70 (m, CCH$_2$O gen. 1 & 2, CH$_2$CH$_2$O gen. 1 & 2, 48H); 4.22 (t, CH(fluorenyl)-CH$_2$, J=7.1 Hz, 1H); 4.36 (d, fluorenyl-CH$_2$, J=7.1 Hz, 2H); 5.27-5.35 (m, CH$_2$NHCO, 2H); 5.67 (br, CONHC, 1H); 6.25 (br, amide, 3H); 7.28-7.77 (fluorenyl, 8H).

$^{13}$C NMR (CDCl$_3$, 75 MHz): δ 26.85, 27.02, 30.27, 30.88 (CH$_2$CH$_2$CH$_2$CH$_2$); 28.49 ((CH$_3$)$_3$C); 36.48 (CH$_2$CH$_2$O gen. 2); 37.73 (CH$_2$CH$_2$O gen. 1); 40.03, 41.34 (CONHCH$_2$); 47.68 (CH(fluorenyl)-CH$_2$); 59.22 (CCH$_2$O gen. 1); 60.16 (CCH$_2$O gen. 2); 66.87 (fluorenyl-CH$_2$); 67.43 (CH$_2$CH$_2$O gen. 2); 67.98 (CH$_2$CH$_2$O gen. 1); 69.52 (CCH$_2$O gen. 2); 70.42 (CCH$_2$O gen. 1); 80.84 ((CH$_3$)$_3$C); 120.28, 125.52, 127.38, 127.98, 141.65, 144.48 (fluorenyl); 156.88 (OCONH); 158.52 (NHCONH); 171.27 (COOt-Bu) 171.65 (amide CONH).

MALDI-MS: 2186.8 (MNa$^+$), 2002.8 (MK$^+$).

N-{6-(9-fluorenylmethoxycarbonyl)aminohexyl}-N'-tris[(2-{[(tris{[2-carboxyethoxy]methyl}methyl)amino]carbonyl}ethoxy)methyl]-methylurea (5). Nona-tert-butyl ester having a protecting group (4.3) (0.12 g, 72 mmol) was stirred in 10 mL of 96% formic acid for 18 h. The formic acid was then removed at reduced pressure at 50° C. to produce colorless oil in a quantitative yield.

$^1$H NMR (CD$_3$COCD$_3$, 300 MHz): δ 1.23-1.51 (m, CH$_2$CH$_2$CH$_2$CH$_2$, 8H); 2.44-2.58 (m, CH$_2$CH$_2$O gen. 1 & 2, 24H); 3.15-3.18 (m, CONHCH$_2$, 4H); 3.61-3.75 (m, CCH$_2$O gen. 1 & 2, CH$_2$CH$_2$O gen. 1 & 2, 48H); 4.23 (t, CH(fluorenyl)-CH$_2$, J=7.0 Hz, 1H); 4.35 (d, fluorenyl-CH$_2$, J=7.0 Hz, 2H); 5.85, 6.09 (br, CH$_2$NHCO, 2H); 6.57 (br, CONHC, 1H); 6.88 (br, amide NH, 3H); 7.31-7.88 (fluorenyl, 8H).

$^{13}$C NMR (CD$_3$COCD$_3$, 75 MHz): δ 27.21, 27.33, 30.69, 30.98 (CH$_2$CH$_2$CH$_2$CH$_2$); 35.31 (CH$_2$CH$_2$O gen. 2); 37.83 (CH$_2$CH$_2$O gen. 1); 40.56, 41.54 (CONHCH$_2$); 48.10 (CH(fluorenyl)-CH$_2$); 59.93 (CCH$_2$O gen. 1); 61.10 (CCH$_2$O gen. 2); 66.86 (fluorenyl-CH$_2$); 67.81 (CH$_2$CH$_2$O gen. 2); 68.37 (CH$_2$CH$_2$O gen. 1); 69.80 (CCH$_2$O gen. 2); 70.83 (CCH$_2$O gen. 1); 120.84, 126.13, 127.98, 128.56, 142.10, 145.16 (fluorenyl); 157.50 (OCONH); 159.82 (NHCONH); 173.20 (amide CONH); 173.93 (COOH).

Example 3

Additional Dendron Compounds

It is to be noted that while a particular protecting group may be shown with a macromolecule, the compounds are not limited to the specific protecting groups shown. Moreover, while various chains and spacers are depicted indicating an exact molecular structure, modifications are possible according to accepted chemical modification methods to achieve the function of a density controlled, preferably low density, array on a substrate surface. As a point of reference for the shorthand description of the compounds, the left most letter(s) indicates the protecting group; the numeral in brackets indicates the number of branched termini; and the right most chemical entity indicates the chemistry on the branched termini. For example, "A-[27]-acid" indicates anthrylmethyl protecting group; 27 termini, and acid groups at the termini.

A-[27]-acid
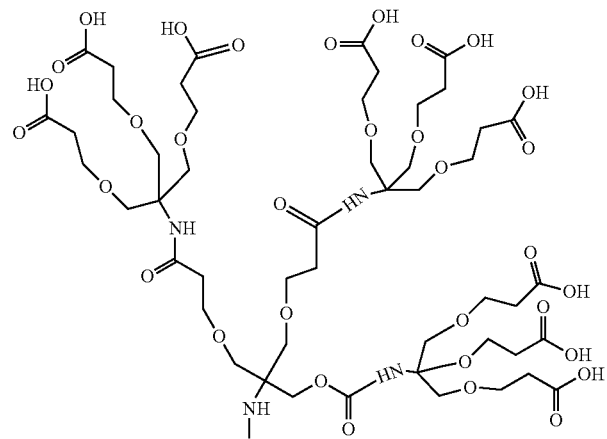
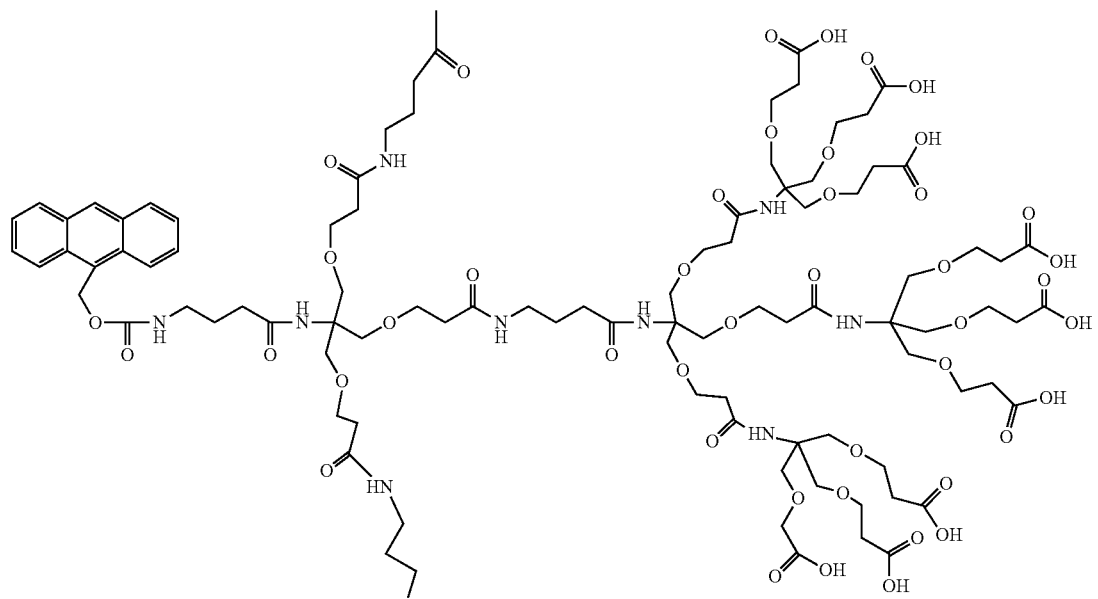
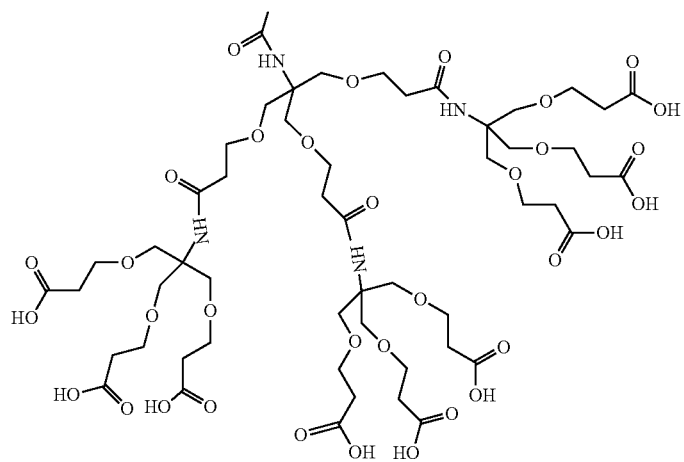

37
Boc-[1]-acid
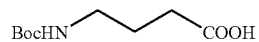
Boc-[3]-ester
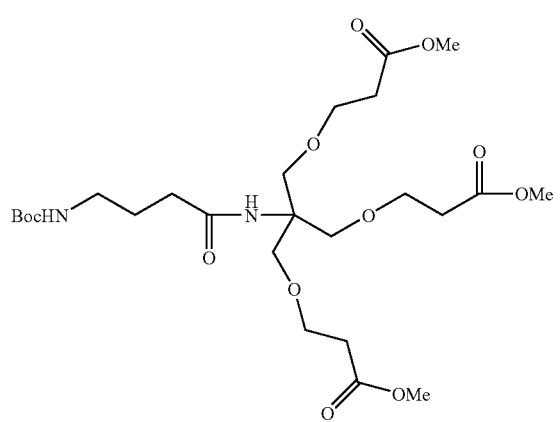 [SMILES: COC(=O)CCOCC(COCCC(=O)OC)(COCCC(=O)OC)NC(=O)CCCNC(=O)OC(C)(C)C]
38
Boc-[3]-acid
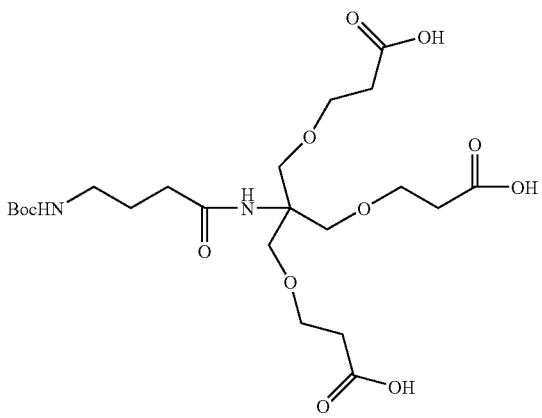 [SMILES: CC(C)(C)OC(=O)NCCCC(=O)NC(COCCC(=O)O)(COCCC(=O)O)COCCC(=O)O]
Boc-[9]-ester
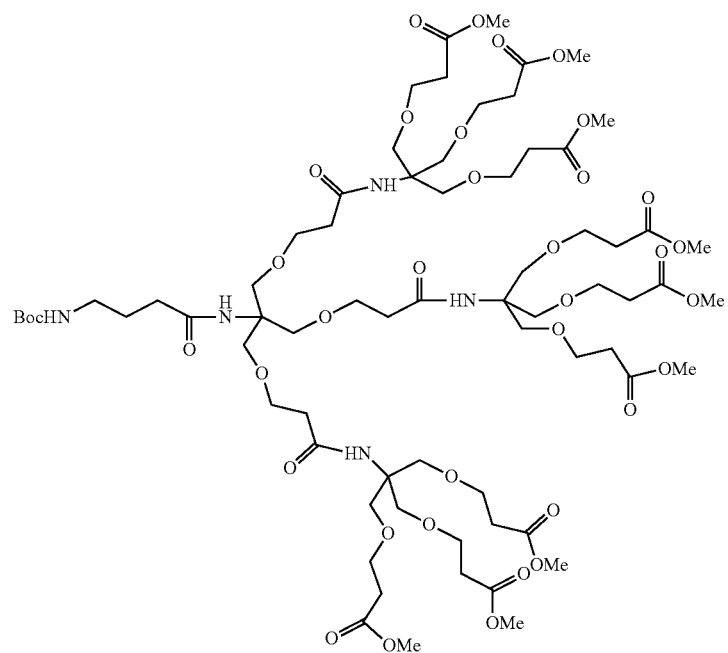 [SMILES: COC(=O)CCOCC(COCCC(=O)OC)(COCCC(=O)OC)NC(=O)CCOCC(COCCC(=O)NC(COCCC(=O)OC)(COCCC(=O)OC)COCCC(=O)OC)(COCCC(=O)NC(COCCC(=O)OC)(COCCC(=O)OC)COCCC(=O)OC)NC(=O)CCCNC(=O)OC(C)(C)C]

Boc-[9]-acid
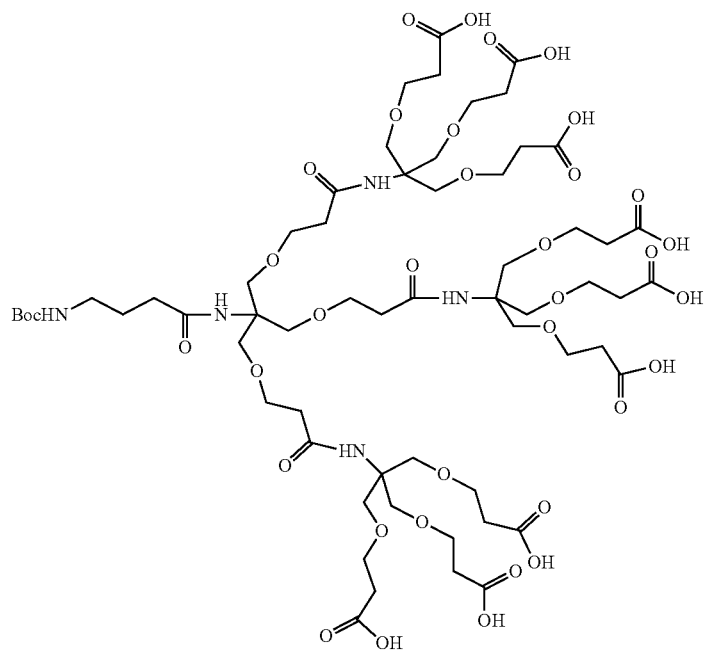 [SMILES: CC(C)(C)OC(=O)NCCCC(=O)NC(COCCC(=O)NC(COCCC(=O)O)(COCCC(=O)O)COCCC(=O)O)(COCCC(=O)NC(COCCC(=O)O)(COCCC(=O)O)COCCC(=O)O)COCCC(=O)NC(COCCC(=O)O)(COCCC(=O)O)COCCC(=O)O]
Ns-[9]-ester
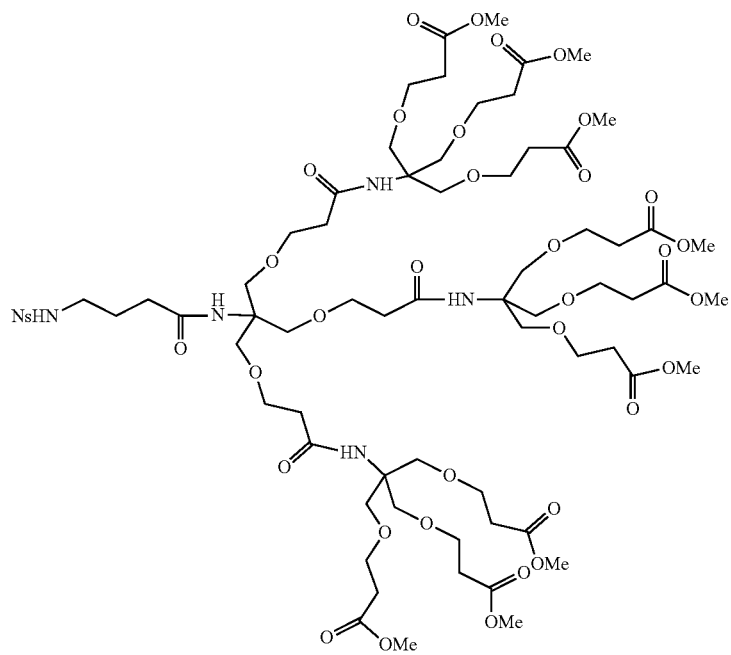

Ns-[9]-acid
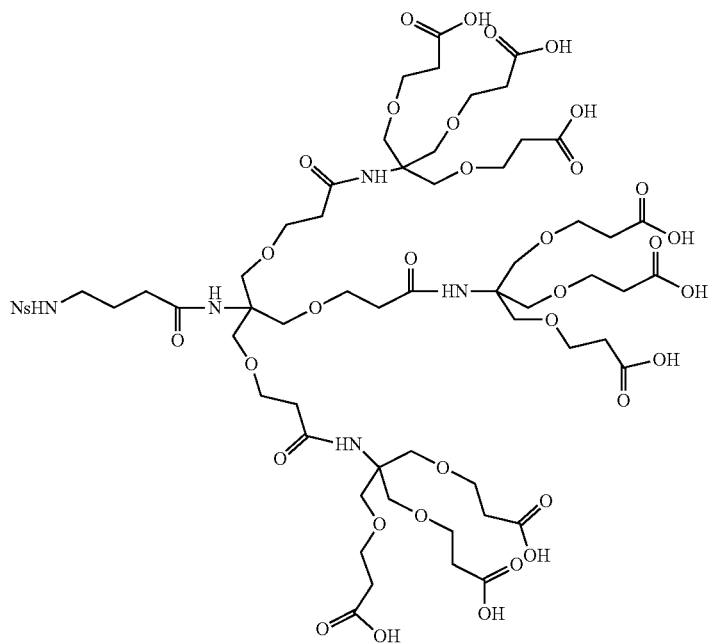
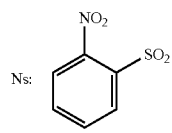
Fmoc-[9]-ester (R=t-butyl)
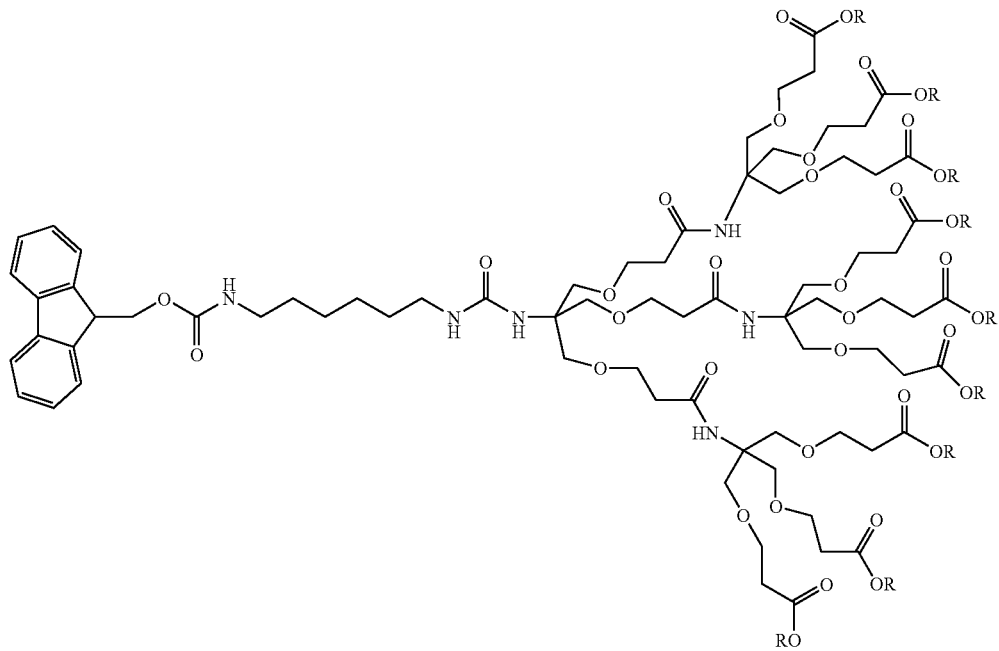

Fmoc-[9]-acid
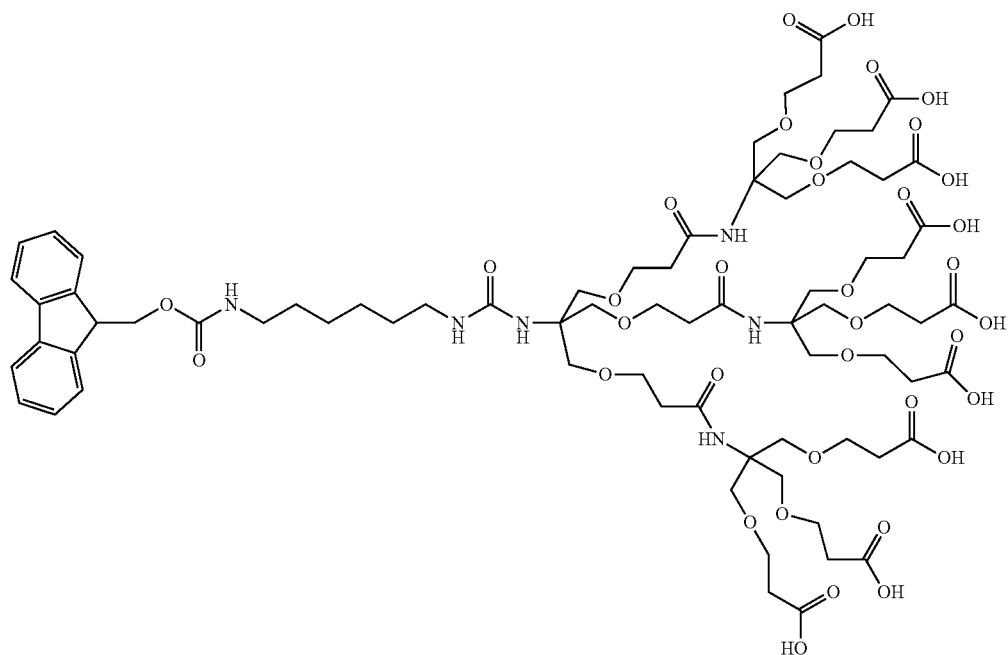 [SMILES: O=C(O)CCOCC(COCCC(=O)O)(COCCC(=O)O)NC(=O)CCOCC(COCCC(=O)NC(COCCC(=O)O)(COCCC(=O)O)COCCC(=O)O)(COCCC(=O)NC(COCCC(=O)O)(COCCC(=O)O)COCCC(=O)O)NC(=O)NCCCCCCNC(=O)OCC1c2ccccc2-c2ccccc21]
AE-[1]-acid
AE-[3]-acid
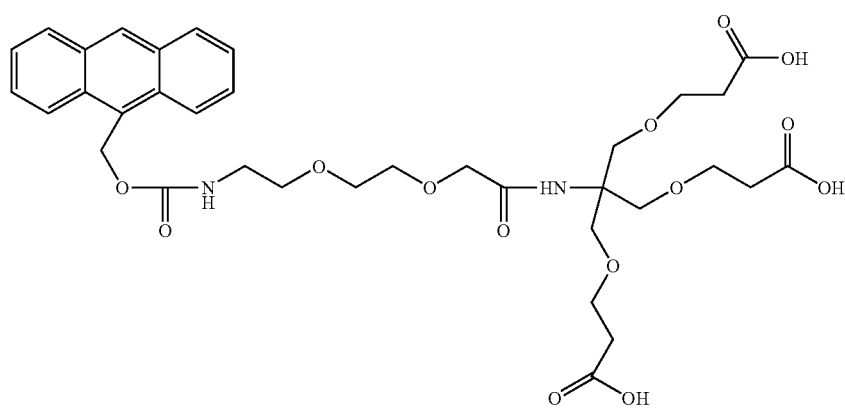 [SMILES: O=C(O)CCOCC(COCCC(=O)O)(COCCC(=O)O)NC(=O)COCCOCCNC(=O)OCc1c2ccccc2cc2ccccc12]

AE-[9]-acid
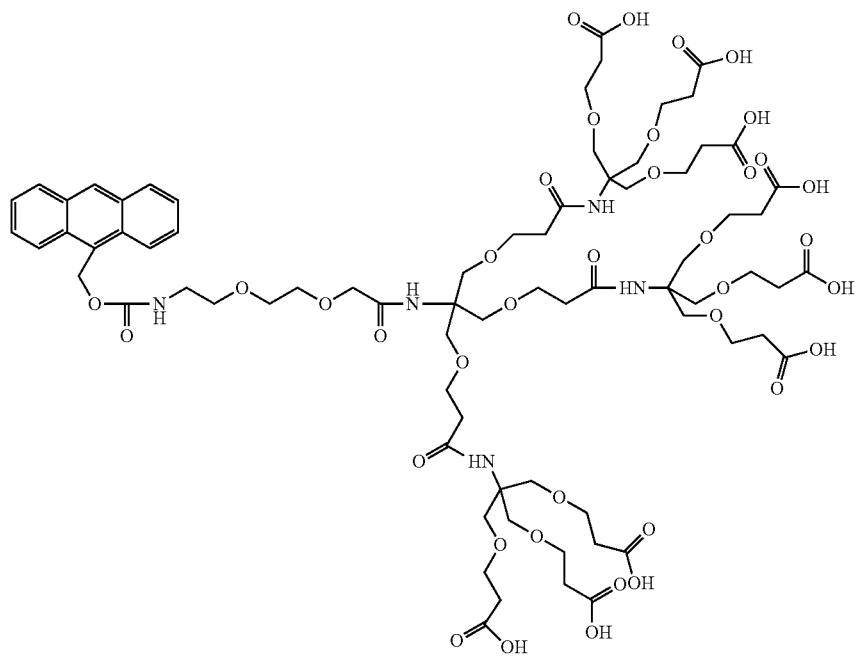 [SMILES: O=C(O)CCOCC(COCCC(=O)O)(COCCC(=O)O)NC(=O)CCOCC(COCCC(=O)NC(COCCC(=O)O)(COCCC(=O)O)COCCC(=O)O)(COCCC(=O)NC(COCCC(=O)O)(COCCC(=O)O)COCCC(=O)O)NC(=O)COCCOCCNC(=O)OCc1c2ccccc2cc2ccccc12]
A-[6]-acid
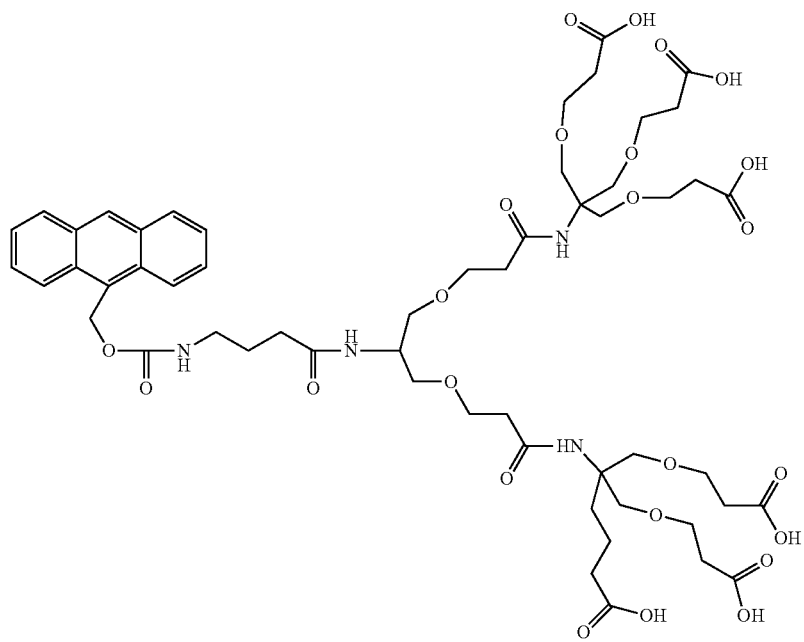

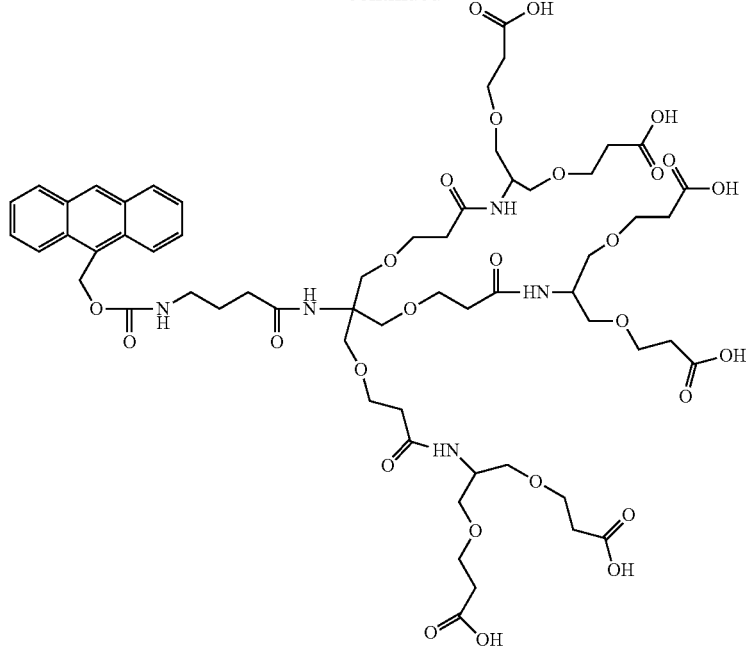
A-[8]-Acid
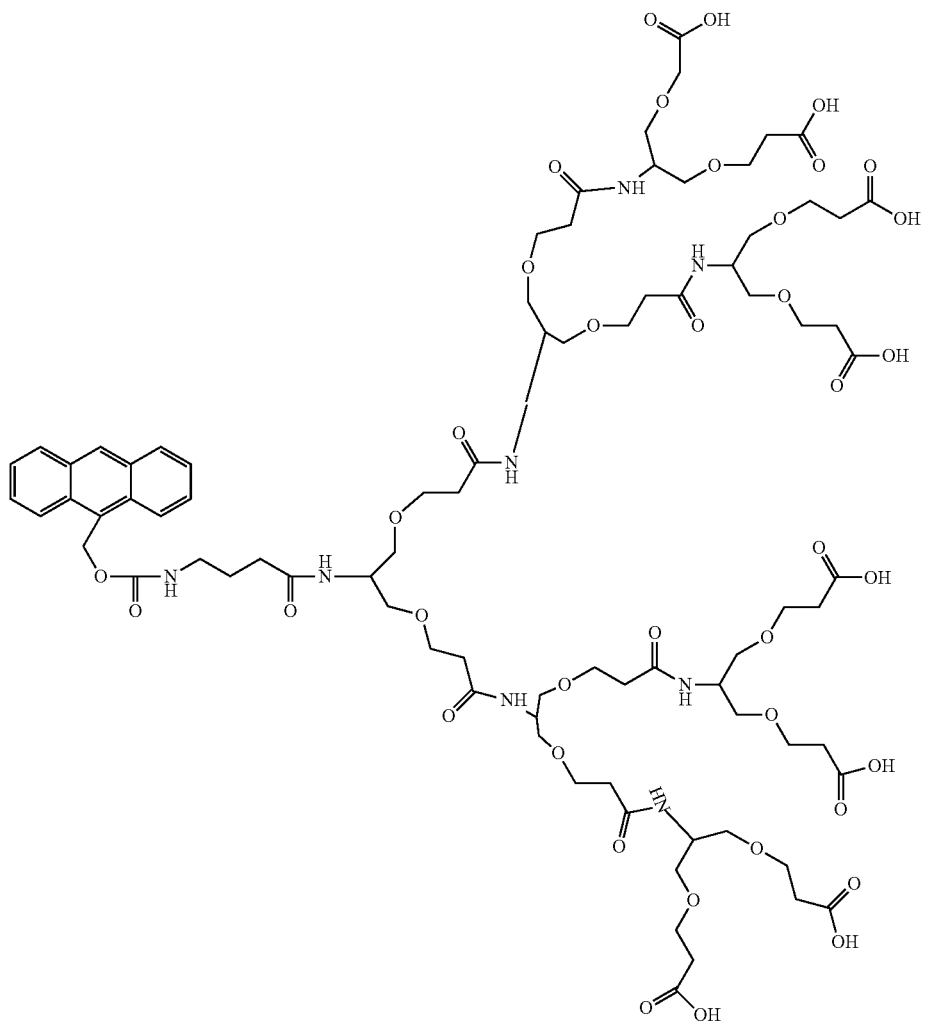

A-[12]-Acid
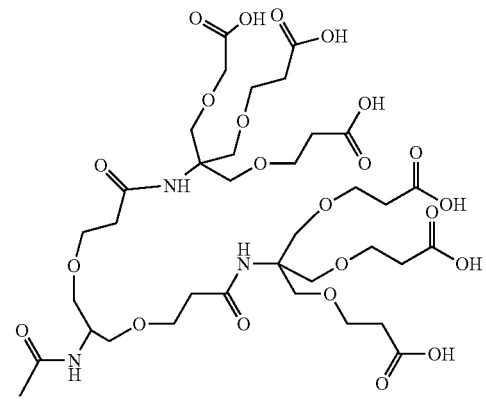
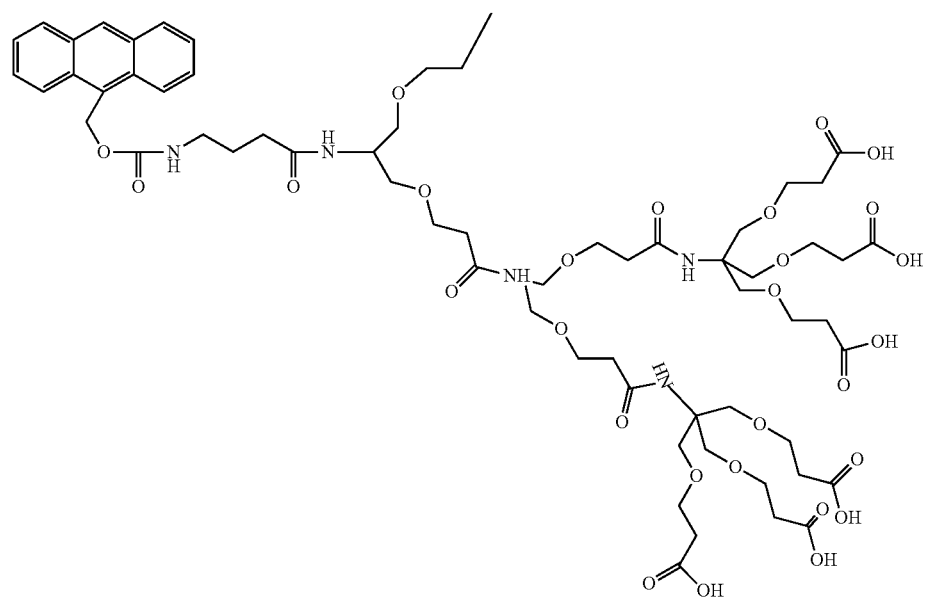
A-[16]-Acid
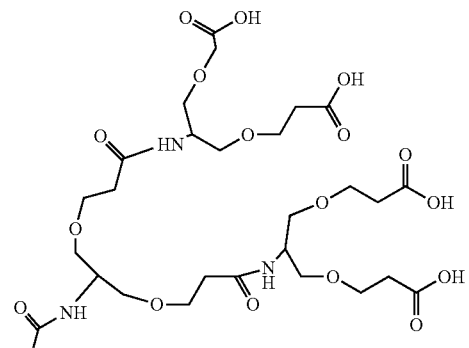

-continued
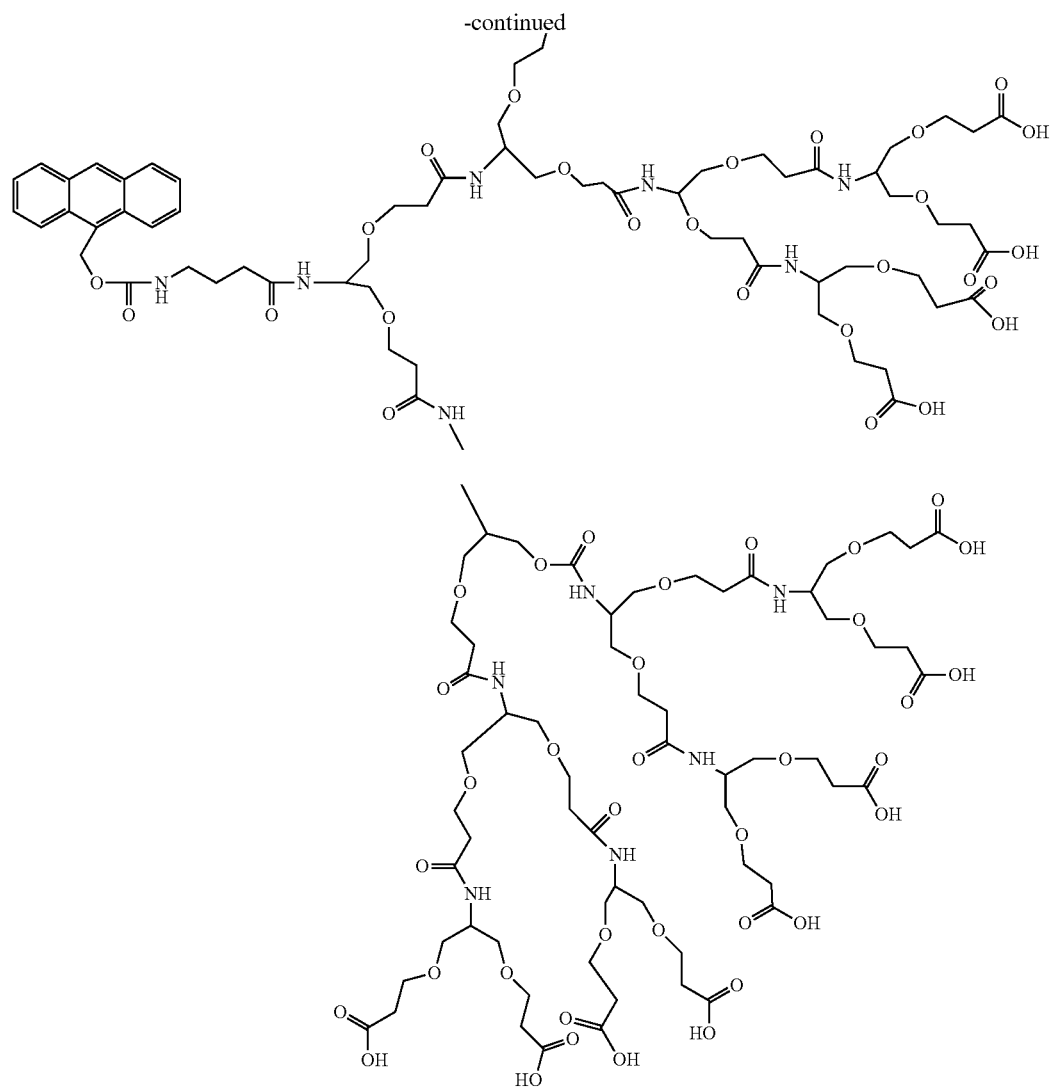
A-[18]-Acid
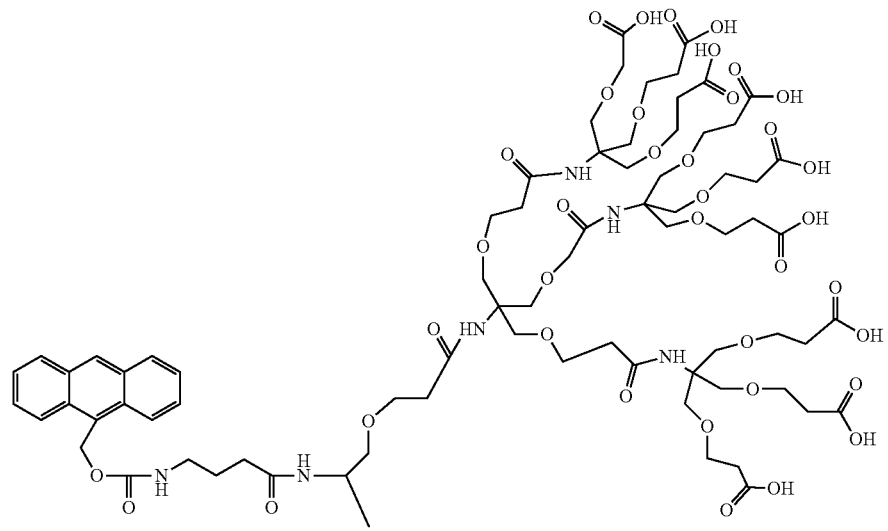

-continued
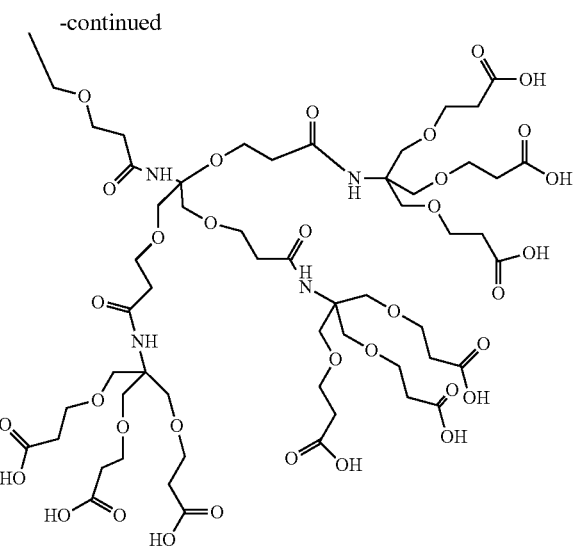
G. R. Newkome *J. Org Chem.* 1985, 50, 2003
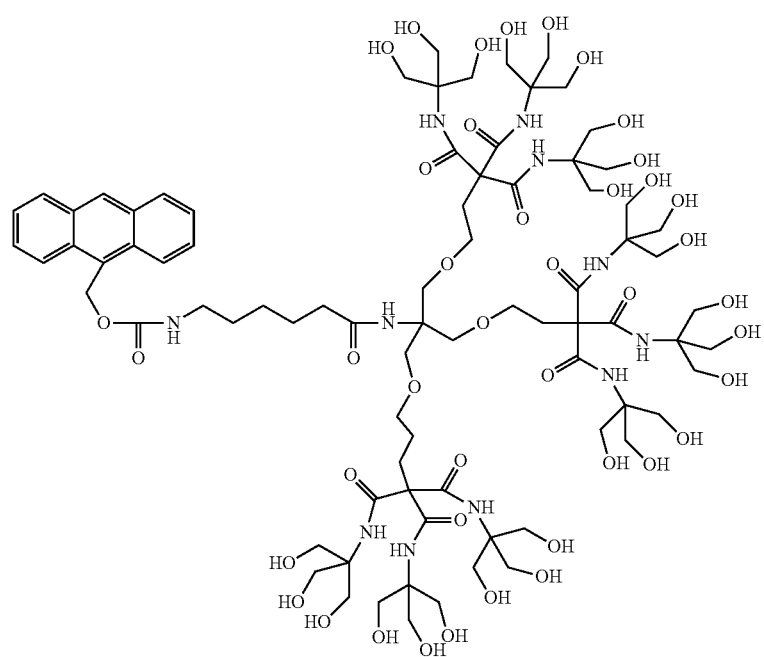 [SMILES: O=C(CCCCCNC(=O)OCc1c2ccccc2cc2ccccc12)NC(COCCCC(C(=O)NC(CO)(CO)CO)(C(=O)NC(CO)(CO)CO)C(=O)NC(CO)(CO)CO)(COCCC(C(=O)NC(CO)(CO)CO)(C(=O)NC(CO)(CO)CO)C(=O)NC(CO)(CO)CO)COCCC(C(=O)NC(CO)(CO)CO)(C(=O)NC(CO)(CO)CO)C(=O)NC(CO)(CO)CO]

J.-J. Lee *Macromolecules* 1994, 27, 4632
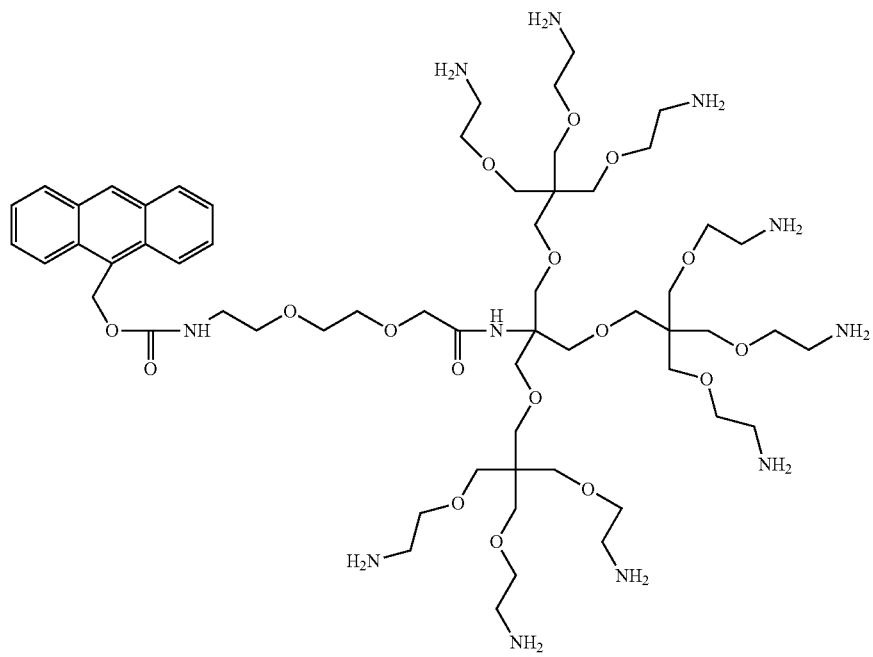 [SMILES: NCCOCC(COCCN)(COCCN)COCC(COCC(COCCN)(COCCN)COCCN)(COCC(COCCN)(COCCN)COCCN)NC(=O)COCCOCCNC(=O)OCc1c2ccccc2cc2ccccc12]
L. J. Twyman *Tetrahedron Lett.* 1994, 35, 4423
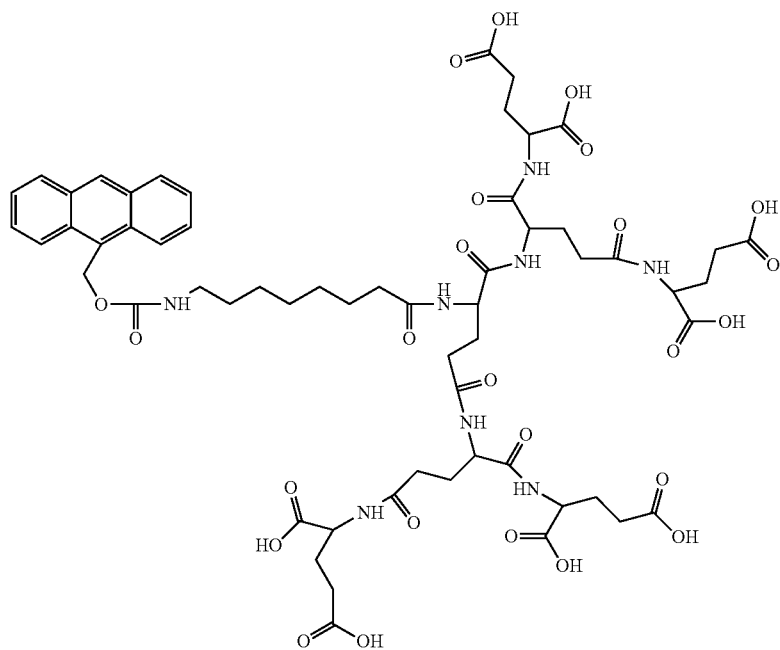 [SMILES: O=C(O)CCC(NC(=O)CCC(NC(=O)CCC(NC(=O)CCCCCCCNC(=O)OCc1c2ccccc2cc2ccccc12)C(=O)NC(CCC(=O)NC(CCC(=O)O)C(=O)O)C(=O)NC(CCC(=O)O)C(=O)O)C(=O)NC(CCC(=O)O)C(=O)O)C(=O)O]

D. A. Tomalia *Polym. J.* 1985, 17, 117
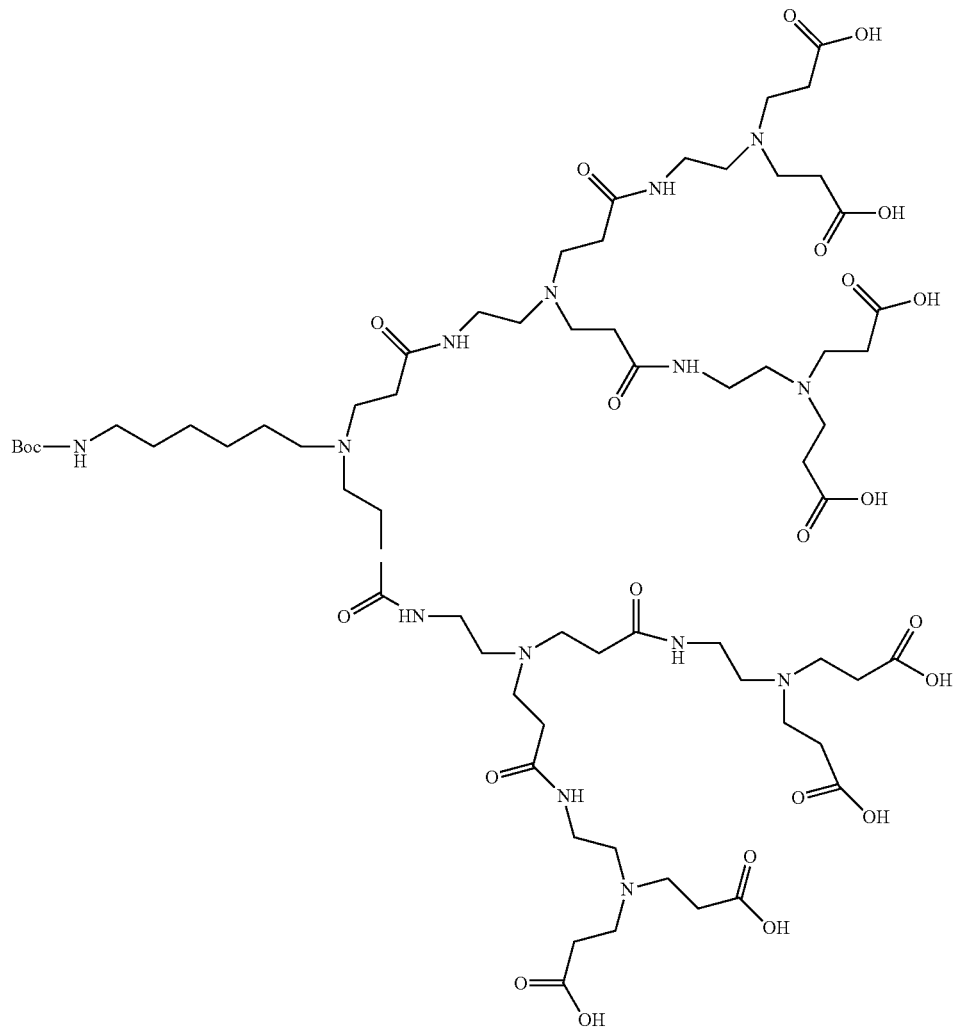 [SMILES: CC(C)(C)OC(=O)NCCCCCCN(CCC(=O)NCCN(CCC(=O)NCCN(CCC(=O)O)CCC(=O)O)CCC(=O)NCCN(CCC(=O)O)CCC(=O)O)CCC(=O)NCCN(CCC(=O)NCCN(CCC(=O)O)CCC(=O)O)CCC(=O)NCCN(CCC(=O)O)CCC(=O)O]

E. Buhleier. *Synthesis* 1978, 155
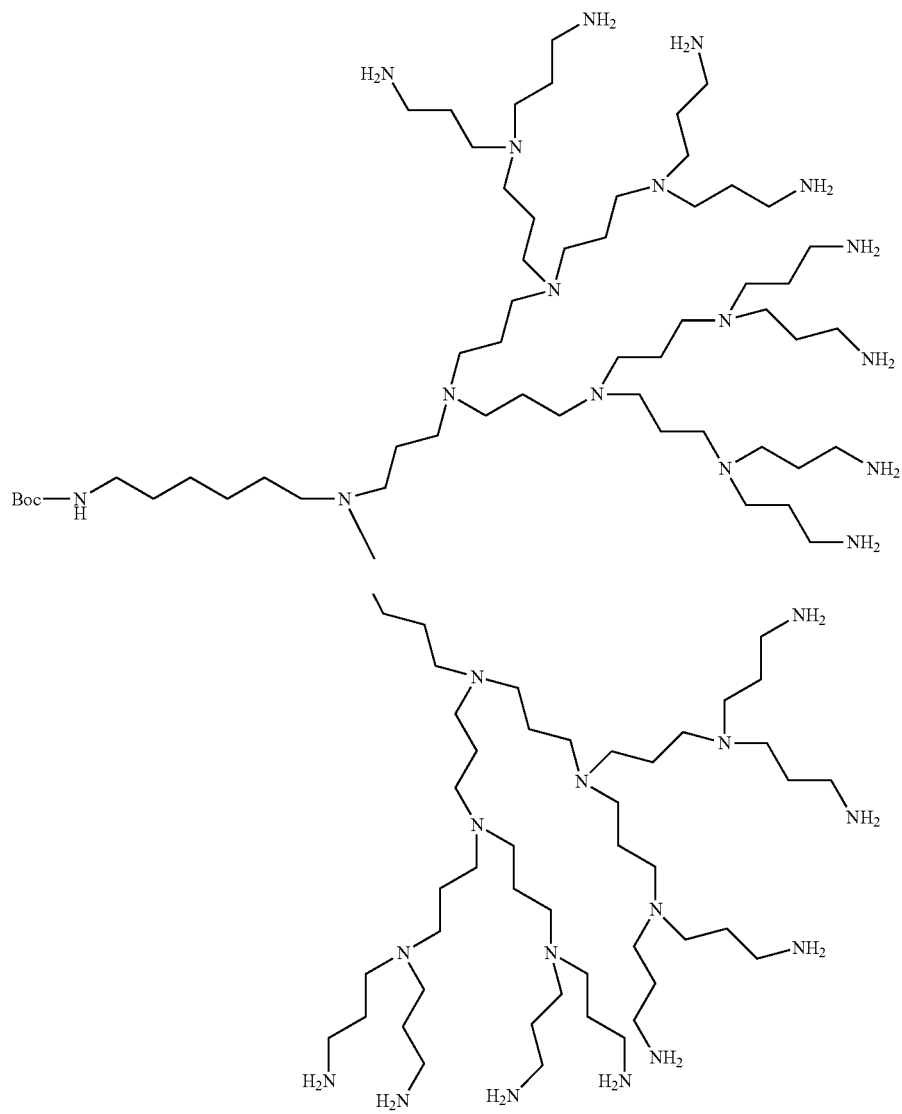
A. W. van der Made *J. Chem. Soc., Chem. Commun.* 1992, 1400
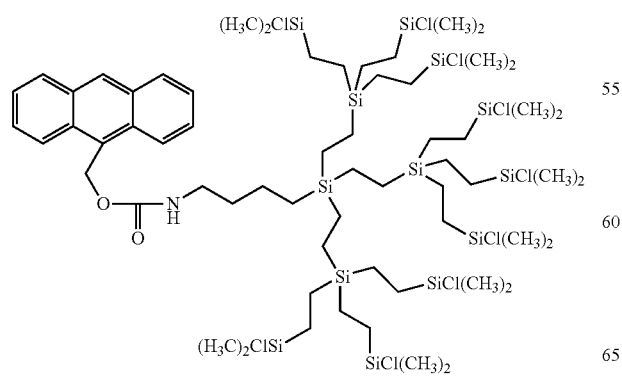

G. R. Newkome *Angew. Chem. Int. Ed. Engl.* 1991, 30, 1176
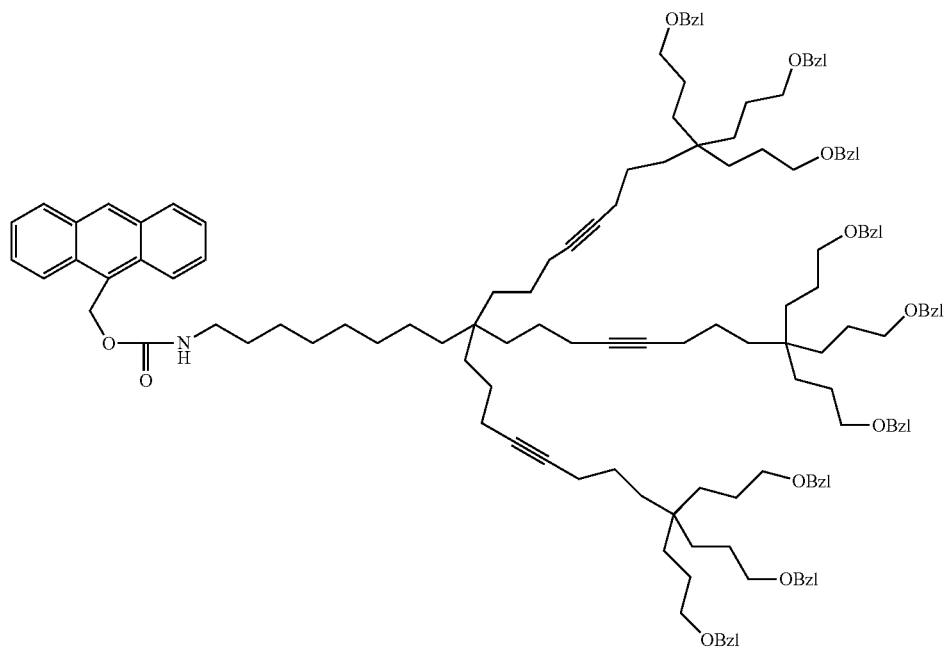
G. R. Newkome Angew. Chem. Int. Ed. Engl. 1991, 30, 1176
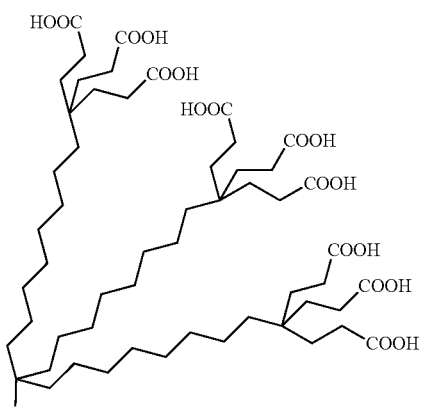

-continued
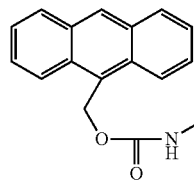
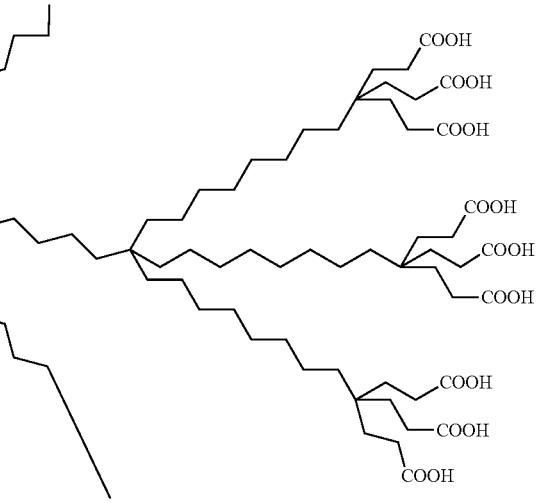
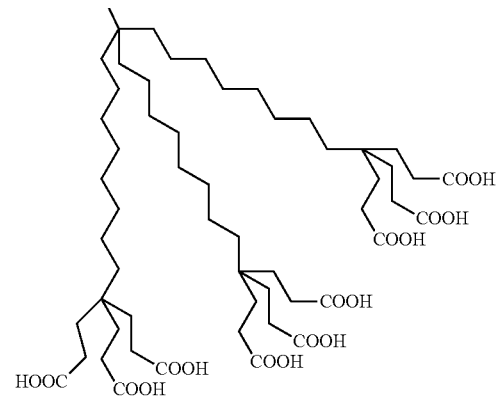
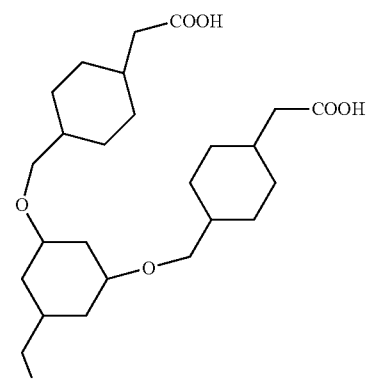

-continued
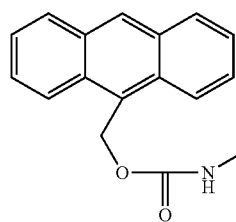
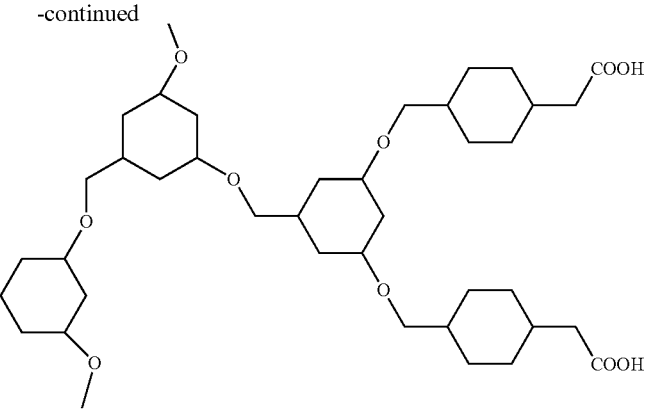
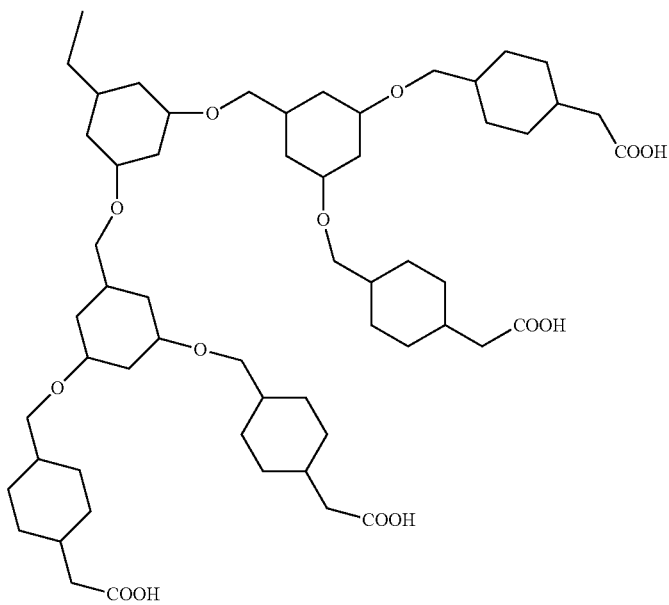
K. L. Wooley *J. Chem. Soc., Perkin Trans.1* 1991, 1059
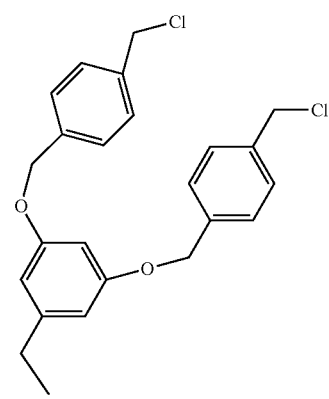

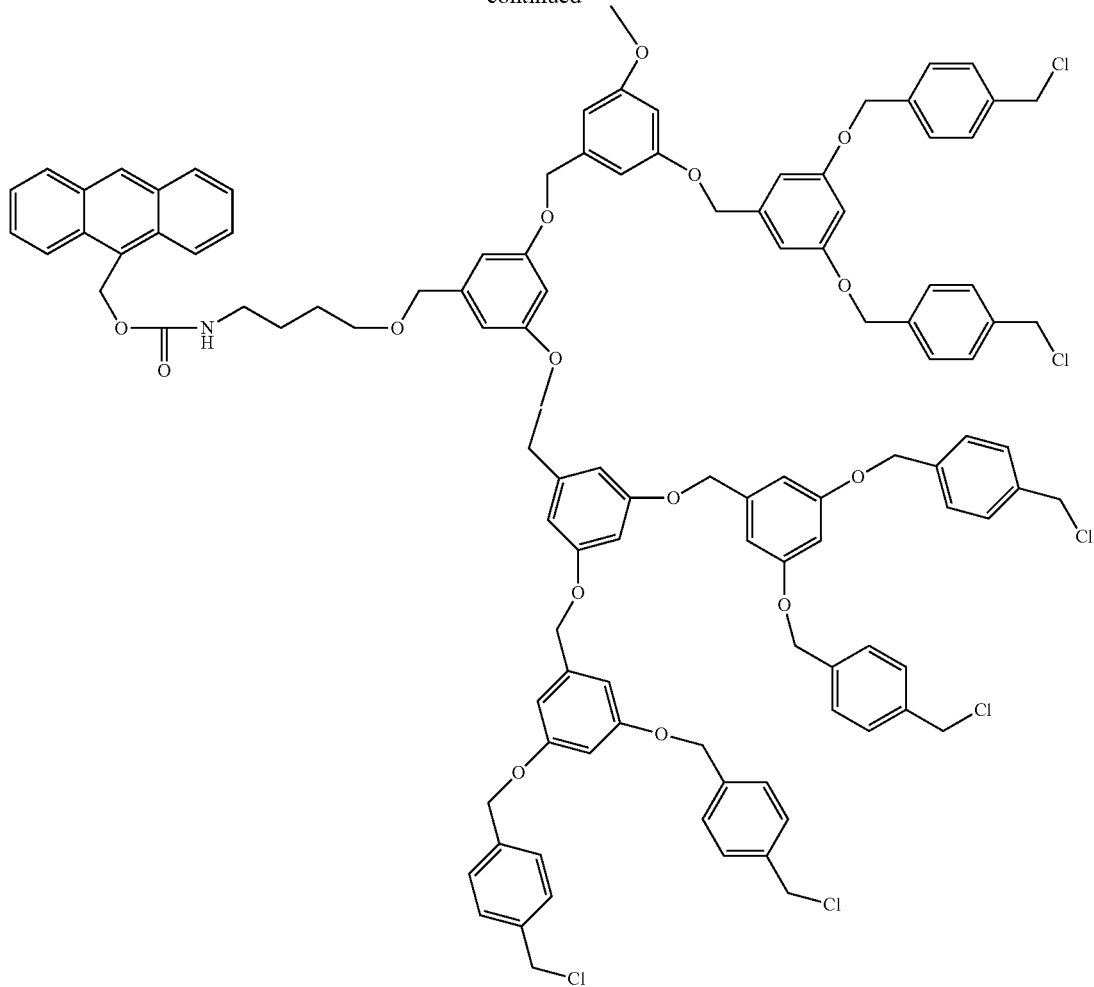
Example 3.1
Preparation Methods
1. A-[3]-OEt (3)
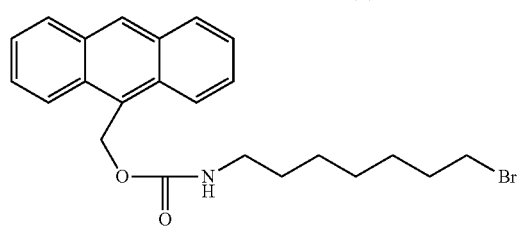
2. A-[3]-OMe (5)
Compound 1 reacted with NaC(CO$_2$Et)$_3$ 2 in C$_6$H$_6$/DMF at 80° C.
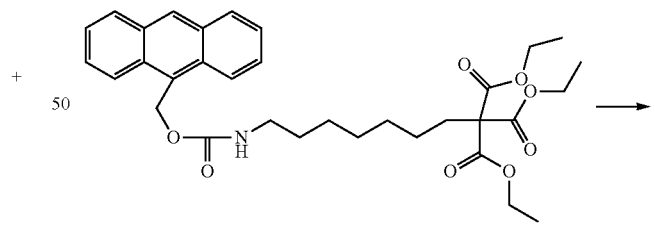
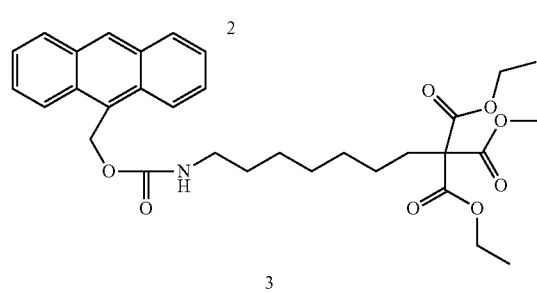
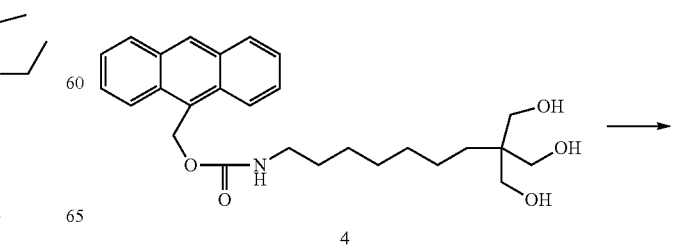

-continued
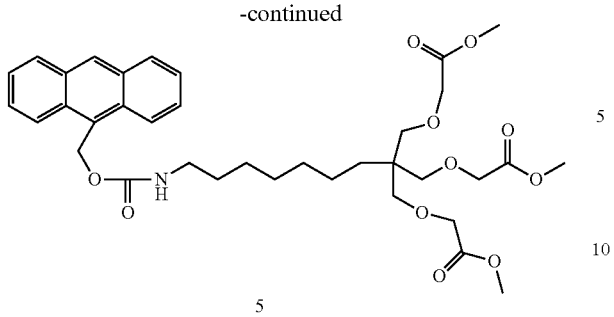
5
A-[3]-OEt 3 was reduced with LiAlH₄ or LiBH₄ in ether, reacted with chloroacetic acid in the presence of t-BuOK/t-BUOH, and esterified with MeOH.
3. A-[3]-OTs (7)
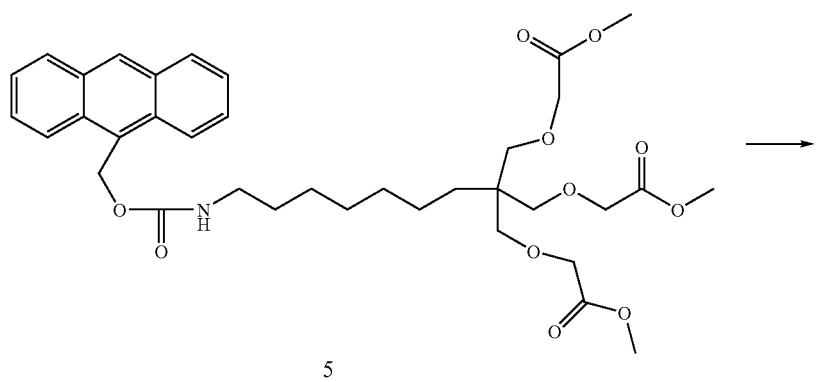
5
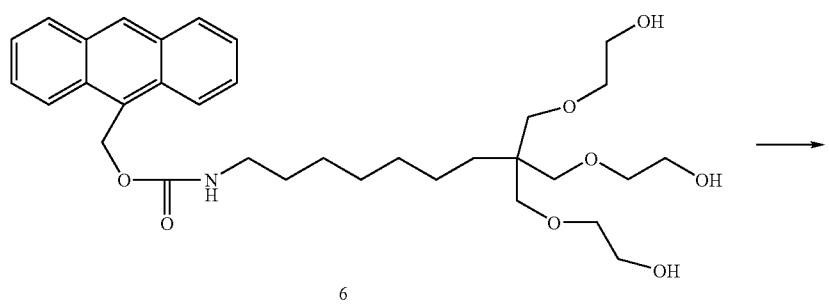
6
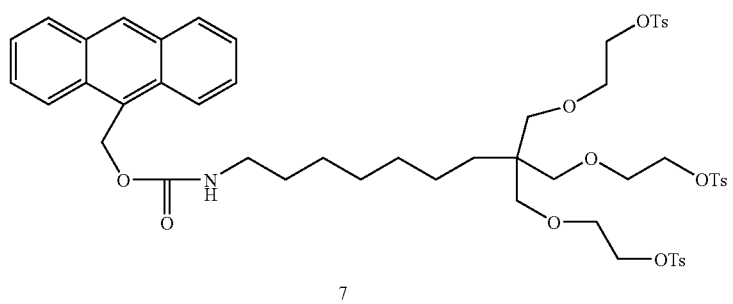
7

Reduction of A-[3]-OMe 5 with LiAlH₄ in ether yields triol compound 6, which is tosylated to compound 7.
4. A-[9]-OEt (8)
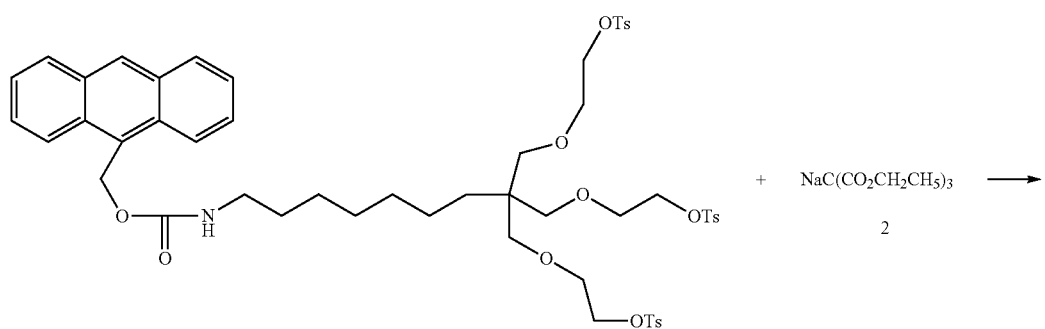
7
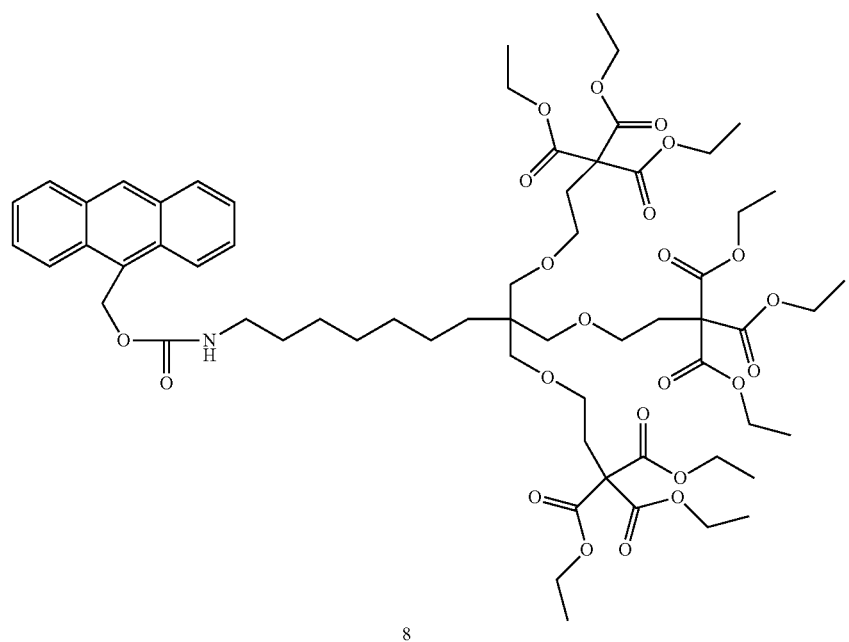
8

A-[3]-OTs 7 was treated with NaC(CO$_2$Et)$_3$ in C$_6$H$_6$-DMF to afford the desired nonaester (compound 8)
5. A-[27]-OH (9)
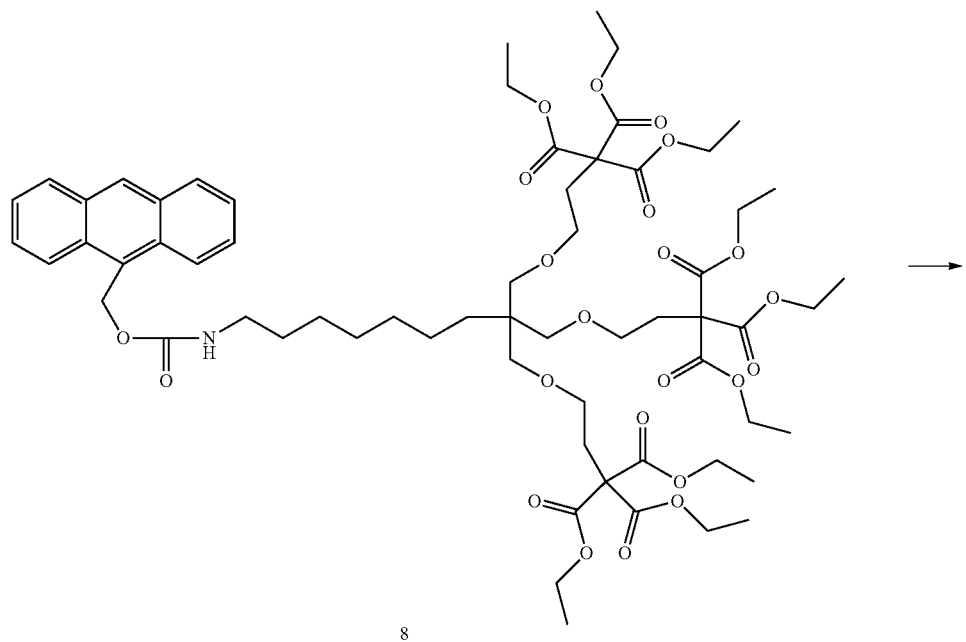
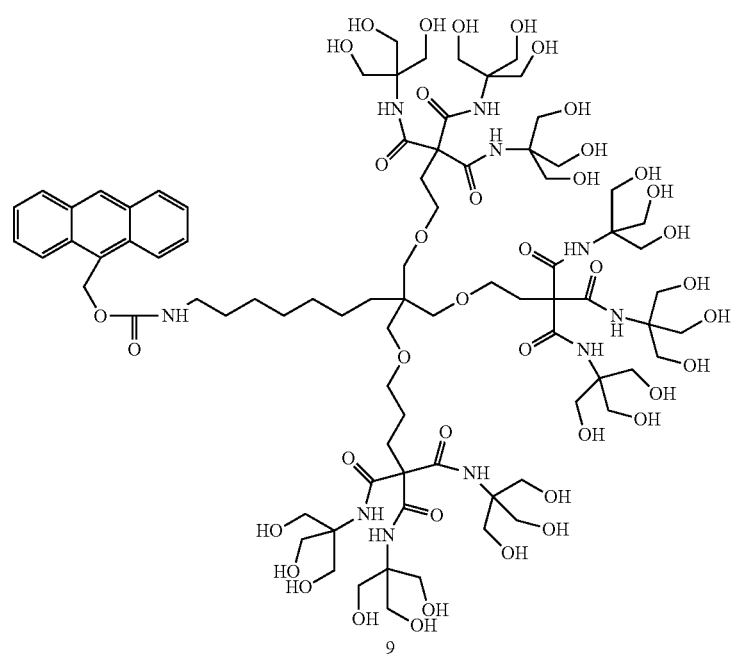

A-[9]-OEt 8 was treated with tris(hydroxymethyl)aminomethane and $K_2CO_3$ in DMSO at 70° C.

Example 3.2

1. Boc-[2]-OMe (3)

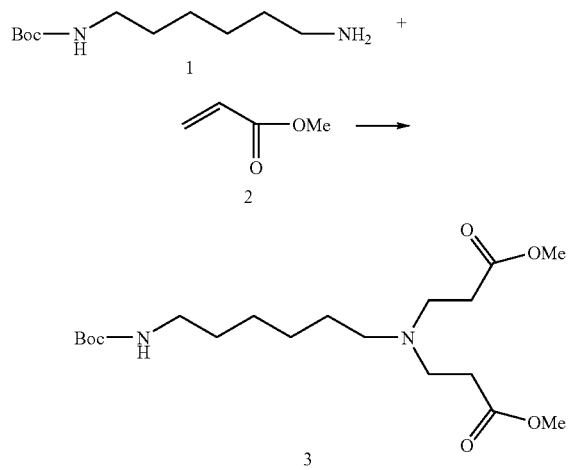

Compound 1 was reacted with methyl acrylate 2 in methanol solvent at temperature below 50° C. Excess reagents and solvent were removed under high vacuum at temperature below 55° C.

2. Boc-[4]-NH$_2$ (5)

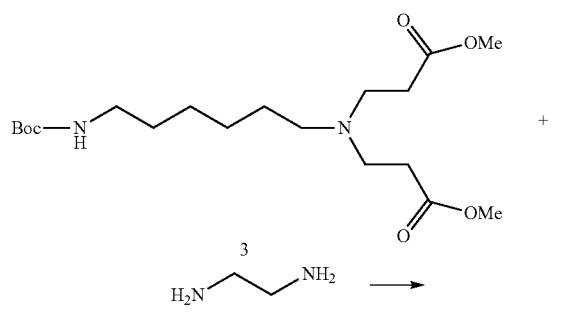

Boc-[2]-OMe 3 was reacted with large excesses of ethylenediamine (EDA) 4 in methanol solvent temperature below 50° C. Excess reagents and solvent were removed under high vacuum at temperature below 55° C.

3. Boc-[8]-OMe (6)

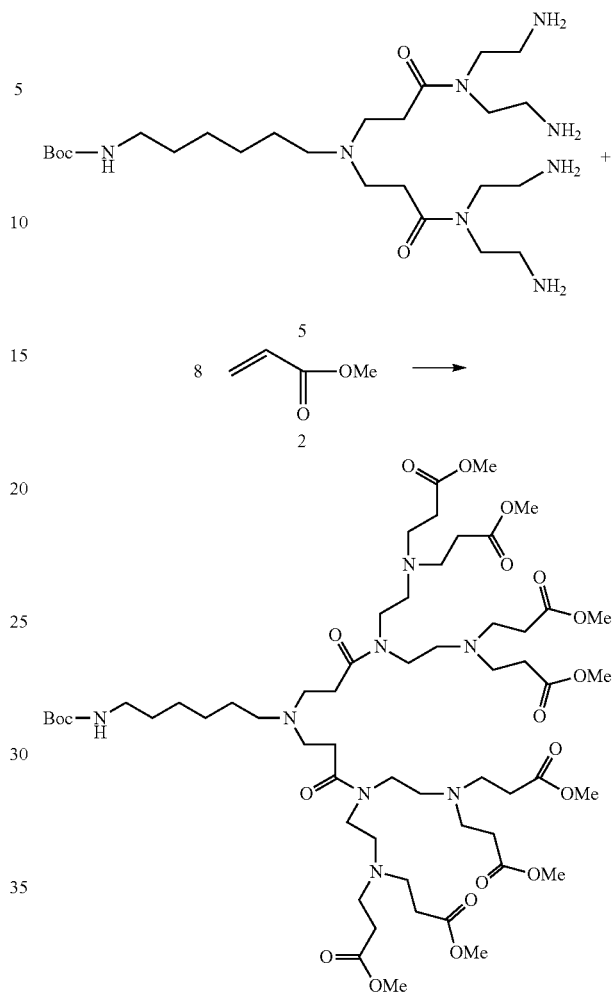

Boc-[4]-NH$_2$ 5 was reacted with methyl acrylate 2 in methanol solvent at temperature below 50° C. Excess reagents and solvent were removed under high vacuum at temperature below 55° C.

Example 3.3

1. Boc-[2]-OH (3)

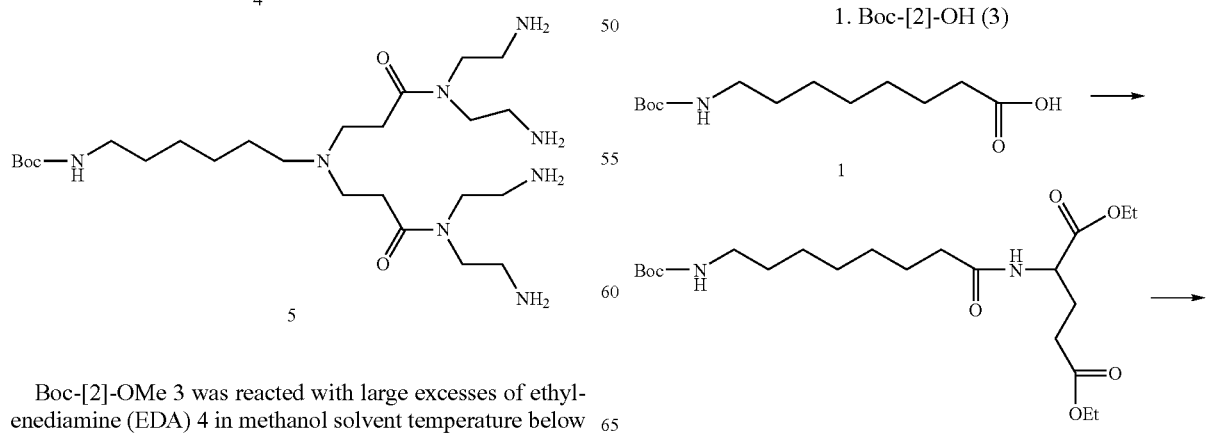

-continued

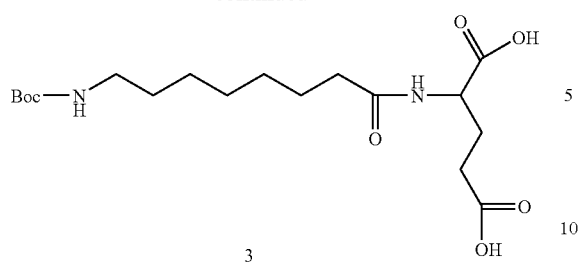

3

Compound 1, 1-[3-(dimethylamino)propyl]-3-ethylcarbodiimide hydrochloride (EDC), and 1-hydroxybenzotriazole hydrate (HOBT) were dissolved in acetonitrile and stirred at room temperature. L-glutamic acid-diethyl ester ($H_2NCH(CO_2Et)CH_2CH_2CO_2Et$) dissolved in acetonitrile was added with stirring, After stirring at room temperature for 12 h, the acetonitrile was evaporated. The crude product was dissolved in EA and washed with 1.0 N HCl and saturated sodium bicarbonate solution. After being dried with anhydrous $MgSO_4$, filtered, and evaporated, the crude product was loaded in a column packed with silica gel. Purification by column chromatography (eluent: ethyl acetate:haxane) resulted in a viscous yellow liquid.

Compound 2 was hydrolyzed by NaOH solution. After being stirred at room temperature for 1 d, the organic liquid was evaporated. The aqueous solution was washed with EA, stirred in an ice bath and acidified with dilute HCl. After the product was extracted with EA, the organic solution was dried with anhydrous $MgSO_4$, filtered and evaporated.

2. Boc-[4]-OH (3)

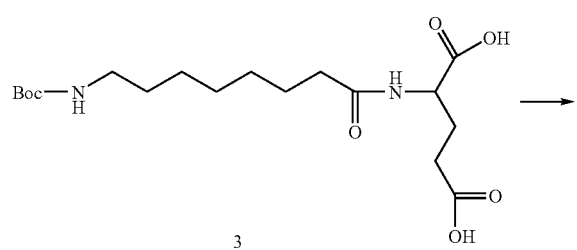

3

-continued

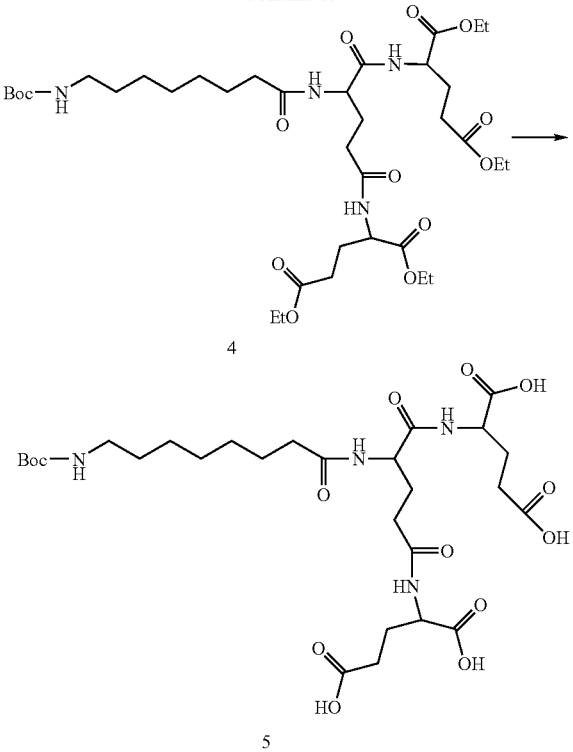

4

5

Compound 3, 1-[3-(dimethylamino)propyl]-3-ethylcarbodiimide hydrochloride (EDC), and 1-hydroxybenzotriazole hydrate (HOBT) were dissolved in acetonitrile and stirred at room temperature. L-glutamic acid-diethyl ester ($H_2NCH(CO_2Et)CH_2CH_2CO_2Et$) dissolved in acetonitrile was added with stirring, After stirring at room temperature for 12 h, the acetonitrile was evaporated. The crude product was dissolved in EA and washed with 1.0 N HCl and saturated sodium bicarbonate solution. After being dried with anhydrous $MgSO_4$, filtered, and evaporated, the crude product was loaded in a column packed with silica gel. Purification by column chromatography (eluent: ethyl acetate:haxane) resulted in a viscous yellow liquid.

Compound 4 was hydrolyzed by NaOH solution. After being stirred at room temperature for 1 d, the organic liquid was evaporated. The aqueous solution was washed with EA, stirred in an ice bath and acidified with dilute HCl. After the product was extracted with EA, the organic solution was dried with anhydrous $MgSO_4$, filtered and evaporated.

3. Boc-[8]-OH (3)

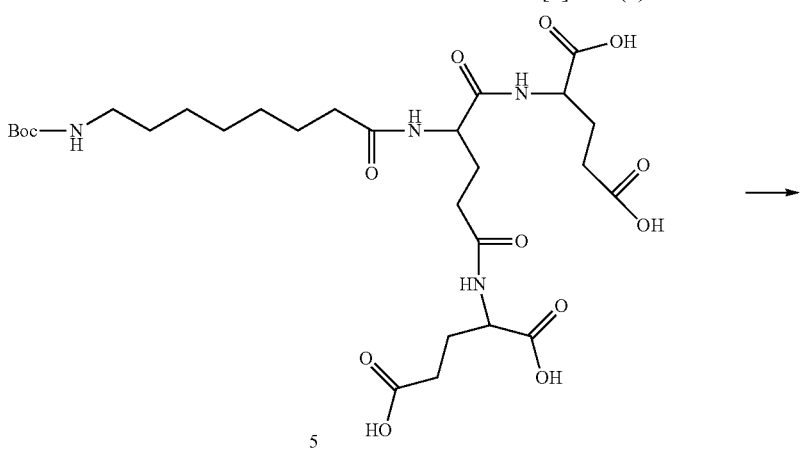

5

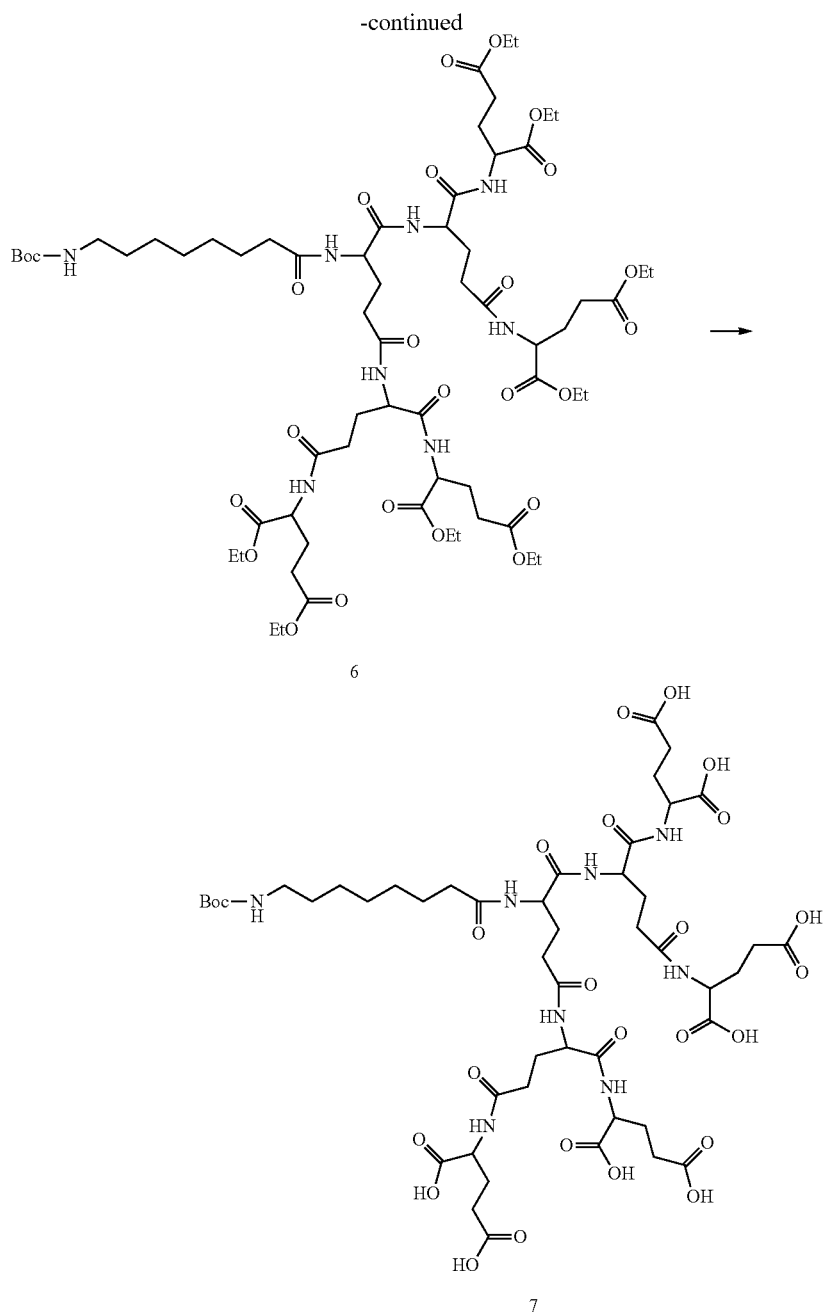

6

7

Compound 5, 1-[3-(dimethylamino)propyl]-3-ethylcarbodiimide hydrochloride (EDC), and 1-hydroxybenzotriazole hydrate (HOBT) were dissolved in acetonitrile and stirred at room temperature. L-glutamic acid-diethyl ester ($H_2NCH(CO_2Et)CH_2CH_2CO_2Et$) dissolved in acetonitrile was added with stirring, After stirring at room temperature for 12 h, the acetonitrile was evaporated. The crude product was dissolved in EA and washed with 1.0 N HCl and saturated sodium bicarbonate solution. After being dried with anhydrous $MgSO_4$, filtered, and evaporated, the crude product was loaded in a column packed with silica gel. Purification by column chromatography (eluent: ethyl acetate:haxane) resulted in a viscous yellow liquid.

Compound 6 was hydrolyzed by NaOH solution. After being stirred at room temperature for 1 d, the organic liquid was evaporated. The aqueous solution was washed with EA, stirred in an ice bath and acidified with dilute HCl. After the product was extracted with EA, the organic solution was dried with anhydrous $MgSO_4$, filtered and evaporated.

Example 3.4

1. Boc-[2]-CN (3)

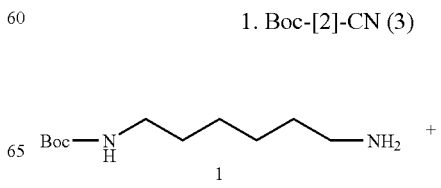

1

-continued

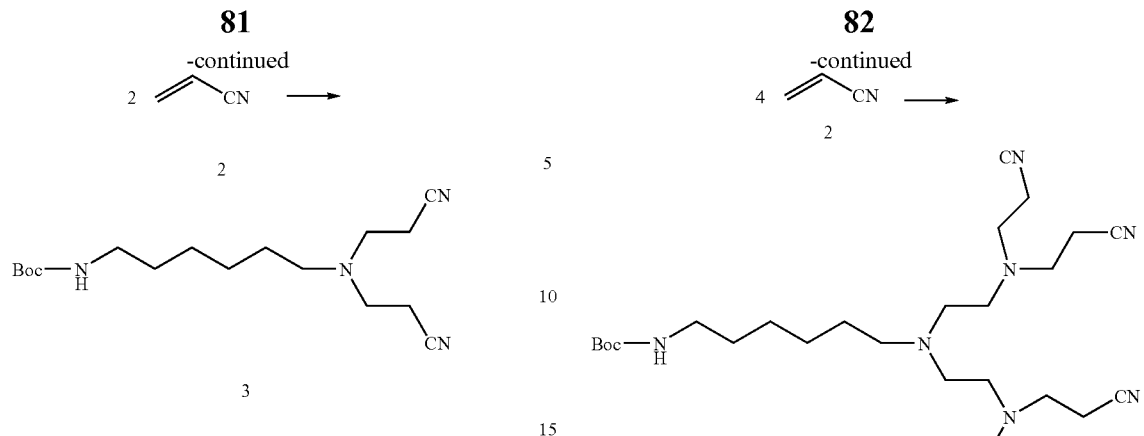

Compound 1 was dissolved at room temp. in acrylonitrile. Glacial acetic acid was added and the solution is heated under reflux for 24 h. Excess acrylonitrile was distilled off under vacuum, the residue was extracted with chloroform, and added to concentrated ammonia solution. The organic phase was separated, washed with water, and dried with sodium sulfate.

2. Boc-[2]-NH₂ (4)

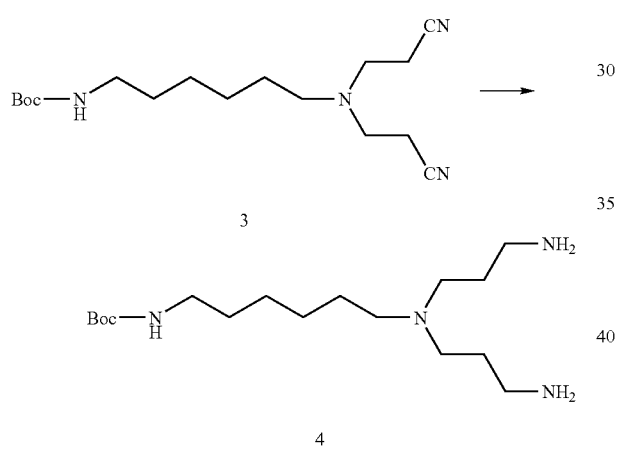

Boc-[2]-CN, 3 was dissolved in methanol and cobalt (II) chloride hexahydrate was added. Sodium borohydride was added in portions. The resultant mixture was stirred for 2 h at room temp. and then cautiously acidified with concentrated hydrochloric acid. The solvent was removed under vacuum and concentrated. The organic phase was separated, washed with water, and dried with sodium sulfate.

3. Boc-[4]-CN (5)

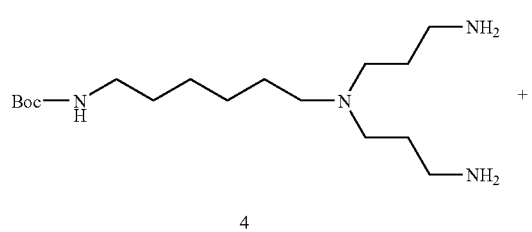

-continued

Boc-[2]-NH₂ 4 was dissolved at room temp. in acrylonitrile. Glacial acetic acid was added and the solution is heated under reflux for 24 h. Excess acrylonitrile was distilled off under vacuum, the residue was extracted with chloroform, and added to concentrated ammonia solution. The organic phase was separated, washed with water, and dried with sodium sulfate.

4. Boc-[4]-NH₂ (6)

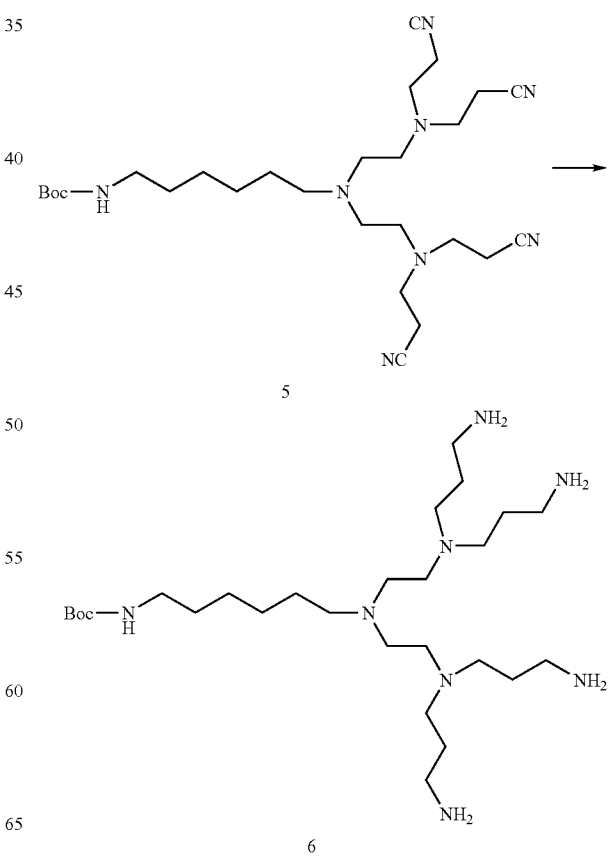

Boc-[4]-CN, 5 was dissolved in methanol and cobalt (II) chloride hexahydrate was added. Sodium borohydride was added in portions. The resultant mixture was stirred for 2 h at room temp. and then cautiously acidified with concentrated hydrochloric acid. The solvent was removed under vacuum and concentrated. The organic phase was separated, washed with water, and dried with sodium sulfate.

and added to concentrated ammonia solution. The organic phase was separated, washed with water, and dried with sodium sulfate.

6. Boc-[8]-NH$_2$ (8)

5. Boc-[8]-CN (7)

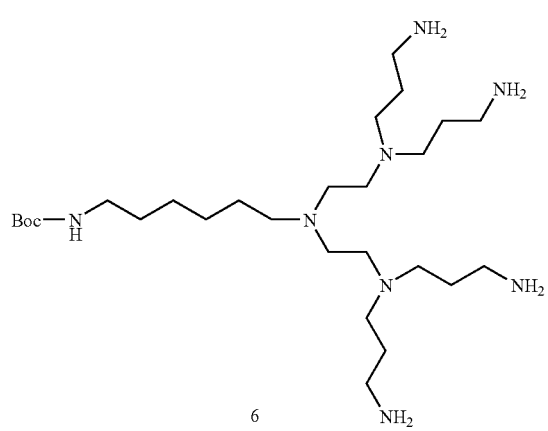

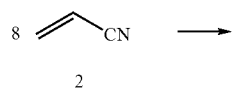

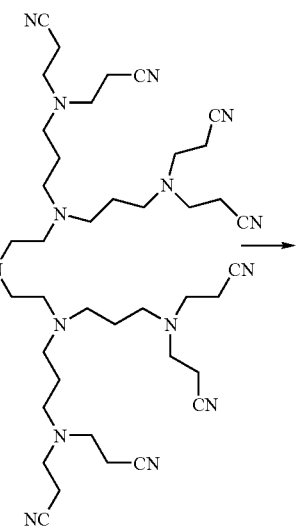

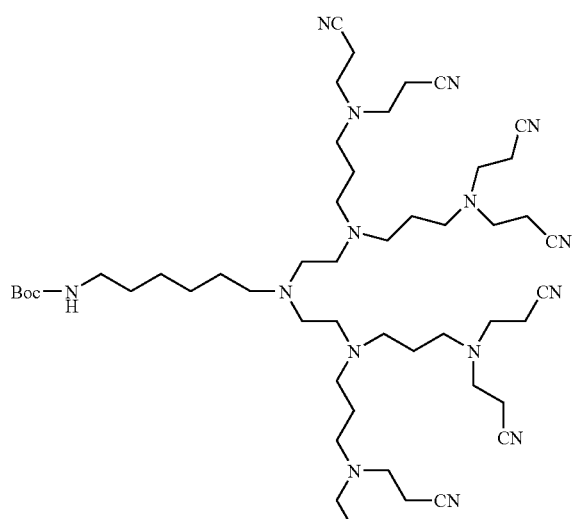

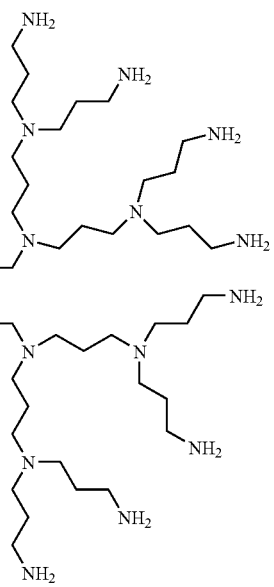

Boc-[4]-NH$_2$ 6 was dissolved at room temp. in acrylonitrile. Glacial acetic acid was added and the solution is heated under reflux for 24 h. Excess acrylonitrile was distilled off under vacuum, the residue was extracted with chloroform, Boc-[8]-CN, 7 was dissolved in methanol and cobalt (II) chloride hexahydrate was added. Sodium borohydride was added in portions. The resultant mixture was stirred for 2 h at room temp. and then cautiously acidified with concentrated hydrochloric acid. The solvent was removed under vacuum and concentrated. The organic phase was separated, washed with water, and dried with sodium sulfate.

7. Boc-[16]-CN (9)
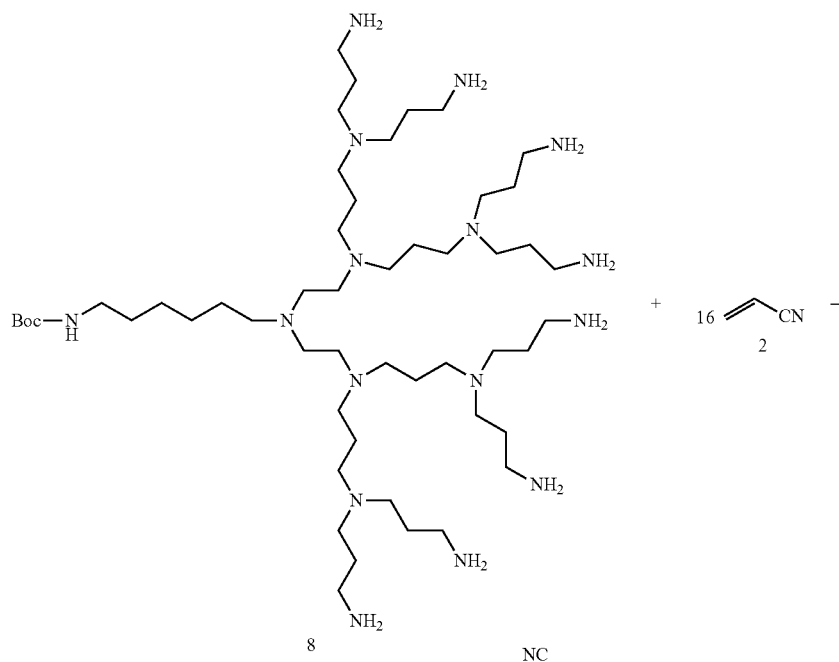

Boc-[8]-NH₂ 8 was dissolved at room temp. in acrylonitrile. Glacial acetic acid was added and the solution is heated under reflux for 24 h. Excess acrylonitrile was distilled off under vacuum, the residue was extracted with chloroform, and added to concentrated ammonia solution. The organic phase was separated, washed with water, and dried with sodium sulfate.
7. Boc-[16]-NH₂ (10)
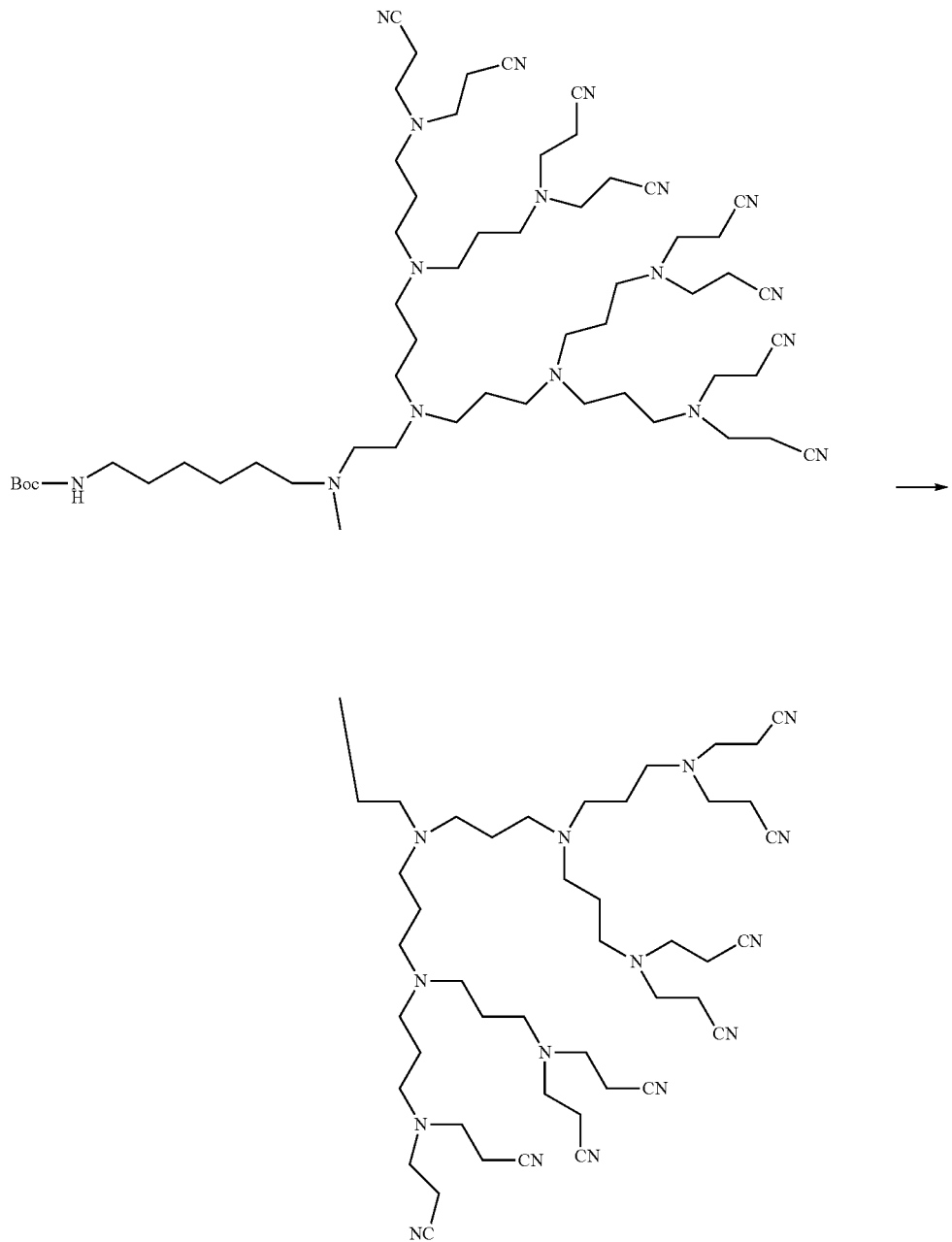
9

-continued
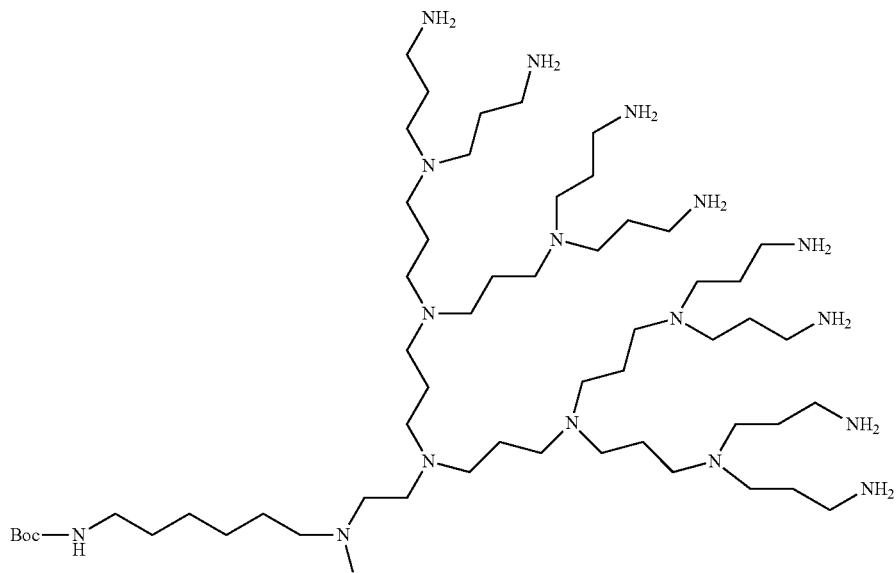
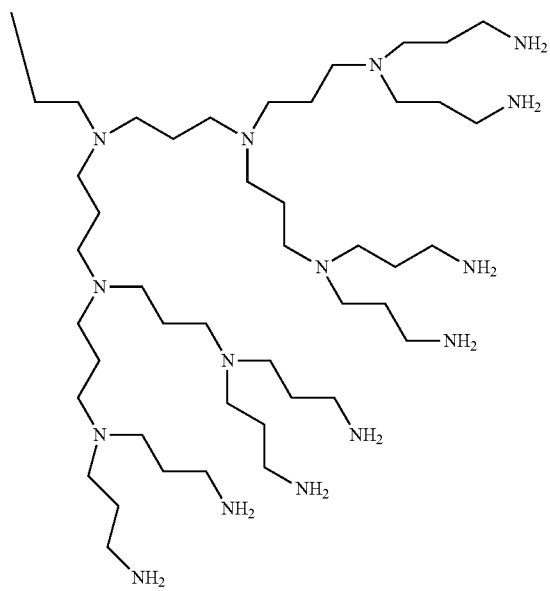
10

Boc-[16]-CN, 9 was dissolved in methanol and cobalt (II) chloride hexahydrate was added. Sodium borohydride was added in portions. The resultant mixture was stirred for 2 h at room temp. and then cautiously acidified with concentrated hydrochloric acid. The solvent was removed under vacuum and concentrated. The organic phase was separated, washed with water, and dried with sodium sulfate.

Example 3.5

1. A-[3]-Alkene (3)

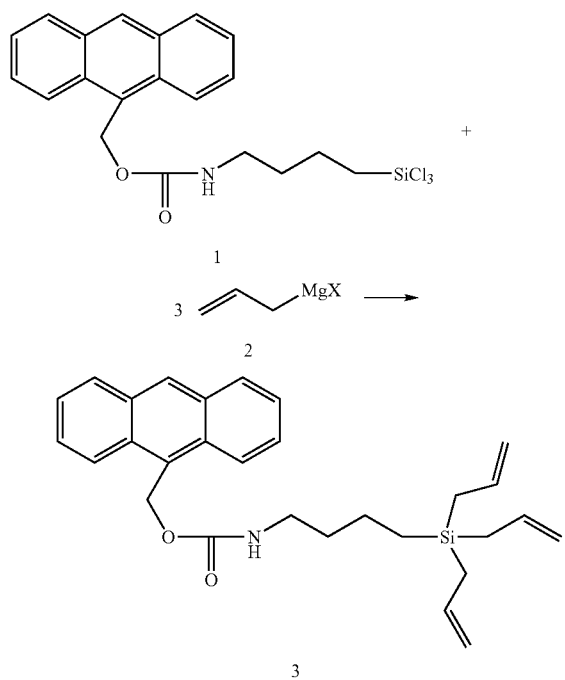

A-[1]-SiCl₃ 1 was refluxed with 10% excess of allylmagnesium bromide in diethyl ether for 4 h, and cooled to 0° C. and hydrolyzed with 10% aqueous NH₄Cl. The organic layer was washed with water, dried MgSO₄ and concentrated.

2. A-[3]-SiCl₃ (4)

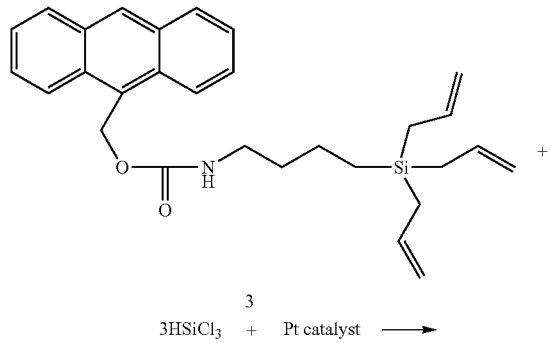

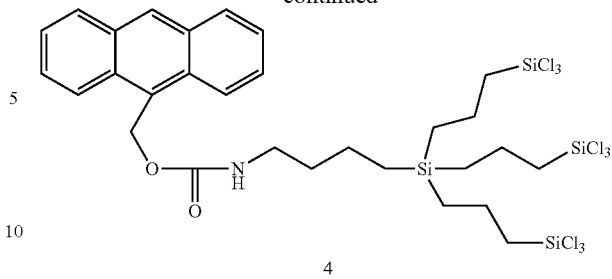

A mixture of A-[3]-Alkene 3, HSiCl₃, and a common platinum-based hydrosilylation catalyst, e.g. H2PtCl6 in propan-2-ol (Speier's catalyst) or platinum divinylsiloxane complecx (Karstedt's catalyst), was stirred for 24 h at room temp. When the reaction was completed, excess HSiCl₃ was removed under vacuum.

3. A-[9]-Alkene (5)

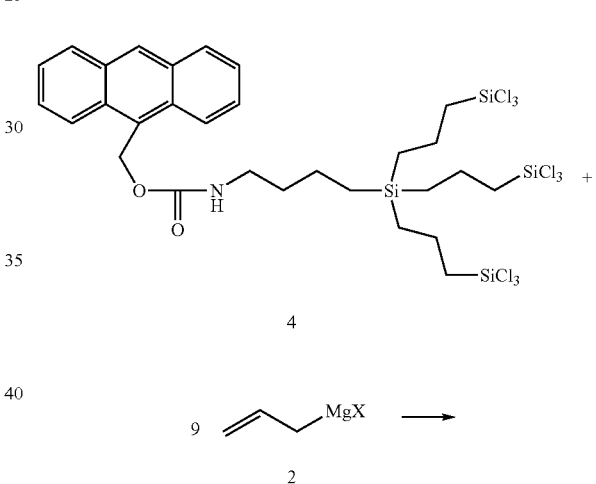

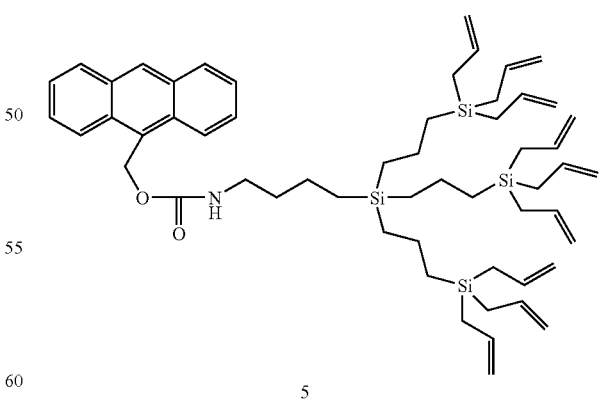

A-[3]-SiCl₃ 4 was refluxed with 10% excess of allylmagnesium bromide in diethyl ether for 4 h, and cooled to 0° C. and hydrolyzed with 10% aqueous NH₄Cl. The organic layer was washed with water, dried MgSO₄ and concentrated.

4. A-[9'-SiCl₃ (6)

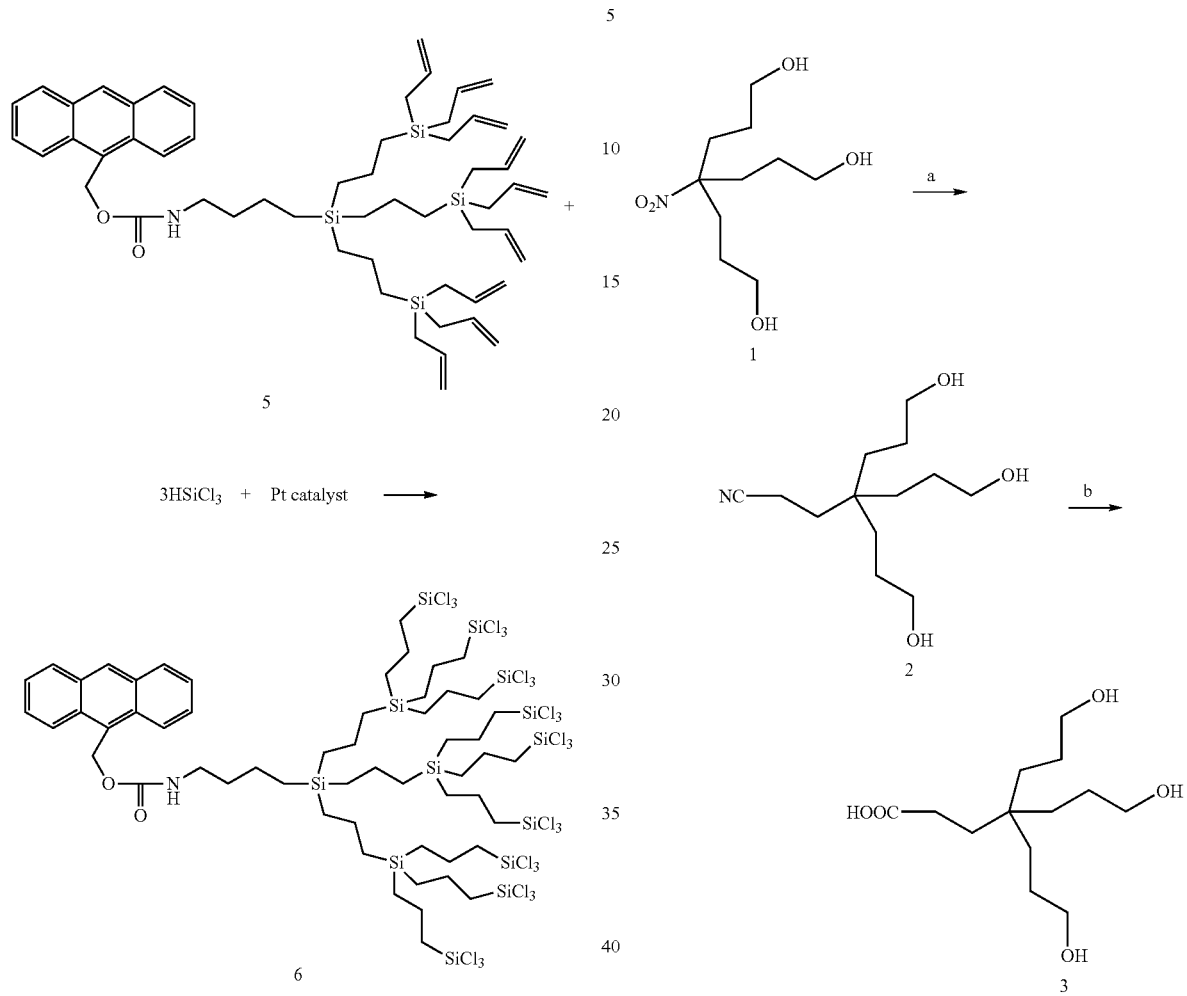

A mixture of A-[9]-Alkene 5, HSiCl₃, and a common platinum-based hydrosilylation catalyst, e.g. H2PtCl6 in propan-2-ol (Speier's catalyst) or platinum divinylsiloxane complecx (Karstedt's catalyst), was stirred for 24 h at room temp. When the reaction was completed, excess HSiCl₃ was removed under vacuum.

Example 3.6

1. [1]-acid-[3]-triol (3)

(a) The triol 1 was cyanoethylated affording the nitrile compound 2. Acrylonitrile, nBu₃SnH, and azobisisobutyronitrile was added in PhCH₃ including compound 1 at 110° C. (b) The nitirle compound 2 was hydrolyzed to give compound 3 with carboxylic acid cleanly in such condition as KOH, EtOH/H₂O, H₂O₂, Δ.

2. A-[3]-triol (5)

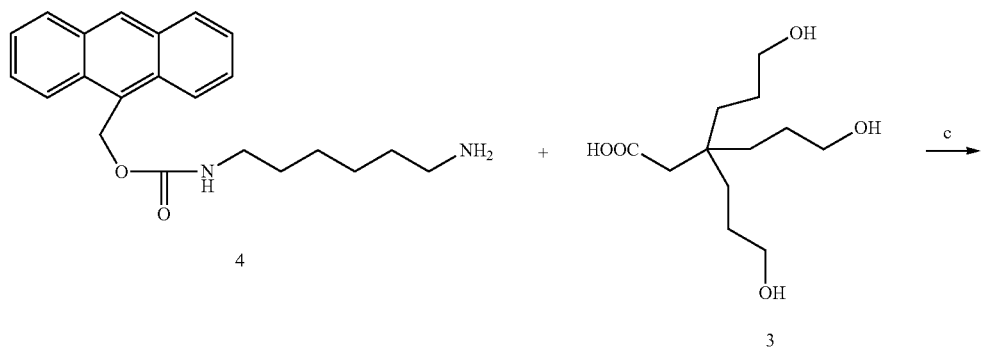

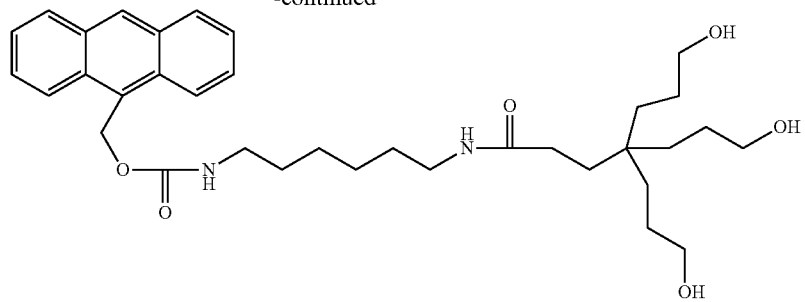
5
(c) [1]-acid-[3]-triol was linked with compound 4 through an amide coupling reaction using 1-[3-(dimethylamino)propyl]-3-ethylcarbodiimide hydrochloride (EDC) and 1-hydroxybenzotriazole hydrate (HOBT).
3. A-[3]-tribromide (6)
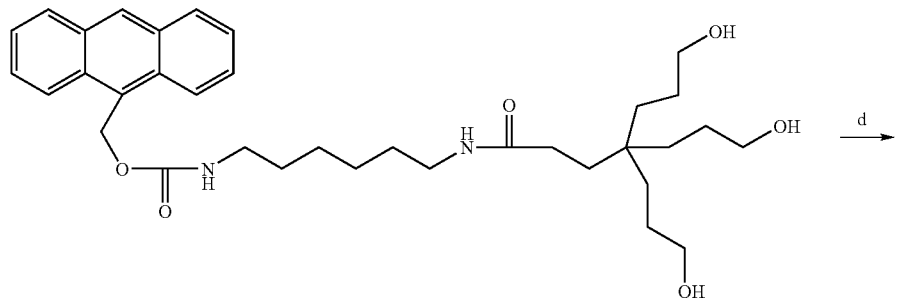
5
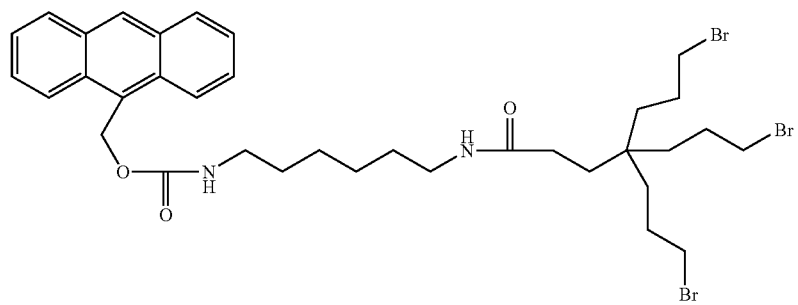
6

(d) The alcohol was used to synthesize tribromide by bromination with HBr/H$_2$SO$_4$ at 100° C.

4. [1]-CN-[3]-OBzl (8)

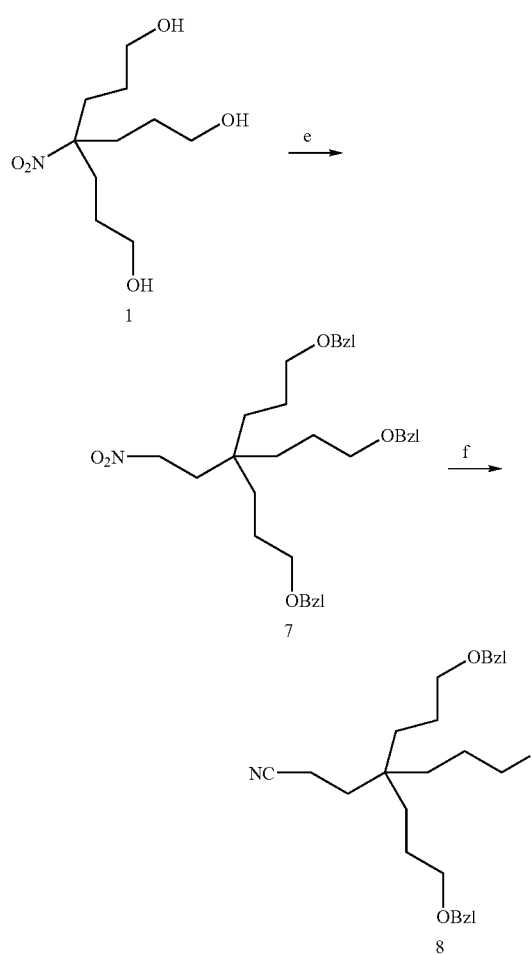

(e) The triol 1 was treated with benzyl chloride to give trisether using Me$_2$SO and KOH. (f) The trisether 8 was cyanoethylated affording the nitrile compound 9. Acrylonitrile, nBu$_3$SnH, and azobisisobutyronitrile was added in PhCH$_3$ including compound 8 at 110° C.

5. [1]-OH-[3]-OBzl (11)

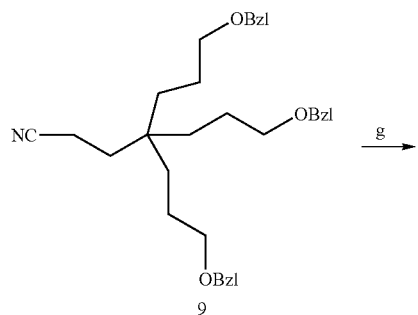

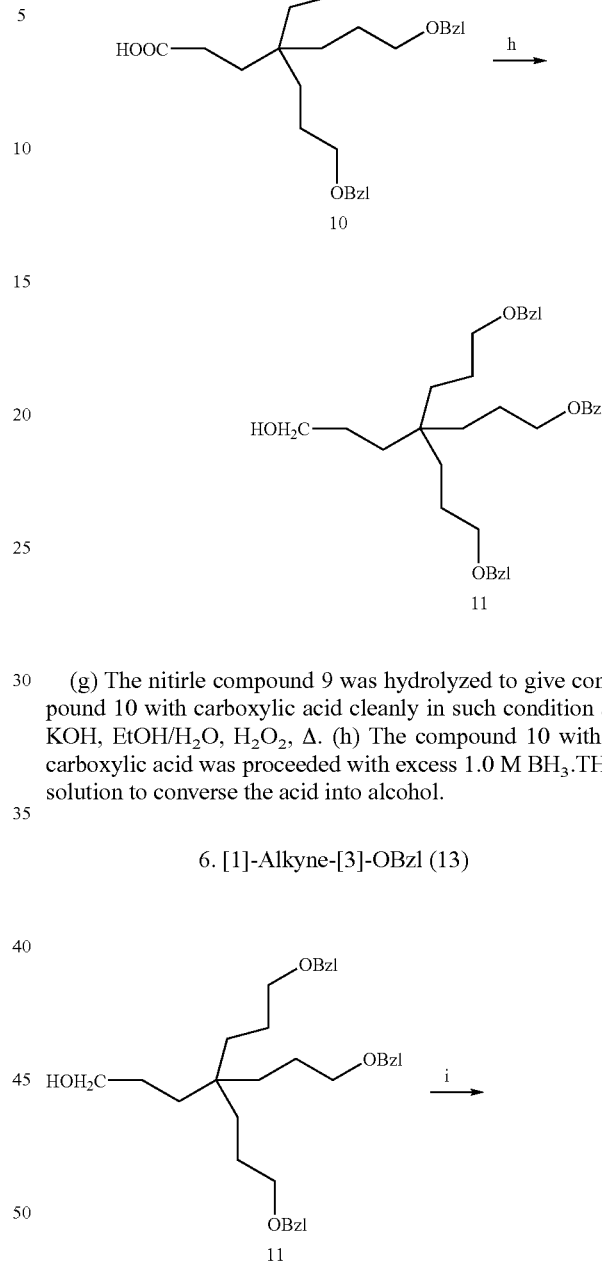

(g) The nitirle compound 9 was hydrolyzed to give compound 10 with carboxylic acid cleanly in such condition as KOH, EtOH/H$_2$O, H$_2$O$_2$, Δ. (h) The compound 10 with a carboxylic acid was proceeded with excess 1.0 M BH$_3$.THF solution to converse the acid into alcohol.

6. [1]-Alkyne-[3]-OBzl (13)

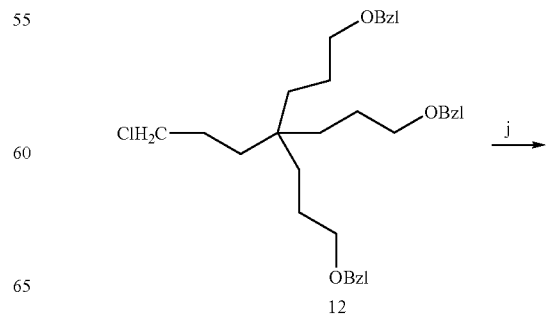

-continued
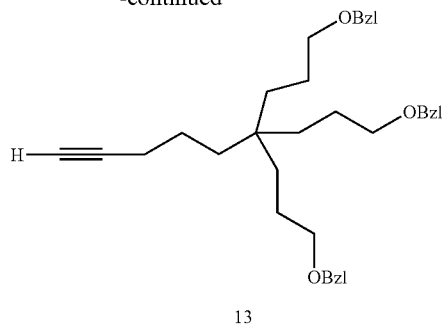
13
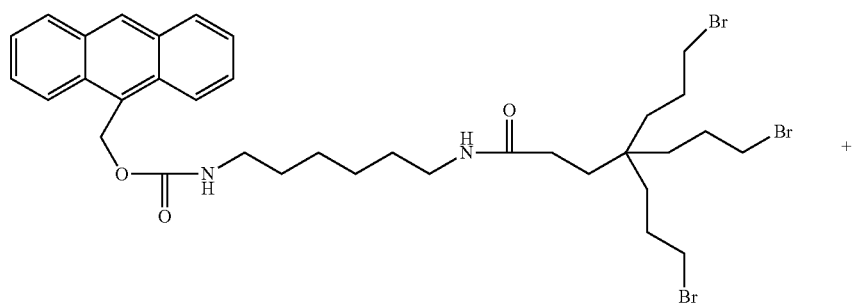
6
(i) The alcohol was transformed into chloride ($CH_2Cl_2$) with excess $SOCl_2$ and a catalytic amount of pyridine. (j) The chloride was reacted with lithium acetylide ethylenediamine complex in dimethylsulphoxide at 40° C.
7. A-[3]-Alkyne-[9]-OBzl (14)
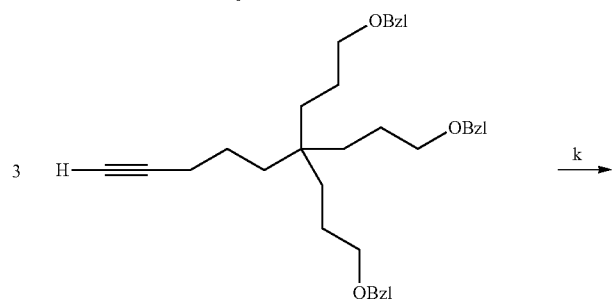
13
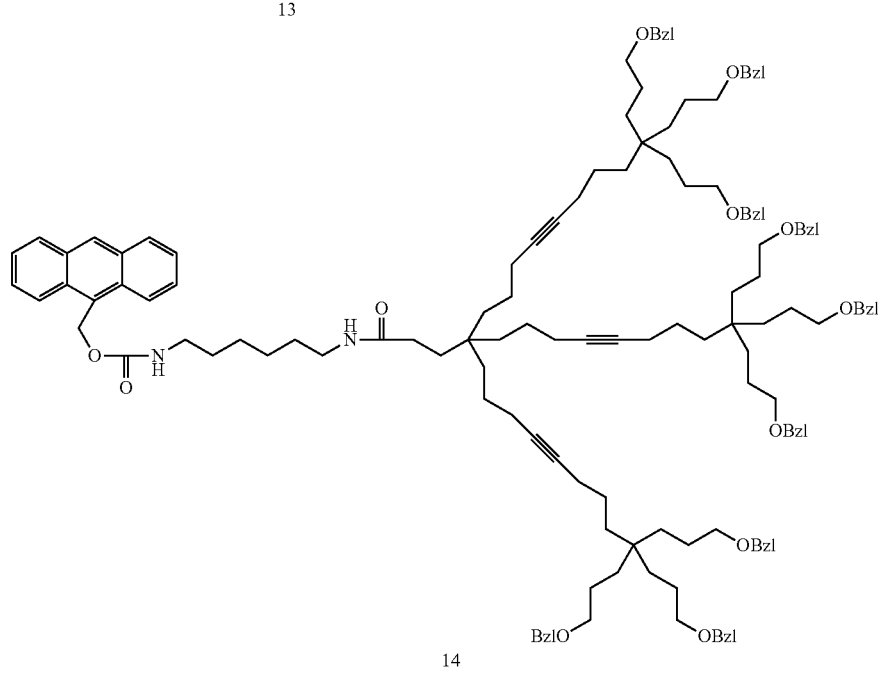
14

(k) The A-[3]-OBzl 6 was alkylated with 4 equivalents of terminal alkyne building block 13, hexamethylphosphoric rtriamide (HMPA), lithium diisopropylamide (LDA), and tetramethylethylenediamine (TMED) at 0-40° C. for 1.5 h.
Example 3.7
1. A-[9]-OH (15)
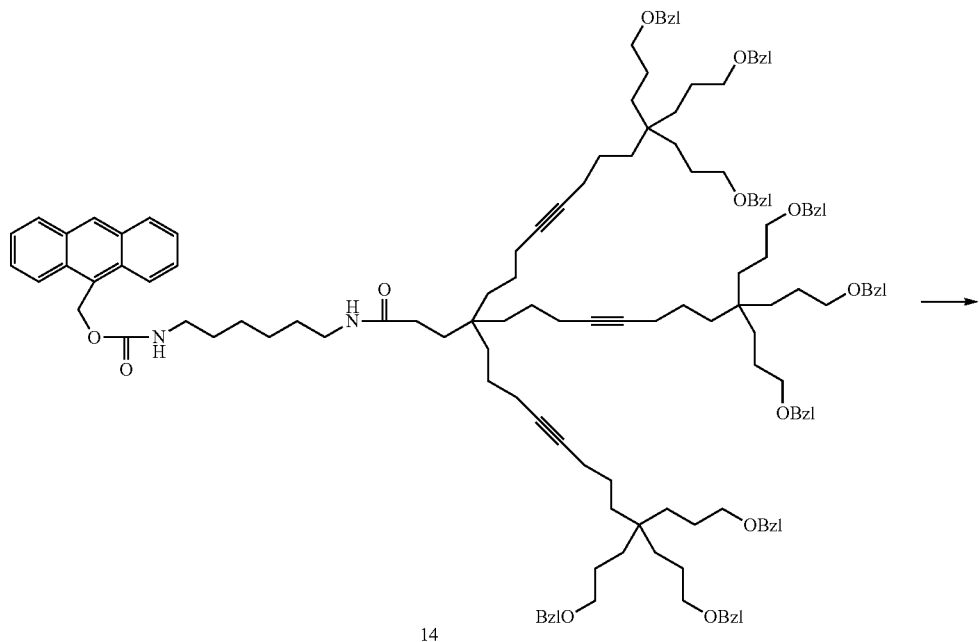
14
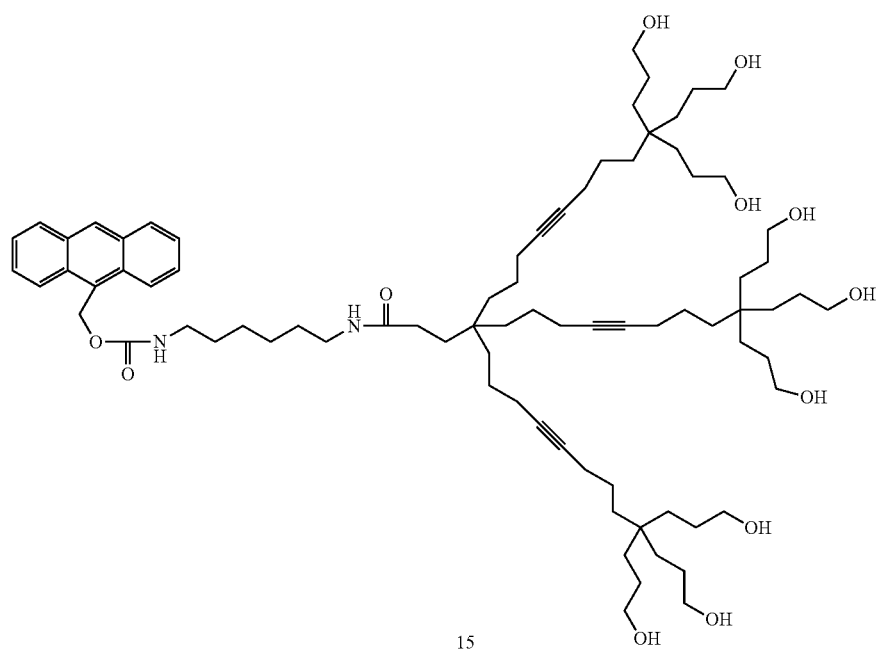
15

A-[3]-Alkyne-[9]-OBzl 14 was reduced and deprotected with Pd—C/H to produce A-[9]—OH, 15 in EtOH and THF solution including 10% Pd—C/H at 60° C. for 4d.
2. A-[27]-COOH (17)
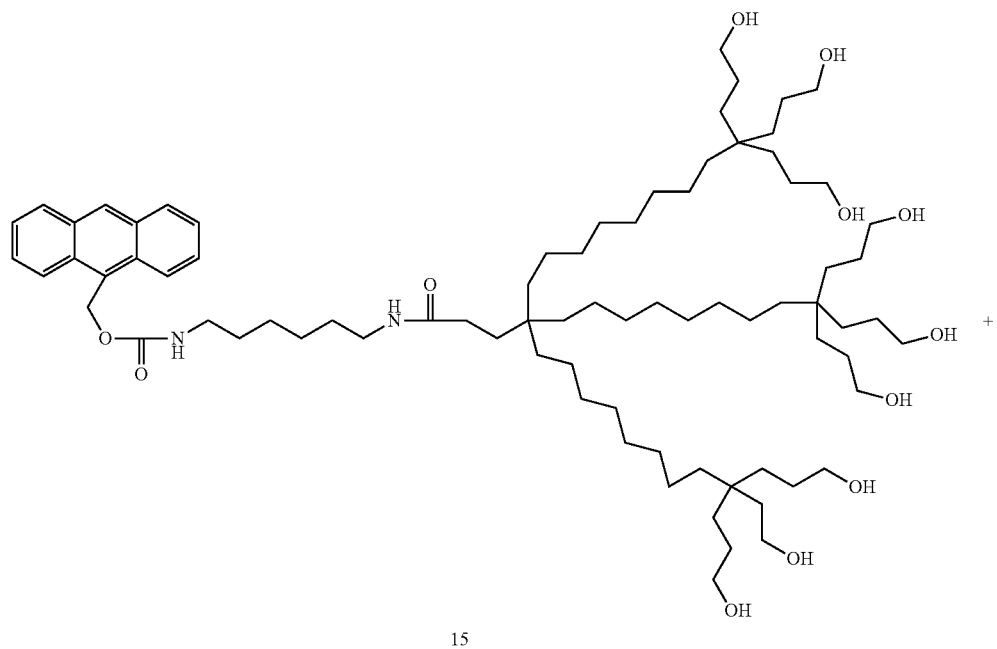
15
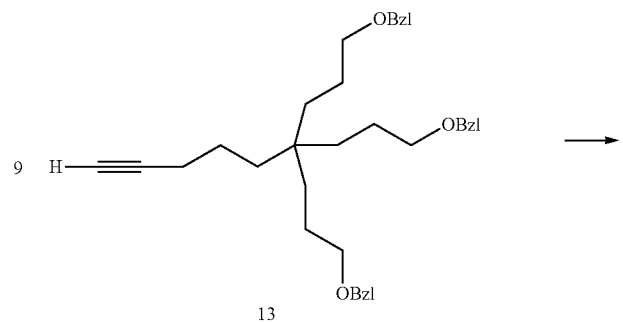
13
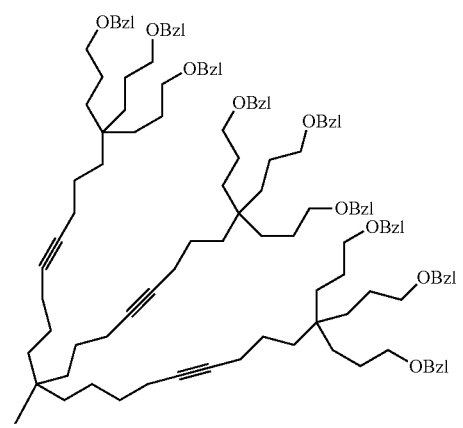

-continued
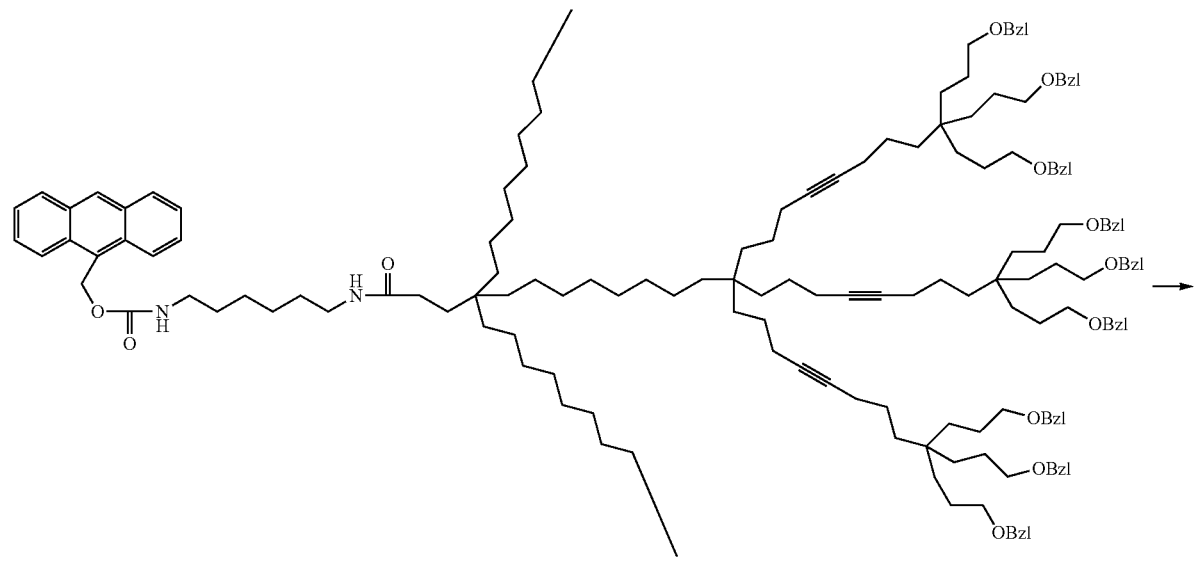
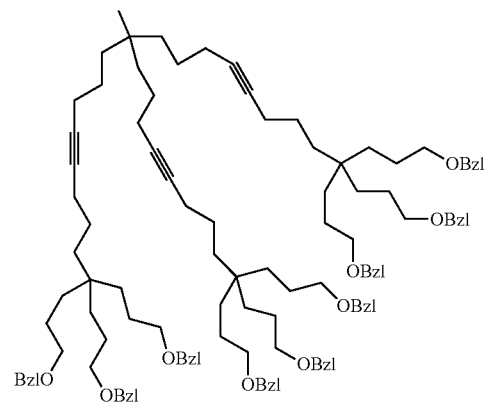
16
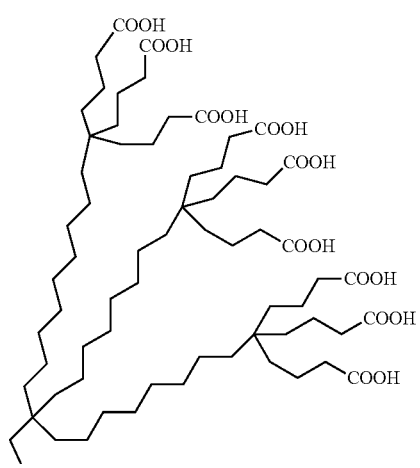

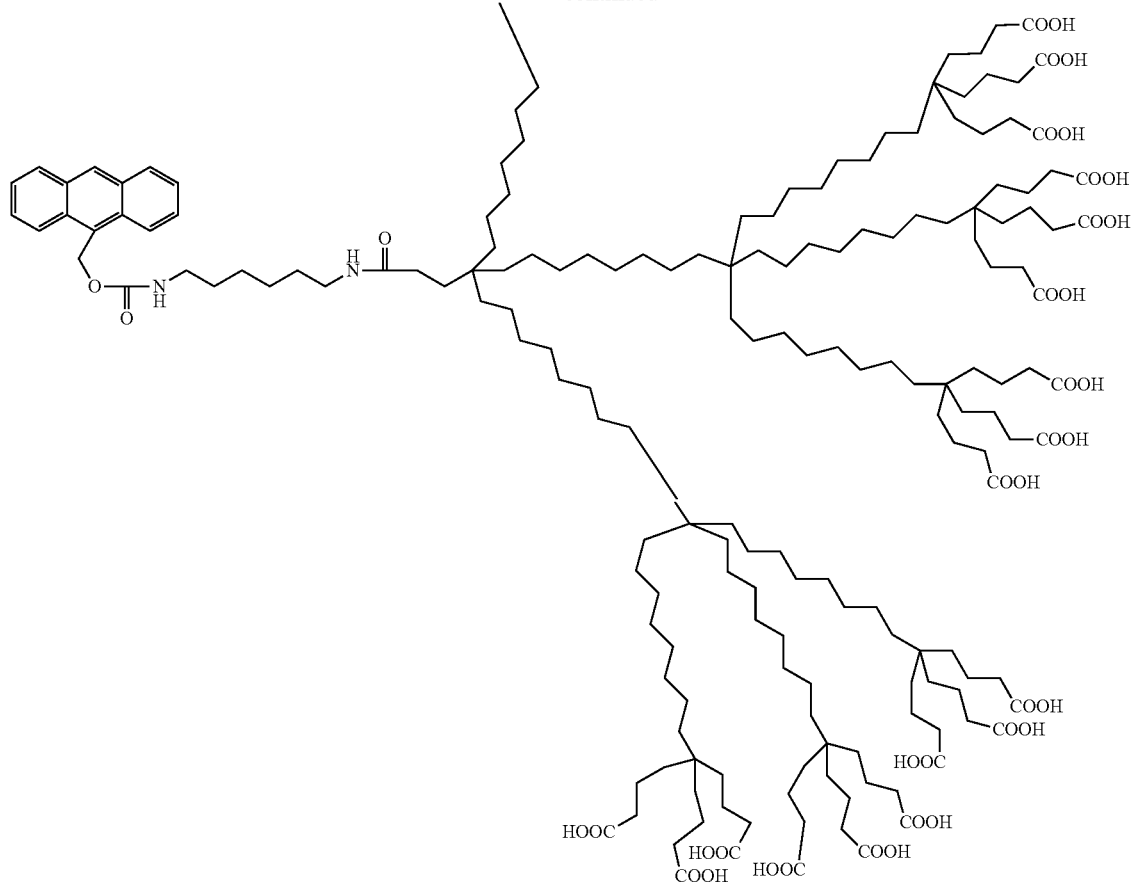

17

The alcohol was smoothly converted into the nonabromide employing SOBr$_2$ in CH$_2$Cl$_2$ at 40° C. for 12 h. And then the nonabromide compound was alkylated with 12 equivalents of [I]-Alkyne-[3]-OBzl 13 to give 49% of A-[9]-Alkyne-[27]-OBzl 16. A-[9]-Alkyne-[27]-OBzl 16 were reduced and deprotected in one step with Pd—C/H in EtOH and THF solution including 10% Pd—C/H at 60□ for 4d yielding 89% of A-[27]-OH. A-[27]-OH was oxidized by RuO$_4$ treating with NH$_4$OH or (CH$_3$)$_4$NOH to achieve 85% of A-[27]-COOH, 17.

Example 3.8

1) [G1]-(OMe)$_2$ (3)

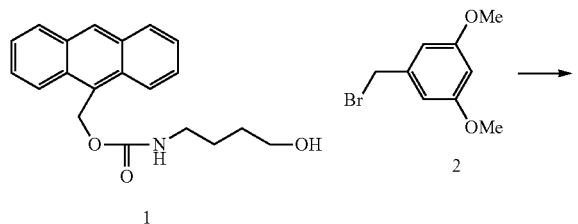

1          2

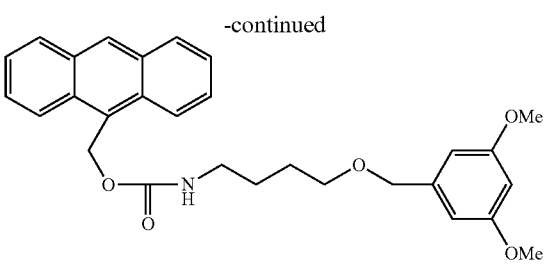

3

A mixture of compound 1 (1.05 mol equiv.), 3,5-dimethoxybenzyl bromide (1.00 mol equiv. 2), potassium carbonate (1.1 mol equiv.) and 18-c-6 (0.2 mol equiv.) in dry acetone was heated at reflux under nitrogen for 48 h. The mixture was cooled and evaporated to dryness, and the residue was partitioned between CH$_2$Cl$_2$ and water. The aqueous layer was extracted with CH$_2$Cl$_2$ (3 x), and the combined organic layers were dried and evaporated to dryness. The crude product was purified by flash chromatography with EtOAc—CH$_2$Cl$_2$ as eluent to give compound 3.

2) [G1]-(OH)₂ (4)

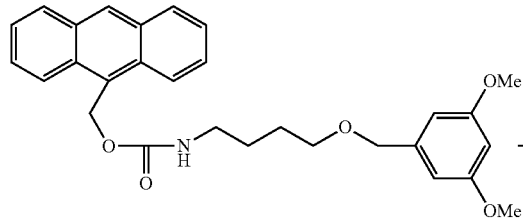

3

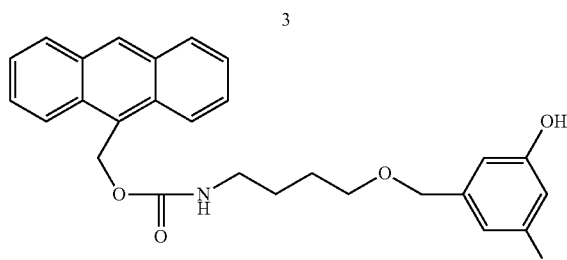

4

Methyl ether group of compound 3 was deprotected by BBr₃ in EtOAc solution for 1 h, and the crude product was purified by flash chromatography with MeOH-EtOAc as eluent to give compound 4.

3) [G2]-(OMe)₄ (5)

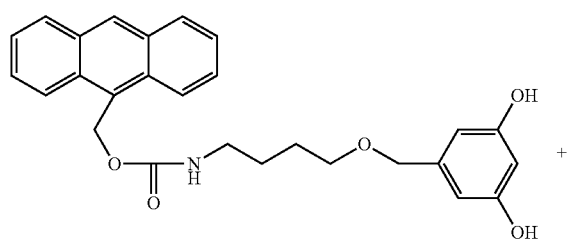

4

+

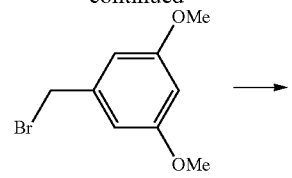

2

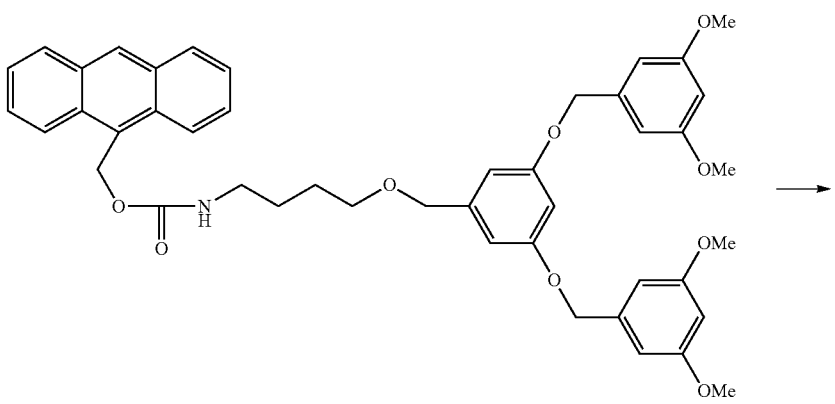

5

A mixture of [G1]-(OH)₂ (1.00 mol equiv. 4), 3,5-dimethoxybenzyl bromide (2.00 mol equiv. 2), potassium carbonate (2.1 mol equiv.) and 18-c-6 (0.2 mol equiv.) in dry acetone was heated at reflux under nitrogen for 48 h. The mixture was cooled and evaporated to dryness, and the residue was partitioned between CH₂Cl₂ and water. The aqueous layer was extracted with CH₂Cl₂ (3 x), and the combined organic layers were dried and evaporated to dryness. The crude product was purified by flash chromatography with EtOAc—CH₂Cl₂ as eluent to give compound 5.

4) [G2]-(OH)₄ (6)

5

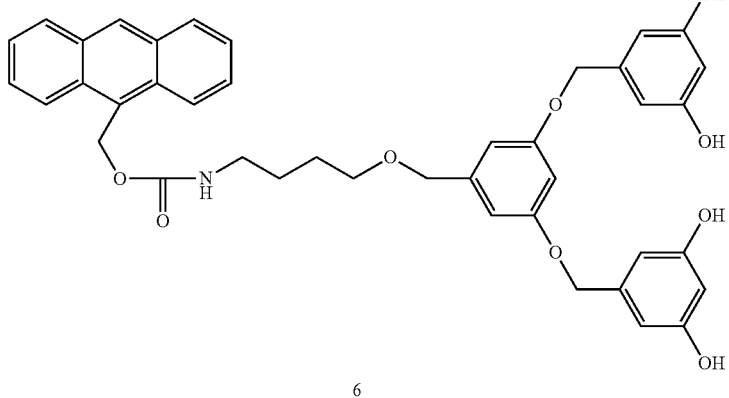
6
Methyl ether group of compound 5 was deprotected by BBr₃ in EtOAc solution for 1 h, and the crude product was purified by flash chromatography with MeOH-EtOAc as eluent to give compound 4.
5) [G3]-(OMe)$_8$ (7)
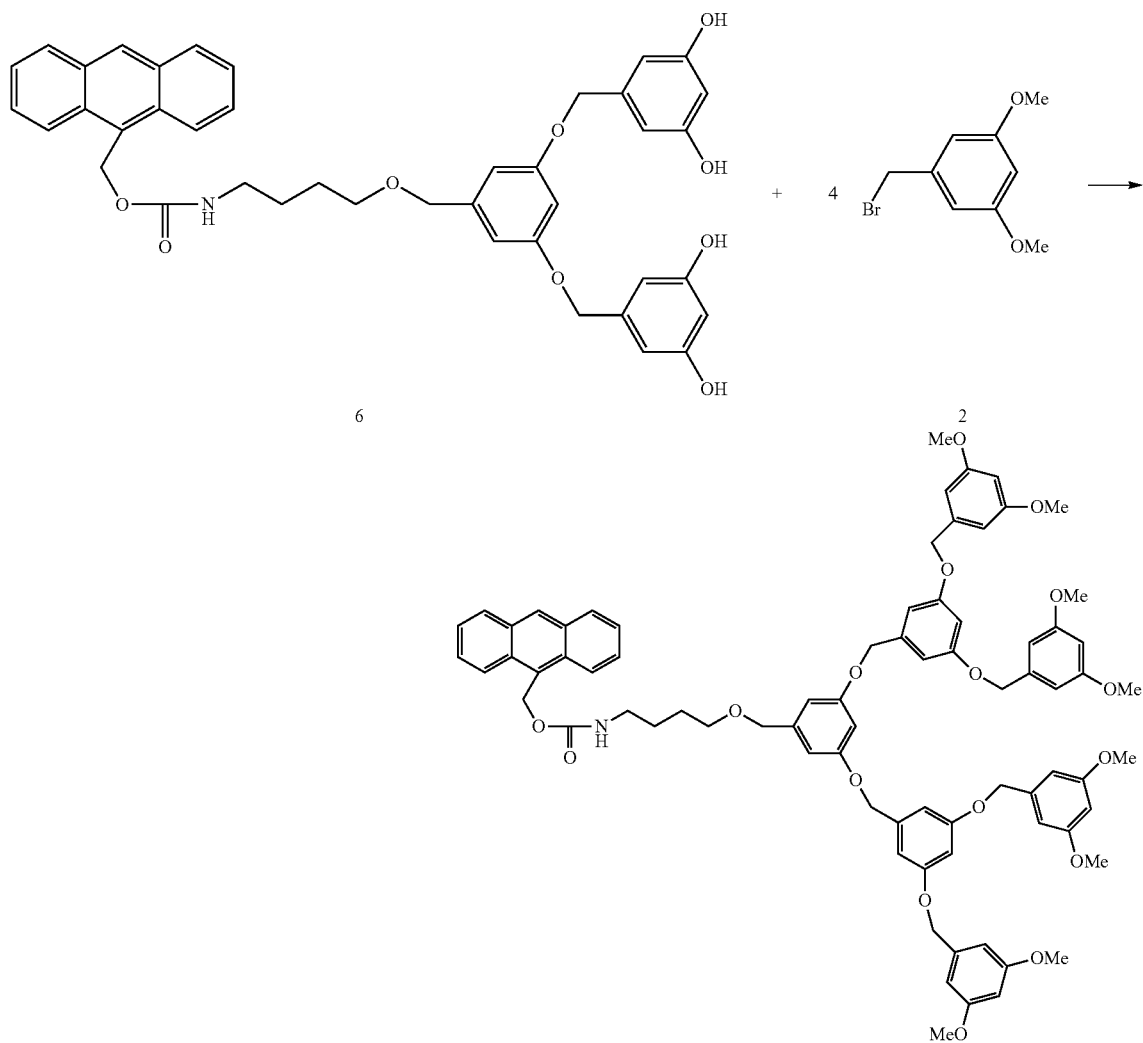

A mixture of [G2]-(OH)$_4$ (1.00 mol equiv. 6), 3,5-dimethoxybenzyl bromide (4.00 mol equiv. 2), potassium carbonate (4.1 mol equiv.) and 18-c-6 (0.2 mol equiv.) in dry acetone was heated at reflux under nitrogen for 48 h. The mixture was cooled and evaporated to dryness, and the residue was partitioned between CH$_2$Cl$_2$ and water. The aqueous layer was extracted with CH$_2$Cl$_2$ (3 x), and the combined organic layers were dried and evaporated to dryness. The crude product was purified by flash chromatography with EtOAc—CH$_2$Cl$_2$ as eluent to give compound 7.

6) [G3]-(OH)$_8$ (8)

Methyl ether group of compound 7 was deprotected by BBr$_3$ in EtOAc solution for 1 h, and the crude product was purified by flash chromatography with MeOH-EtOAc as eluent to give compound 8.

Example 4

Assembly of the Dendron on a Substrate

TMAC (N-trimethoxysilylpropyl-N,N,N-trimethylammonium chloride) was self-assembled on oxide glass instead of APDES. The dendrimer layer on TMAC layer did not need to cap the residual amine.

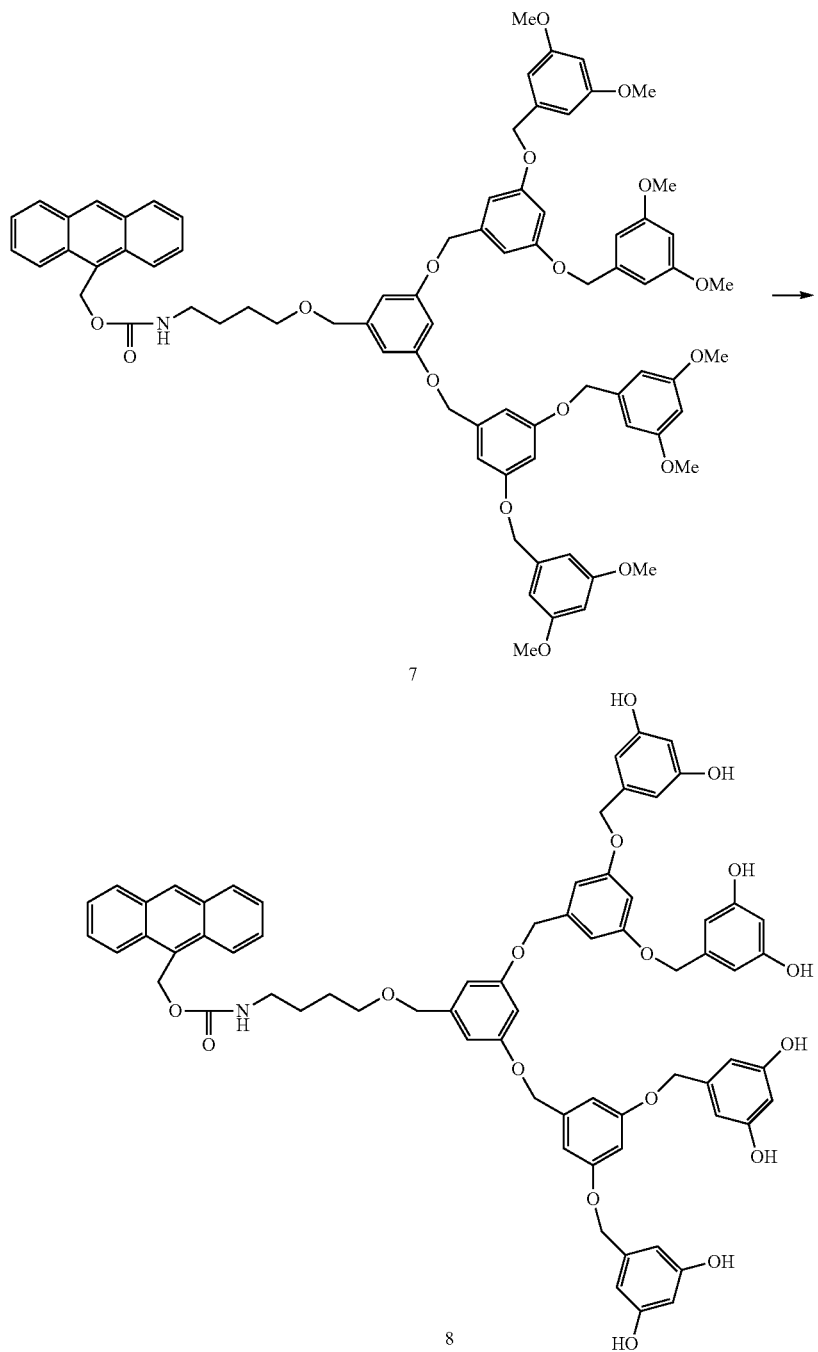

Aminosilylation with TMAC. Clean substrates (slide glass) were placed into a solution of TMAC (2 mL) and acetone (100 mL) for 5 h. After the self-assembly, the substrates were taken out of the flask, washed with acetone. The substrates were placed in an oven, and heated at 110° C. for 40 min. After immersion in acetone, the substrates were sonicated for 3 min. The washed substrate was placed in a Teflon vessel, and placed in a glass container with a big screw cap lined with an O-ring, and eventually the container was evacuated (30-40 mTorr) to dry the substrate.

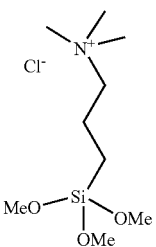

Structure of TMAC (N-trimethoxysilylpropyl-N,N,N-trimethylammonium chloride).

Self-assembly of the Fmoc-spacer-[9]acid was performed in same condition to the case of CBz-[9]acid with exception of capping of the residual amines by acetic anhydride Self-Assembly of the Fmoc-spacer-[9]acid (5). A certain amount of the Fmoc-spacer-[9]acid (5) was dissolved in a mixed solvent (DMF:deionized water=1:1 (v/v)) to make a solution of 20 mL. The solution was added into a Teflon vessel, and subsequently pieces of the above prepared aminosilylated slide glass were placed in the solution. While allowing the flask at room temperature to self-assemble, each piece of the substrate was taken out of the solution after 1 day. Right after being taken out, the plate was washed with a copious amount of deionized water. Each substrate was sonicated for 3 min in deionized water, a mixture of deionized water-methanol (1:1 (v/v)), and methanol in a sequential manner. After sonication, the substrates were placed in a Teflon vessel, and placed in a glass container with a big screw cap lined with an O-ring, and eventually the container was evacuated (30-40 mTorr) to dry the substrate.

Deprotection of Fmoc from the Self-Assembled Fmoc-spacer-[9]acid (5). Teflon vessels containing 5% piperidine in DMF were prepared. The self-assembled substrates were immersed in the vessels, and stirred for 20 min. Each substrate was sonicated for 3 min in acetone, and MeOH in a sequential manner and evacuated in a vacuum chamber (30-40 mTorr).

Example 5 p53 Microarray on Dendron (9-acid and 27-acid) Modified Surface

Seven codons, 175, 215, 216, 239, 248, 273, and 282 which are already known to be missense mutational hotspots with unusually high frequency were selected for this study. Codons 175, 248, 273, and 282 of 7 codons were taken from the international TP53 mutation database (IARC, http//:www-p53.iarc.fr/p53DataBase.htm) and the other three codons 215, 216, and 239 from Korean p53 mutational hotspot database. The capture probe sequences (the DNA immobilized on dendron-modified surface) for seven codons were designed by software and their lengths were 15-23 mer varied from codon to codon to set Tm to around 55° C.

Example 5.1

Detection of 7 Hot Spot Mutations of p53 Gene Using Single Dendron-Modified Surface The dendron-modified substrates were applied to the detection of single mutation of p53 tumor suppressor gene in cancer cell line. Target DNA samples (100-200 mer) which span 7 hot spot codons (175, 215, 216, 239, 248, 273, and 282) were amplified from the DNA extracted from cancer cells by random priming (See EXAMPLE 5.8) and allowed to hybridize with the capture probe (oligonucleotides of 15-25 mer) corresponding to the 7 hot spot codons that had been immobilized. The fluorescence intensity of each hybridized spot was determined with confocal laser scanner and the SNP discrimination efficiency was calculated. This study shows the quality of DNA microarray on dendron-modified surface for the detection of single mutation in real target sample.

Example 5.2

Effect of Length of Probe Oligonucleotide with T30 on Hybridization Efficiency and SNP Discrimination The effect of the length of capture probe for the SNP discrimination efficiency was tested by varying the length of capture probes with T30. After immobilizing capture oligonucleotides corresponding to codons 175 and 239 containing T30 by linking the 5' end of the specific sequence and the terminal primary amino group on dendron-modified surface, p53 target DNA was hybridized and fluorescence intensity was measured. This study shows dependence of the SNP discrimination efficiency and signal intensity on the length of the capture probe.

Example 5.3

Concentration of Capture Probe vs. Intensity; and Concentration of Capture Probe vs. SNP Discrimination Dependence of signal intensity and SNP discrimination efficiency on the concentration of capture probes was investigated. Capture probes on dendron-modified surface, at various concentrations, were allowed to hybridize with target DNA and the fluorescence intensity and SNP discrimination efficiency were determined. Optimal concentration of capture probe for p53 was determined.

Example 5.4

Concentration of Target Probe vs. Intensity; and Concentration of Target Probe vs. SNP Discrimination Dependence of signal intensity and SNP discrimination efficiency on the concentration of target probes was investigated. Target DNAs of various concentration were applied to hybridization and the fluorescence intensity and SNP discrimination efficiency were determined. This work provides the dynamic range of DNA microarray on dendron-modified surface.

Example 5.5

Detection of Mutation in Mixed Target Samples

Point mutations with target samples in which the mutated target sequences exist in a small portion compared with normal sequence (5 or 10%) may be detected. Samples containing two kinds of target DNAs were prepared with different molar ratio and used for hybridization to detect single point mutation in certain codon in mixtures of normal as well as mutated target DNA. This work has clinical importance for detecting early stage cancer.

Example 5.6

Detection of Mutation in Ten Unknown Colon Cancer Cell Lines

The inventive system is used to detect mutations in unknown cancer cell lines.

Example 5.6.1

Cell Cultures and Genomic DNA Extraction

The colon cancer cell lines SNU-C1, SNU-C5, COLO 201, COLO 205, DLD-1, LS 513, HCT-15, LS 174T, HCT 116, and SW480 were purchased from KCLB (Korea Cell Line Bank, Seoul, Korea). Cells were cultured in RPMI 1640 supplemented with 10% fetal bovine serum (FBS), 100 µg/ml streptomycin and 100 U penicillin (GibcoBRL, Carlsbad, Calif.) and incubated in 5% $CO_2$ at 37° C. The colon cancer cells ($2 \times 10^6$ cells) were harvested for genomic DNA extraction by Invisorb® spin cell mini kit (Invitek, Berlin, Germany) following the manufacturer's instructions. From these genomic DNAs, p53 target DNAs were prepared (see EXAMPLE 5.8.2) and DNA microarray experiment were performed using the same procedure described above.

Example 5.7

Effect of Length of Target Probe on Hybridization Efficiency and SNP Discrimination By preparing different lengths of target DNAs by several different methods such as random priming, PCR, and DNase degradation the effect of length of target probe on hybridization and SNP discrimination efficiency was investigated.

Example 5.8

Experimental Protocol

Example 5.8.1

Genomic DNA Samples

Genomic DNAs of SNU-cell lines (SNU-61, 216, 475, 563, 601, 668, 761, and 1040) were kind gifts from Jae-Gab Park, College of Medicine in Seoul National University. The provided SNU-cell lines were human carcinoma cell lines from individual Korean patients. The characteristics of these cell lines were previously described and have been used in various studies (Bae I S et al., 2000, Park J G et al., 1997, Kang M S et al., 1996, Yuan Y et al., 1997, 378-87).

Example 5.8.2

Subcloning and Sequencing p53 genes, especially between exon 5 and exon 8, for each cell lines were amplified by PCR with 2 pairs of synthetic oligonucleotide primers used in the previous report: Exon 5 Fwd 1,5'-CTG ACT TTC AAC TCT GTC TCC T-3' (SEQ ID NO:5); Exon 5 Fwd II, 5'-TAC TCC CCT GCC CTC AAC AA-3' (SEQ ID NO:6); Exon 8 Rev 1,5'-TGC ACC CTT GGT CTC CTC CAC-3' (SEQ ID NO:7); Exon 8 Rev II, 5'-CTC GCT TAG TGC TCC CGG G-3' (SEQ ID NO:8) (Kang M S et al., 1996). Each genomic DNA was amplified with 10 pmoles of first primer pair (exon 5 Fwd I and Exon 8 Rev I, corresponding to intron 4 and intron 8), 250 µM dNTP mix, 2.5 U Taq polymerase (NEB) in 1× ThermoPol buffer (supplemented with Taq polymerase) for 20 µl of total reaction volume in Multiblock System (Hybaid, UK) using the following settings: initiation activation of the polymerase at 95° C. for 1 minute, then 20 cycles of 95° C. for 30 sec, 58° C. for 30 sec, 72° C. for 90 sec, followed by final elongation step at 72° C. for 5 min. First PCR products were diluted and used as template for second PCR. The amplified genomic DNA PCR products were diluted 20 fold and used for the second nested PCR under the same conditions as the previous step except PCR was performed with 10 pmoles of the second primer pair (exon 5 Fwd II and exon 8 Rev II, corresponding to exon 5 and exon 8) and the cycle for amplification was increased to 25 cycles. The final nested PCR products were purified by gel extraction method. PCR products from genomic DNA were ligated into pGEM T-easy vector (Promega) and transformed to DH5a cells. Subcloned plasmid was purified by QIAGEN Plasmid Min kit (QIAGEN Inc., Valencia, Calif.) for sequencing analysis. Bidirectional sequencing was performed using pUC/M13 Forward and Reverse Sequencing Primer as follows: M13 FWD 5'-GTT TTC CCA GTC ACG ACG TTG-3' (SEQ ID NO:9) and M13 REV 5'-TGA GCG GAT AAC AAT TTC ACA CAG-3' (SEQ ID NO:10).

Example 5.8.3

Preparation of Target Probe

DNA target probes spanning SNP sites were random primed and labeled in a Multiblock System (Hybaid, UK) using 50 ng of template DNA with 50 U Klenow enzyme (NEB), 1× EcoPol buffer supplemented with Klenow enzyme, 6 µg of random octamer (synthesized by Bionics), low dT dNTP mix (100 µM dA,G,CTP/50 µM dTTP) and 50 µM Cyanine3-dUTP (NEN) in 20 µl of total reaction volume at 37° C. for 2 hours. Unincorporated nucleotides were separated by QIAGEN MinElute PCR purification kit (QIAGEN Inc., Valencia, Calif.). After quantitative and qualitative (specific activity, number of nucleotide per an incorporated fluorescent dye) analysis using UV/Vis spectrophotometer, qualified products were applied to the hybridization.

Example 5.8.4

Cell cultures and genomic DNA extraction. The colon cancer cell lines SNU-C1, SNU-C5, COLO 201, COLO 205, DLD-1, LS 513, HCT-15, LS 174T, HCT 116, and SW480 were purchased from KCLB (Korea Cell Line Bank, Seoul, Korea). Cells were cultured in RPMI 1640 supplemented with 10% fetal bovine serum (FBS), 100 µg/ml streptomycin and 100 U penicillin (GibcoBRL, Carlsbad, Calif.) and incubated in 5% $CO_2$ at 37° C. The colon cancer cells ($2 \times 10^6$ cells) were harvested for genomic DNA extraction by Invisorb® spin cell mini kit (Invitek, Berlin, Germany) following the manufacturer's instructions.

Example 6

Fixing Protein Probe on the Dendron

Example 6.1

Arraying NHS-biotin to the dendrimer modified slide glass. Produce the spotting solution of succinimidyl D-biotin (1.0 mg) in 1 mL sodium bicarbonate buffer 50 mM and DMSO (40% v/v). Arraying NHS-biotin to the dendrimer modified slide glass was performed using Microsys 5100 microarrayer (Cartesian Technologies, Inc, USA) in a class 10,000 clean room. After arraying and incubating for 1 h in a humidified chamber (~75% humidity), the biotin microarrays were subsequently washed for 2 h each with DMF (50° C.) THF and aqueous wash with MBST (50 mM MES, 100 mM NaCl, 0.1% Tween-20, pH, 6.0). Slides were rinsed with double-distilled water, dried, and either used immediately or stored at room temperature for several days.

Example 6.2

Detection of protein/ligand interactions. This method according to Hergenrother, P. J.; Depew, K. M.; Schreiber, S. L. *J. Am. Chem. Soc.* 2000, 122, 7849 was followed. Before adding Cy3-labeled streptavidin solution, the slides were blocked for 1 h with MBST supplemented with 3% bovine serum albumin (BSA). After a brief rinse, the slides were exposed to Cy3-labeled streptavidin solution for 30 min at room temperature. This solution was prepared by diluting stock solutions of the appropriate protein(s) with MBST supplemented with 1% BSA at a concentration of 1 μg/mL. After incubation, the slides were rinsed once with MBST and then gently agitated with four changes of MBST over the course of 12 min. The slides was dried and scanned using a commercial confocal laser scanner, ScanArray® Lite (GSI Lumonics). Quantitative microarray analysis software, Ima-Gene (BioDiscovery, Inc.) was used for image acquisition and fluorescence intensity analysis.

Example 7

Methods for Making Controlled Pore Glass Bead that Includes Size-Controlled Macromolecule Aminopropyl group tethered controlled pore glass beads (AMPCPG; 80-120 mesh; mean pore diameter, 50 nm or 300 nm) and controlled pore glass beads modified with a long chain aminoalkyl group (LCAA-CPG; 80-120 mesh; mean pore diameter, 50 nm) were purchased from CPG, Inc. 1,4-Butanediol diglycidyl ether, 1,3-diaminopropane, reduced glutathione (GSH), N-(3-methylaminopropyl)-N'-ethylcarbodiimide (EDC), N-hydroxysuccinimide (NHS), N-(9-fluorenylmethoxycarbonyloxy)chloride (Fmoc-Cl), piperidine, 4-maleimidobutyric acid N-hydroxysuccinimide ester (GMBS), phosphate buffered saline tablets (PBS) were obtained from Sigma-Aldrich. All other chemicals were of analytical reagent grade and were used without further purification. Deionized water (18 MΩ·cm) was obtained by passing distilled water through a Barnstead E-pure 3-Module system. UV-vis spectra were recorded on a Hewlett-Packard diode-array 8453 spectrophotometer.

Example 7.1

Immobilization of Glutathione on the Dendron-Modified CPG (Sample E1 and E3)

(i) Modification with Fmoc-(3)acid: AMPCPG (dry weight 0.70 g) was washed thoroughly with acetone with a glass filter. After drying in vacuum, a mixture of 1,4-butanediyl diglycidyl ether (1.0 mL) and carbonate buffer solution (2.0 mL, pH=11) was added to AMPCPG (surface capacity: 91.8 μmol/g, surface area: 47.9 m²/g). After shaking for 24 h at room temperature, the resulting beads were separated from the solution by filtration and washed thoroughly with deionized water and subsequently with acetone. Then a vial containing this sample was shaken with a mixture of 1,3-diaminopropane (1.0 mL) and carbonate buffer solution (pH=11) for 24 h at room temperature. After washing thoroughly, a mixture of 2-mercaptoethanol (1.0 mL) and aqueous sodium bicarbonate solution (2.0 mL, pH=8.5) was employed for blocking the residual epoxy group on the surface. Subsequently, an aqueous solution of dimethylformamide (30% DMF (v/v)) dissolving Fmoc-(3)acid (14 mg, 21.3 μmol), N-(3-methylaminopropyl)-N'-ethylcarbodiimide (15 mg, 77 μmol) and N-hydroxysuccinimide (9.0 mg, 77 μmol) was introduced into a vial containing the beads. After shaking for 11 h at room temperature, the beads were washed thoroughly with deionized water and subsequently with acetone. (ii) Blocking step: Acetic anhydride (1.0 mL) in anhydrous methylene chloride (2.0 mL) was allowed to react with the residual amine overnight at room temperature. (iii) Deprotection step: After washing the beads with methylene chloride and subsequently with acetone, 20% piperidine in DMF (3.0 mL) was added in a vial holding the beads, and the vial was shaken for 30 min. (iv) Ligand-immobilization step: A mixture of 1,4-butanediyl diglycidyl ether (1.0 mL) and carbonate buffer solution (2.0 mL, pH=11) was added again into the vial, and the mixture was shaken for another 24 h at room temperature. After washing the beads with deionized water and subsequently with acetone, the reduced glutathione (GSH, 5.4 mg, 17.6 μmol) in sodium bicarbonate solution (3.0 mL, pH, 8.5) was added into a vial containing the beads, and the vial was shaken for 12 h at room temperature. After washing the beads, a mixture of 2-mercaptoethanol (1.0 mL) and aqueous sodium bicarbonate solution (2.0 mL, pH=8.5) was added into the vial containing the beads. Finally, the beads were separated, washed, dried in vacuum, and stored at 4° C. under dry nitrogen atmosphere. The same steps were followed exactly to prepare the sample E3 as described above, except that Fmoc-(9) acid was used instead of Fmoc-(3) acid.

Example 7.2

Preparation of Other GSH Tethered Matrices for Control Experiment. (Sample CS, CL, and A)

(i) Sample CS and CL: GSH was immobilized directly on both AMPCPG and LCAA-CPG through GMBS linker. The beads (0.10 g) were washed thoroughly with acetone with a glass filter. After being dried in vacuum, a mixture of DMF and sodium bicarbonate buffer (1.0 mL, 3:7 (v/v), pH=8.5) dissolving 4-maleimidobutyric acid N-hydroxysuccinimide ester (GMBS, 3.0 mg, 11 μmol) was added into a vial containing the beads. After four hours of shaking at room temperature, the resulting beads were separated from the solution by filtration and washed thoroughly with deionized water and subsequently with acetone. Finally, acetic anhydride (1.0 mL) in anhydrous methylene chloride (2.0 mL) was allowed to react with residual amine group on the matrix. After thorough washing, glutathione (GSH, 3.4 mg, 11 µmol) in PBS buffer (1.0 mL) was added into a vial containing the beads, and the vial was shaken for 12 h at room temperature. After 2-mercaptoethanol (1.0 mL) was used to block the residual maleimido group, the beads were separated, washed, dried in vacuum. (ii) Sample A: The same modification steps for E1 and E3 were followed to modify AMPCPG with 1,4-butanediyl diglycidyl ether and 1,3-diaminopropane. After the capping with 2-mercaptoethanol, 1,4-butanediyl diglycidyl ether was employed to generate an epoxy group. Finally, glutathione was immobilized, and 2-mercaptoethanol was used to open the remaining epoxy group on the beads.

Example 7.3

Determination of Amine Density on the Modified Beads

Either modified beads on the way to E1 or E3 or beads for control experiments (10 mg) were taken into an e-tube. In parallel, 9-fluorenylmethyl chloroformate (Fmoc-Cl, 1.75 mg) and $Na_2CO_3$ (1.45 mg) were placed into a separate glass vial, and a mixed solvent (2:1 (v/v) 1,4-dioxane and water, 2.5 mL) was added to dissolve the reagents. One fifth of the solution was taken and transferred into the e-tube containing the beads. The tube was placed into a vial, and the vial was shaken for 12 h at room temperature. The beads were separated with a glass filter, and the porous materials were washed with deionized water and subsequently with acetone. After being dried in vacuum, 20% piperidine in DMF (0.50 mL) was added into an e-tube containing the beads. The beads were allowed to react with piperidine for 30 min. Then the resulting solution from the tube was transferred carefully into a new e-tube, and the beads were washed with 20% piperidine in DMF (0.25 mL) twice. All of the solution was added into the previous e-tube. Then the solution was mixed with a certain volume of methanol to adjust the absorbance. The absorbance at 301 nm was measured using a UV/N is spectrometer, and a relevant solvent was used for the background correction. To increase reliability, the measurements were carried out with five different samples.

For calibration, we prepared a series of the solution of N-Fmoc-ethanolamine (or 9-fluorenylmethyl N-(2-hydroxyethyl)carbamate) (30 µM-70 µM) in 20% piperidine in DMF. After allowing 30 min for the reaction, the solutions containing dibenzofulvene were utilized for measuring absorbance, and calculating the absorption coefficient.

Example 7.4

Preparation of GST Fusion Protein Lysate

GST-fusion proteins were prepared as described before, Kim, J. H.; Lee, S.; Kim, J. H.; Lee, T. G.; Hirata, M.; Suh, P.-G.; Ryu, S. H.; *Biochemistry* 2002, 41, 3414-3421, which is incorporated by reference herein in its entirety. For large scale cultures, the single colony containing a recombinant pGEX plasmid was incubated into 200 ml of 2×YTA medium. After growing to log phase, gene expression was induced with IPTG for another 6 h. Subsequently, cells were pelleted by centrifugation and washed with 1×PBS. Then *E. coli* was lysed in 10 mL hypotonic buffer (20 mM Tris, 150 mM NaCl, 1.0 mM $MgCl_2$, 1.0 mM EGTA, pH, 7.4) containing 0.50 mM PMSF by the sonicator. The proteins were obtained by the removal of insoluble material.

Example 7.5

Binding Assays (i) The effect of chain length: The prepared beads CL (5.72 mg), CS (6.97 mg), E1 (10.0 mg), and E3 (14.8 mg) were incubated separately with the mixed solution including GST lysates in 0.8 mL of the incubation buffer (20 mM Tris, 150 mM NaCl, 1.0 mM $MgCl_2$, 1.0 mM EGTA, 1% TX-100, 0.10 mM PMSF, pH, 7.4, 0.50 mM PMSF) for 1 h at 4° C., washed with the 10 bed volume of incubation buffer for three times and then 100 µL of the SDS-sample buffer was added. After the tubes were cooked for 5 min at 95° C., 20 µL samples were utilized for SDS-PAGE and the gel was stained by CBB G-250 staining solution. (ii) Selectivity of the dendron-treated matrices: 10 mg of samples A, E1, and E3, as well as 100 µg of purified GST or GST-fused protein lysate were used in this experiment. The other steps were same as described above.

Example 7.6

Figure 13:
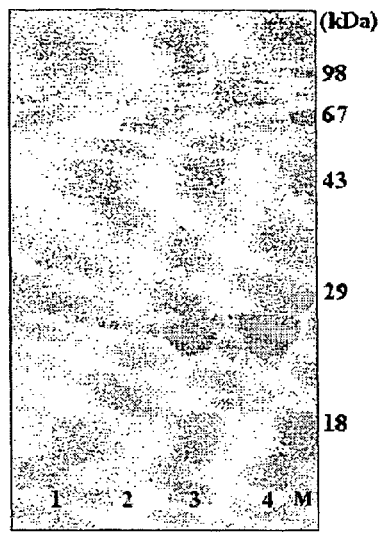
FIG. 13 shows binding of GST from cell lysate was recorded for two control beads, CL and CS in comparison with E1 and E3. M: markers; Lane 1: CL; Lane 2: CS; Lane 3: E1; Lane 4: E3.

Elution of GST Fusion Proteins from Glutathione Sepharose-4B, E1 and E3:

Glutathione Sepharose-4B, E1, and E3 were processed as described in 'Binding assays (i)'. The amount of the protein bound to beads was determined using Image gauge V3.12 (FUJI PHOTO FILM CO., LTD.). The same steps were followed for PX domain of p47$^{phox}$ and Munc-18 fragment lysates (FIG. 13).

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A substrate for detecting the presence of a mutation in a gene, said substrate comprising a molecular layer of a plurality of regularly spaced size-controlled, cone shaped macromolecules, wherein each of said macromolecule comprises a polymer comprising a linear region and a plurality of branched regions in which a plurality of termini on the branched region are covalently bound to the substrate, and the terminus of the linear region is fixed with a target-specific oligonucleotide via a functional group, wherein said polymer is of the formula:

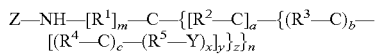

wherein
each of m, a, b, and c is independently 0 or 1;
x is 1 when c is 0 or when c is 1, x is 3;
y is 1 when b is 0 or when b is 1, y is 3;
z is 1 when a is 0 or when a is 1, z is 3;
n is 3;
each of $R^1$, $R^2$, $R^3$, $R^4$, and $R^5$ is independently a moiety of the formula

Z is said target-specific oligonucleotide; and
Y is carboxylic acid terminal group that is bound to the substrate;
provided the product of n, x, y, and z is at least 3, and wherein said macromolecules are spaced at regular intervals between about 0.1 nm and about 100 nm between the linear functionalized groups.

2. The substrate according to claim 1, wherein said macromolecules are spaced at regular intervals of about 10 nm.

3. The substrate according to claim 1, wherein the polymer is a dendron.

4. The substrate according to claim 1, wherein the substrate is selected from the group consisting of semiconductor, synthetic organic metal, synthetic semiconductor, metal, alloy, plastic, silicon, silicate, glass, and ceramic.

5. The substrate according to claim 4, wherein the substrate is a slide, particle, bead, micro-well, or porous material.

6. The substrate according to claim 5, wherein the porous material is a membrane, gelatin or hydrogel.

7. The substrate according to claim 5, wherein the bead is a controlled pore bead.

8. A diagnostic system for detecting a mutation in a gene, comprising the substrate according to claim 1.

9. The diagnostic system according to claim 8, wherein the substrate comprises oligonucleotides that are specific for diagnosis of cancer related genes.

10. The diagnostic system according to claim 8, wherein the substrate comprises oligonucleotides that are specific for diagnosing mutation in p53 gene.

11. A method for detecting the presence of a mutation in a gene, comprising contacting a sample containing the gene to be assayed with a substrate according to claim 1, wherein Z is a complementary oligonucleotide of the gene; and determining hybridazation between the gene and the complementary oligonucleotide to detect the presence of a mutation in the gene.

12. The method according to claim 11, wherein the gene is a cancer related gene.

13. The method according to claim 11, wherein the gene is p53.

* * * * *

SEQUENCE LISTING

<160> NUMBER OF SEQ ID NOS: 10

<210> SEQ ID NO 1
<211> LENGTH: 16
<212> TYPE: DNA
<213> ORGANISM: Artificial sequence
<220> FEATURE:
<223> OTHER INFORMATION: Probe
<220> FEATURE:
<221> NAME/KEY: misc_feature
<222> LOCATION: (9)..(9)
<223> OTHER INFORMATION: n can be a, t, g, or c.

```
<400> SEQUENCE: 1
ccattccgng tgtcca                                                    16

<210> SEQ ID NO 2
<211> LENGTH: 45
<212> TYPE: DNA
<213> ORGANISM: Artificial sequence
<220> FEATURE:
<223> OTHER INFORMATION: Probe
<220> FEATURE:
<221> NAME/KEY: misc_feature
<222> LOCATION: (38)..(38)
<223> OTHER INFORMATION: n can be a, t, g, or c.

<400> SEQUENCE: 2
tttttttttt tttttttttt tttttttttt cattccgngt gtcca                    45

<210> SEQ ID NO 3
<211> LENGTH: 15
<212> TYPE: DNA
<213> ORGANISM: Artificial sequence
<220> FEATURE:
<223> OTHER INFORMATION: Target

<400> SEQUENCE: 3
tggacactcg gaatg                                                     15

<210> SEQ ID NO 4
<211> LENGTH: 45
<212> TYPE: DNA
<213> ORGANISM: Artificial sequence
<220> FEATURE:
<223> OTHER INFORMATION: Target

<400> SEQUENCE: 4
cctacgaaat ctactggaac gaaatctact tggacactcg gaatg                    45

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5
ctgactttca actctgtctc ct                                             22

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
tactcccctg ccctcaacaa                                                20

<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7
tgcacccttg gtctcctcca c                                              21
```

```
<210> SEQ ID NO 8
<211> LENGTH: 19
<212> TYPE: DNA
<213> ORGANISM: Artificial sequence
<220> FEATURE:
<223> OTHER INFORMATION: Primer

<400> SEQUENCE: 8
ctcgcttagt gctcccggg                                             19

<210> SEQ ID NO 9
<211> LENGTH: 21
<212> TYPE: DNA
<213> ORGANISM: Artificial sequence
<220> FEATURE:
<223> OTHER INFORMATION: Primer

<400> SEQUENCE: 9
gttttcccag tcacgacgtt g                                          21

<210> SEQ ID NO 10
<211> LENGTH: 24
<212> TYPE: DNA
<213> ORGANISM: Artificial sequence
<220> FEATURE:
<223> OTHER INFORMATION: Primer

<400> SEQUENCE: 10
tgagcggata acaatttcac acag                                       24
```